(12) United States Patent
Wang et al.

(10) Patent No.: US 11,276,478 B2
(45) Date of Patent: Mar. 15, 2022

(54) METHODS AND SYSTEMS FOR QUANTIFYING GENE EXPRESSION IN SYNTHETIC GENE CIRCUITS AND FOR TUNING SYNTHETIC GENE CIRCUITS

(71) Applicant: ARIZONA BOARD OF REGENTS ON BEHALF OF ARIZONA STATE UNIVERSITY, Scottsdale, AZ (US)

(72) Inventors: Xiao Wang, Chandler, AZ (US); Qi Zhang, Tempe, AZ (US); Fuqing Wu, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 581 days.

(21) Appl. No.: 16/248,720

(22) Filed: Jan. 15, 2019

(65) Prior Publication Data

US 2019/0221281 A1 Jul. 18, 2019

Related U.S. Application Data

(60) Provisional application No. 62/617,584, filed on Jan. 15, 2018.

(51) Int. Cl.
*G16B 5/00* (2019.01)
*C12N 15/63* (2006.01)
*G16B 5/30* (2019.01)

(52) U.S. Cl.
CPC ............. *G16B 5/00* (2019.02); *C12N 15/635* (2013.01); *G16B 5/30* (2019.02)

(58) Field of Classification Search
None
See application file for complete search history.

(56) References Cited

U.S. PATENT DOCUMENTS 10,301,613 B2 5/2019 Wang et al.

FOREIGN PATENT DOCUMENTS

WO 2019017988 A1 1/2019

OTHER PUBLICATIONS

Ahnert, S. et al., "How much non-coding DNA do eukaryotes require?", Journal of Theoretical Biology, Jun. 2008 (available online Feb. 2008), vol. 252, No. 4, pp. 587-592 <DOI:10.1016/j.jtbi.2008.02.005>.
Bennett, M. et al., "Overpowering the component problem", Nature Biotechnology, May 2009, vol. 27, No. 5, pp. 450-451 <DOI:10.1038/nbt0509-450>.
Brophy, J. et al., "Antisense transcription as a tool to tune gene expression", Molecular Systems Biology, Jan. 2016, vol. 12, No. 1, 14 pages <DOI:10.15252/msb.20156540>.
Brophy, J. et al., "Principles of genetic circuit design", Nature Methods, May 2014 (available online Apr. 2014), vol. 11, No. 5, pp. 508-520 <DOI:10.1038/nmeth.2926>.
Cameron, E. et al., "Tunable protein degradation in bacteria", Nature Biotechnology, Dec. 2014 (available online Nov. 2014), vol. 32, No. 12, pp. 1276-1281 <DOI:10.1038/nbt.3053>.
Cao, Y. et al., "Collective Space-Sensing Coordinates Pattern Scaling in Engineered Bacteria", Cell, Apr. 2016, vol. 165, No. 3, pp. 620-630 <DOI:10.1016/j.cell.2016.03.006>.
Carr, S. et al., "Reducing DNA context dependence in bacterial promoters", PLoS One, Apr. 2017, vol. 12, No. 4, article e0176013, 15 pages <DOI:10.1371/journal.pone 0176013>.
Chen, H. et al., "Genome-wide study of mRNA degradation and transcript elongation in *Escherichia coli*", Molecular Systems Biology, Jan. 2015, vol. 11, No. 781, 10 pages <DOI:10.15252/msb.20145794>.
Chen, Y. et al., "Emergent genetic oscillations in a synthetic microbial consortium", Science, Aug. 2015, vol. 349, No. 6251, pp. 986-989 <DOI:10.1126/science.aaa3794>.
Chizzolini, F. et al., "Gene Position More Strongly Influences Cell-Free Protein Expression from Operons than T7 Transcriptional Promoter Strength", ACS Synthetic Biology, Jun. 2014 (available online Nov. 2013), vol. 3, No. 6, pp. 363-371 <DOI:10.1021/sb4000977>.
De Smit, M. et al., "Secondary structure of the ribosome binding site determines translational efficiency: a quantitative analysis", Proceedings of the National Academy of Sciences of the United States of America, Oct. 1990, vol. 87, No. 19, pp. 7668-7672 <DOI:10.1073/pnas.87.19.7668>.
Din, M. et al., "Synchronized cycles of bacterial lysis for in vivo delivery", Nature, Aug. 2016 (available online Jul. 2016), vol. 536, pp. 81-85 <DOI:10.1038/nature18930>.
Egbert, R. et al., "Fine-tuning gene networks using simple sequence repeats", Proceedings of the National Academy of Sciences of the United States of America, Oct. 2012 (available online Aug. 2012), vol. 109, No. 42, pp. 16817-16822 <DOI:10.1073/pnas.1205693109>.
Elowitz, M. et al., "A synthetic oscillatory network of transcriptional regulators", Nature, Jan. 2000, vol. 403, pp. 335-338 <DOI:10.1038/35002125>.

(Continued)

*Primary Examiner* — G Steven Vanni
(74) *Attorney, Agent, or Firm* — Rodney J. Fuller; Booth Udall Fuller, PLC

(57) ABSTRACT

A method of tuning the performance of a synthetic gene circuit comprising a plurality of genes is disclosed. The method includes quantifying, for each gene, a relative gene expression metric. The metric is quantified by determining a number of nucleotides in a 5' adjacent transcriptional region (ATR) of the gene, a number of nucleotides in a 3' ATR, a minimum free energy of a mRNA secondary structure around a ribosome binding site of the gene, a total folding energy for the 5' ATR, and a folding energy for the first 100 nucleotides of the 3' ATR, and then summing sequence-dependent energy changes, the terms including scaling coefficients and an average energy cost for synthesizing a nucleotide. The method further includes simulating, through application of the relative gene expression metrics of the plurality of genes to a deterministic model, the performance of an intended function of the synthetic gene circuit.

20 Claims, 16 Drawing Sheets

Specification includes a Sequence Listing.

(56) References Cited

OTHER PUBLICATIONS

Emory, S. et al., "A 5'-terminal stem-loop structure can stabilize mRNA in *Escherichia coli*", Genes & Development, 1992, vol. 6, pp. 135-148 <DOI:10.1101/gad.6.1.135>.
Espah Borujeni, A. et al., "Translation Initiation is Controlled by RNA Folding Kinetics via a Ribosome Drafting Mechanism", Journal of the American Chemical Society, Jun. 2016 (available online May 2016), vol. 138, No. 22, pp. 7016-7023 <DOI:10.1021/jacs.6b01453>.
Farasat, I. et al., "Efficient search, mapping, and optimization of multi-protein genetic systems in diverse bacteria", Molecular Systems Biology, Jun. 2014, vol. 10, No. 6, article 731, 18 pages <DOI:10.15252/msb.20134955>.
Ferreira, J. et al., "Tuning gene expression with synthetic upstream open reading frames", Proceedings of the National Academy of Sciences of the United States of America, Jul. 2013, vol. 110, No. 28, pp. 11284-11289 <DOI:10.1073/pnas.1305590110>.
Gardner, T. et al., "Construction of a genetic toggle switch in *Escherichia coli*", Nature, Jan. 2000, vol. 403, pp. 339-342 <DOI:10.1038/35002131>.
Kudla, G. et al., "Coding-Sequence Determinants of Gene Expression in *Escherichia coli*", Science, Apr. 2009, vol. 324, No. 5924, pp. 255-258 <DOI:10.1126/science.1170160>.
Lee, J. et al., "Creating Single-Copy Genetic Circuits", Molecular Cell, Jul. 2016, vol. 63, No. 2, pp. 329-336 <DOI:10.1016/j.molcel.2016.06.006>.
Li, J. et al., "Nucleotides upstream of the Kozak sequence strongly influence gene expression in the yeast S. cerevisiae". Journal of Biological Engineering, Aug. 2017, vol. 11, No. 25, 14 pages <DOI:10.1186/s13036-017-0068-1>.
Lim, H. et al., "Fundamental relationship between operon organization and gene expression", Proceedings of the National Academy of Sciences of the United States of America, Jun. 2011, vol. 108, No. 26, pp. 10626-10631 <DOI:10.1073/pnas.1105692108>.
Litcofsky, K. et al., "Iterative plug-and-play methodology for constructing and modifying synthetic gene networks", Mature Methods, Nov. 2012 (available online Oct. 2012), vol. 9, No. 11, pp. 1077-1080 <DOI:10.1038/nmeth.2205>.
Liu, C. et al., "Sequential Establishment of Stripe Patterns in an Expanding Cell Population", Science, Oct. 2011, vol. 334, No. 6053, pp. 238-241 <DOI:10.1126/science.1209042>.
Ma, K. et al., "Foundations and Emerging Paradigms for Computing in Living Cells", Journal of Molecular Biology, Feb. 2016, vol. 428, No. 5, Part B, pp. 893-915 <DOI:10.1016/j.jmb.2016.02.018>.
Mackie, G., "RNase E: at the interface of bacterial RNA processing and decay", Nature Reviews Microbiology, Jan. 2013 (available online Dec. 2012), vol. 11, pp. 45-57 <DOI:10.1038/nrmicro2930>.
Mao, Y. et al., "Deciphering the rules by which dynamics of mRNA secondary structure affect translation efficiency in *Saccharomyces cerevisiae*". Nucleic Acids Research, Apr. 2014 (available online Feb. 2014), vol. 42, No. 8, pp. 4813-4822 <DOI:10.1093/nar/gku159>.
Mus, F. et al., "Symbiotic Nitrogen Fixation and the Challenges to Its Extension to Nonlegumes", Applied and Environmental Microbiology, Jul. 2016 (available online Jun. 2016), vol. 82, No. 13, pp. 3698-3710 <DOI:10.1128/AEM.01055-16>.
Mutalik, V. et al., "Precise and reliable gene expression via standard transcription and translation initiation elements", Nature Methods, Apr. 2013 (available online Mar. 2013), vol. 10, No. 4, pp. 354-360 <DOI:10.1038/nmeth.2404>.
Nielsen, A. et al., "Genetic circuit design automation", Science, Apr. 2016, vol. 352, No. 6281, article aac7341, 13 pages <DOI:10.1126/science.aac7341>.
Oliva, G. et al., "Small RNAs, 5' UTR elements and RNA-binding proteins in intracellular bacteria: impact on metabolism and virulence", FEMS Microbiology Reviews, May 2015, vol. 39, No. 3, pp. 331-349 <DOI:10.1093/femsre/fuv022>.
Pardee, K. et al., "Paper-Based Synthetic Gene Networks", Cell, Nov. 2014 (available online Oct. 2014), vol. 159, No. 4, pp. 940-954 <DOI:10.1016/j.cell.2014.10.004>.
Pardee, K. et al., "Rapid, Low-Cost Detection of Zika Virus Using Programmable Biomolecular Components", Cell, May 2016, vol. 165, No. 5, pp. 1255-1266 <DOI:10.1016/j.cell.2016.04.059>.
Prindle, A. et al., "Rapid and tunable post-translational coupling of genetic circuits", Nature, Apr. 2014, vol. 508, pp. 387-391 <DOI:10.1038/nature13238>.
Rocha, E., "The Organization of the Bacterial Genome", Annual Review of Genetics, Dec. 2008, vol. 42, pp. 211-233 <DOI:10.1146/annurev.genet.42.110807.091653>.
Salis, H. et al., "Automated design of synthetic ribosome binding sites to control protein expression", Nature Biotechnology, Oct. 2009, vol. 27, No. 10, pp. 946-950 <DOI:10.1038/nbt.1568>.
Seffens, W. et al., "mRNAs have greater negative folding free energies than shuffled or codon choice randomized sequences", Nucleic Acids Research, Apr. 1999, vol. 27, No. 7, pp. 1578-1584 <DOI:10.1093/nar/27.7.1578>.
Selinger, D. et al., "Global RNA Half-Life Analysis in *Escherichia coli* Reveals Positional Patterns of Transcript Degradation", Jan. 2003, Genome Research, vol. 13, pp. 216-223 <DOI:10.1101/gr.912603>.
Serra, M. et al., "[11] Predicting thermodynamic properties of RNA", Methods in Enzymology, 1995 (available online Jan. 2004), vol. 259, pp. 242-261 <DOI:10.1016/0076-6879(95)59047-1>.
Smanski, M. et al., "Synthetic biology to access and expand nature's chemical diversity", Nature Reviews Microbiology, Mar. 2016 (available online Feb. 2016), vol. 14, pp. 135-149 <DOI:10.1038/nrmicro.2015.24>.
Taniguchi, Y. et al., "Quantifying *E. coli* Proteome and Transcriptome with Single-Molecule Sensitivity in Single Cells", Science, Jul. 2010, vol. 329, No. 5991, pp. 533-538 <DOI:10.1126/science.1188308>.
Trotta, E., "On the Normalization of the Minimum Free Energy of RNAs by Sequence Length", PLoS One, Nov. 2014, vol. 9, No. 11, article e113380, 9 pages <DOI:10.1371/journal.pone.0113380>.
Tuller, T. et al., "Translation efficiency is determined by both codon bias and folding energy", Proceedings of the National Academy of Sciences of the United States of America, Feb. 2010, vol. 107, No. 8, pp. 3645-3650 <DOI:10.1073/pnas.0909910107>.
Wright, G., "Perspective: Synthetic biology revives antibiotics", Nature, May 2014 (available online Apr. 2014), vol. 509, p. S13 <DOI:10.1038/509S13a>.
Wu, F. et al., "Applications of synthetic gene networks", Science Progress, Sep. 2015, vol. 98, No. 3, pp. 244-252 <DOI:10.3184/003685015X14368807556441>.
Wu, F. et al., "Design of Adjacent Transcriptional Regions to Tune Gene Expression and Facilitate Circuit Construction", Cell Systems, Feb. 2018, vol. 6, No. 2, pp. 206-215 <DOI:10.1016/j.cels.2018.01.010>.
Wu, F. et al., "Engineering of a synthetic quadrastable gene network to approach Waddington landscape and cell fate determination", eLife, Apr. 2017, vol. 6, article e23702, 27 pages <DOI:10.7554/eLife.23702.001>.
Wu, F. et al., "Quorum-Sensing Crosstalk-Driven Synthetic Circuits: From Unimodality to Trimodality", Chemistry & Biology, Dec. 2014 (available online Nov. 2014), vol. 21, No. 12, pp. 1629-1638 <DOI:10.1016/j.chembiol.2014.10.008>.
Xia, T. et al., "Thermodynamic Parameters for an Expanded Nearest-Neighbor Model for Formation of RNA Duplexes with Watson-Crick Base Pairs", Biochemistry, Oct. 1998, vol. 37, No. 42, pp. 14719-14735 <DOI:10.1021/bi9809425>.
Yang, L. et al., "Permanent genetic memory with >1-byte capacity", Nature Methods, Dec. 2014 (available online Oct. 2014), vol. 11, No. 12, pp. 1261-1266 <DOI:10.1038/nmeth.3147>.
Yeung, E. et al., "Biophysical Constraints Arising from Compositional Context in Synthetic Gene Networks", Cell Systems, Jul. 2017, vol. 5, No. 1, pp. 11-24 <DOI:10.1016/j.cels.2017.06.001>.
Zadeh, J. et al., "NUPACK: Analysis and design of nucleic acid systems", Journal of Computational Chemistry, Jan. 2011 (available online Jul. 2010), vol. 32, No. 1, pp. 170-173 <DOI:10.1002/jcc.21596>.

(56) References Cited

OTHER PUBLICATIONS

Zhang, W. et al., "Synthetic biology applications in industrial microbiology", Frontiers in Microbiology, Aug. 2014, vol. 5, article 451, 2 pages <DOI:10.3389/fmicb.2014.00451>.

Fig. 3A
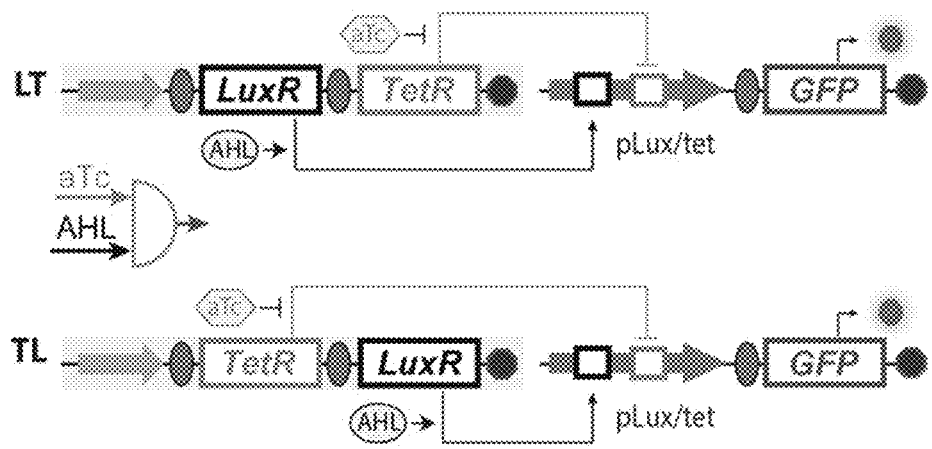
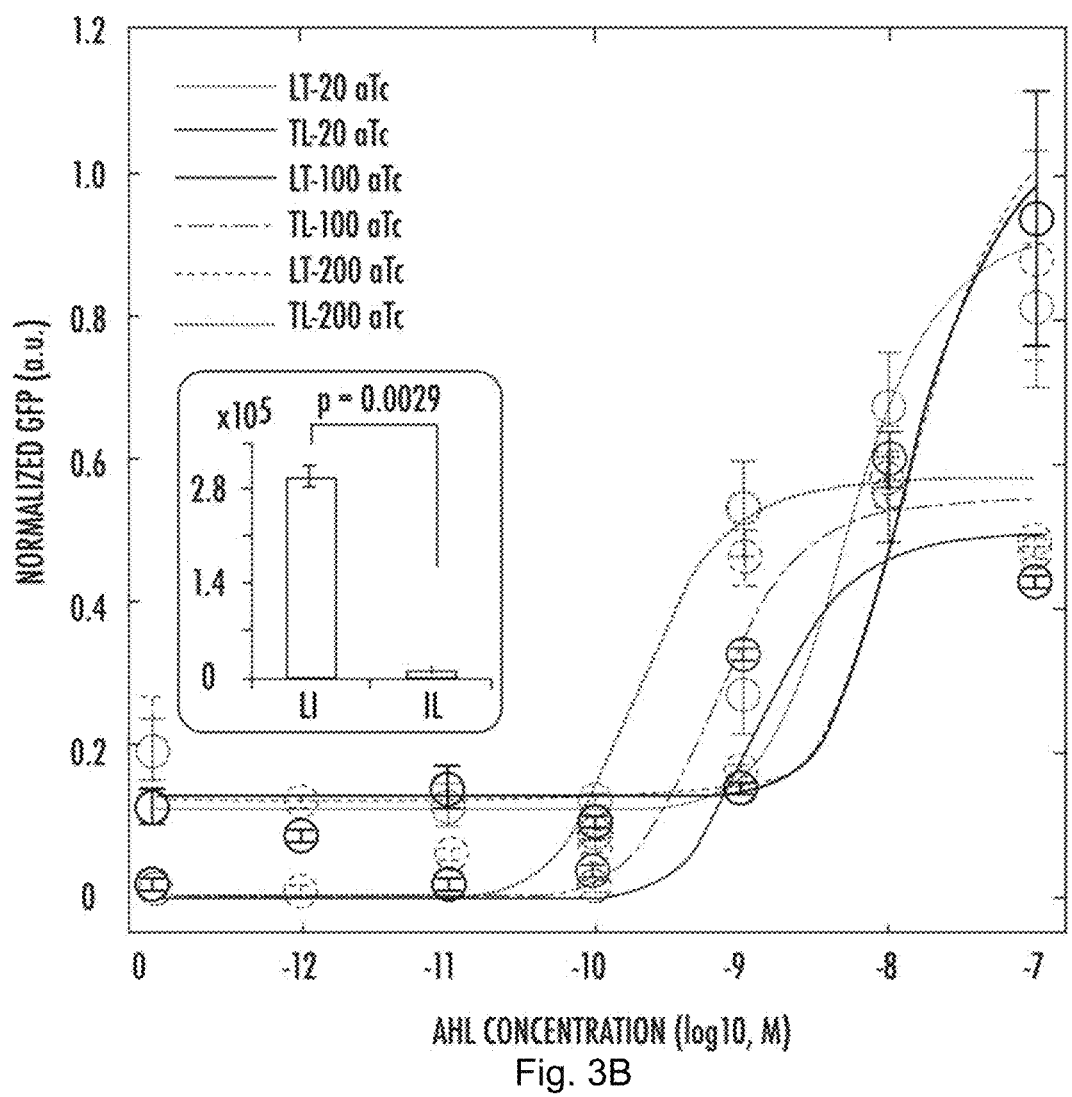
Fig. 3B

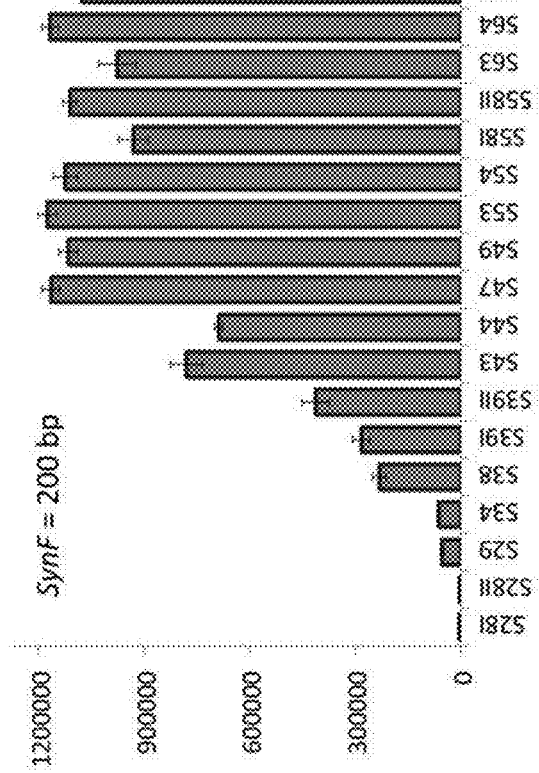
Fig. 4C
Fig. 4D
Fig. 5A

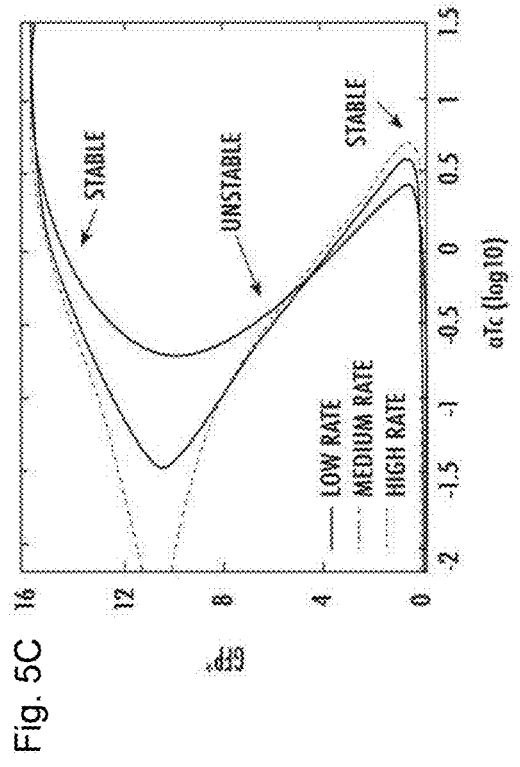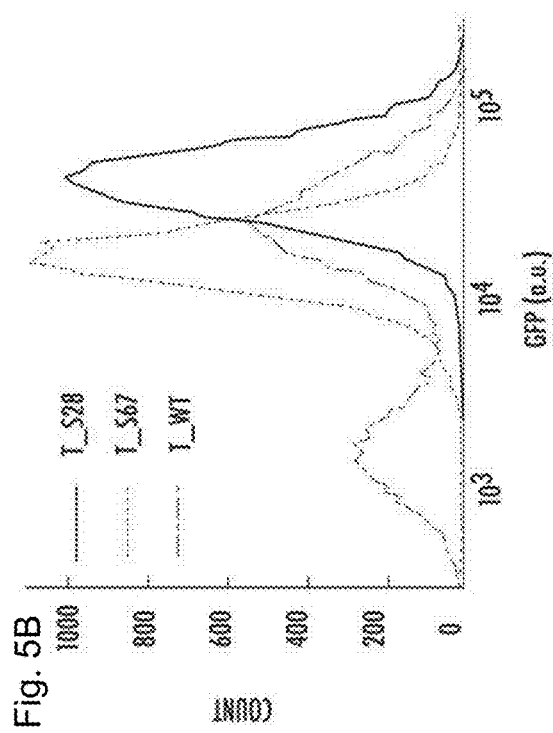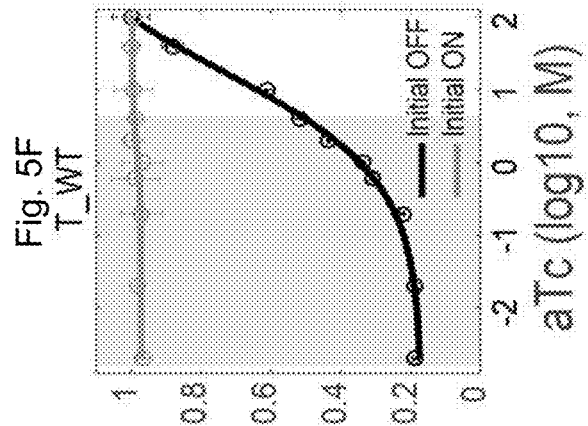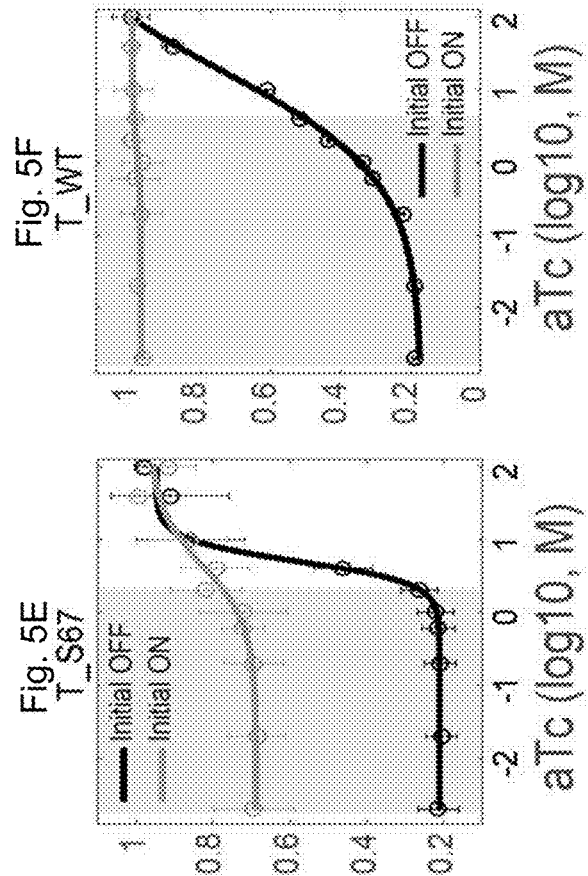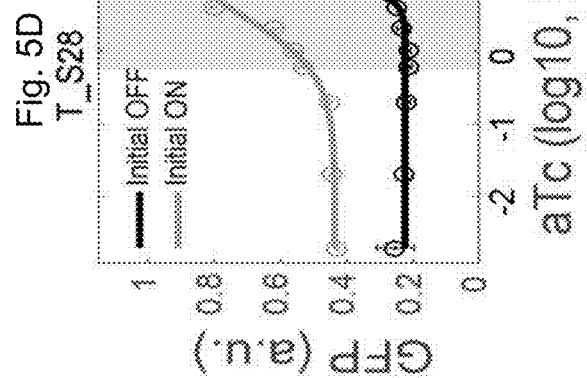

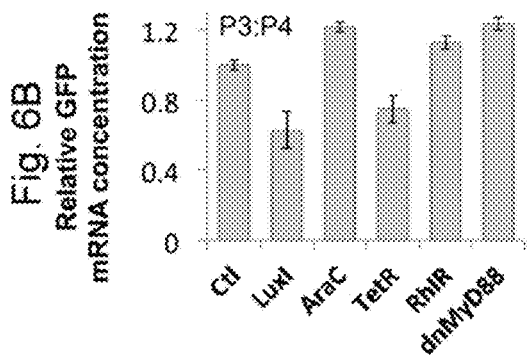
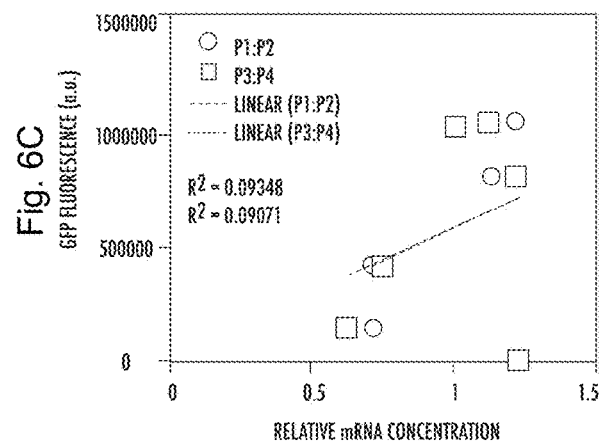
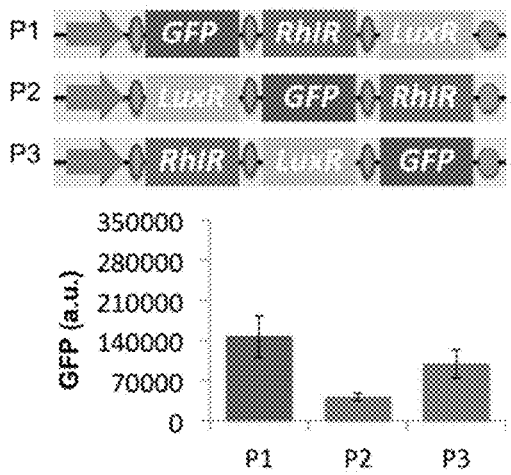
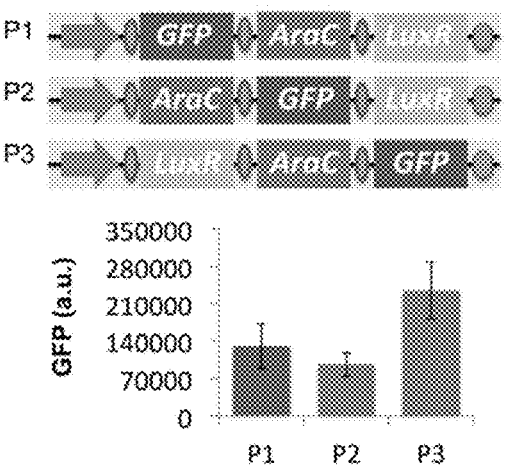
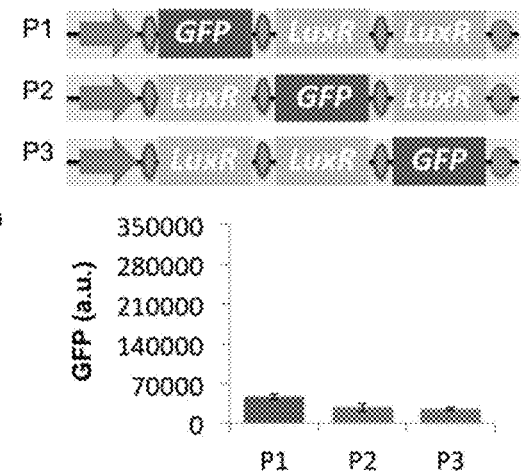
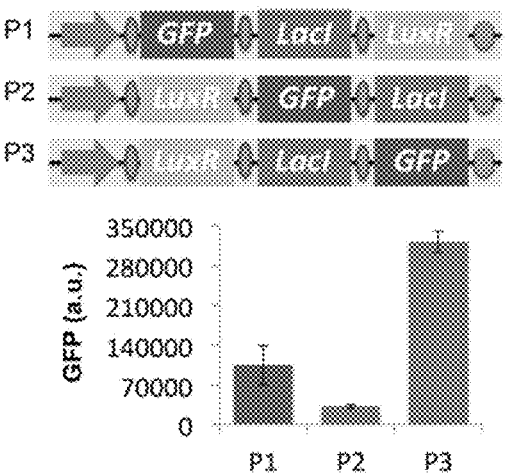

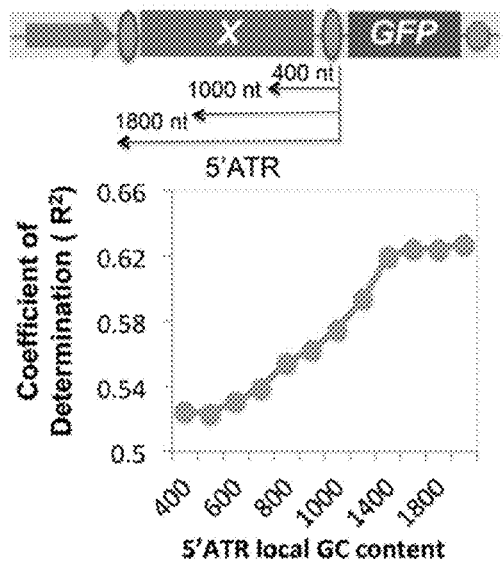
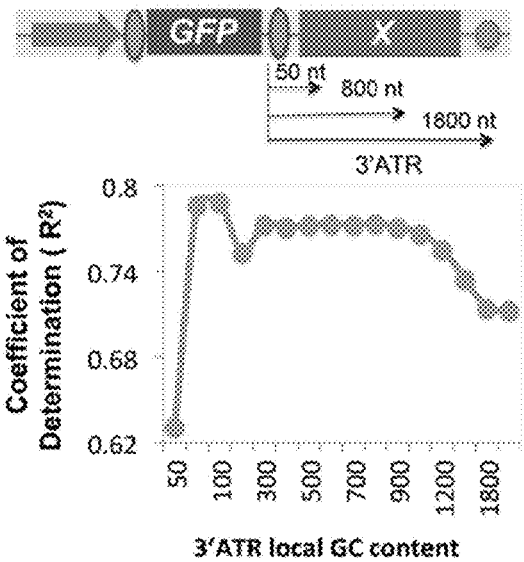
Fig. 7A
Fig. 7B
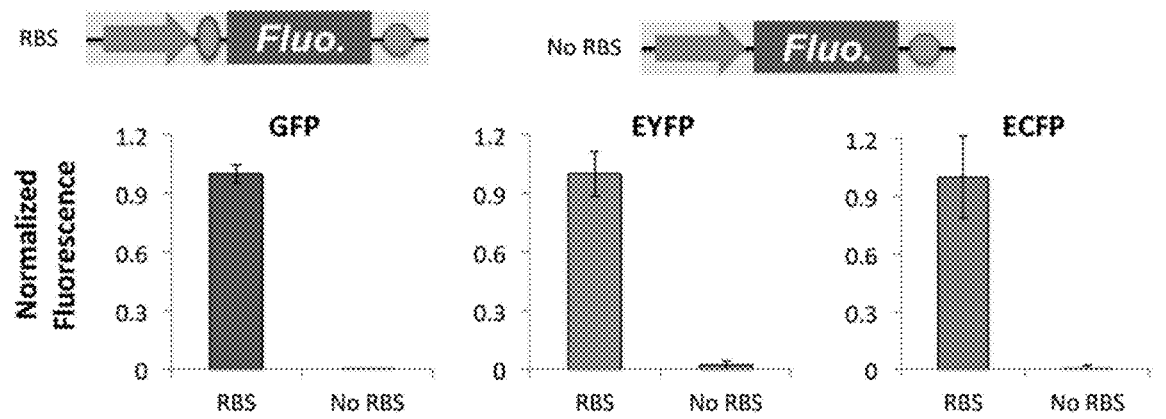
Fig. 7C
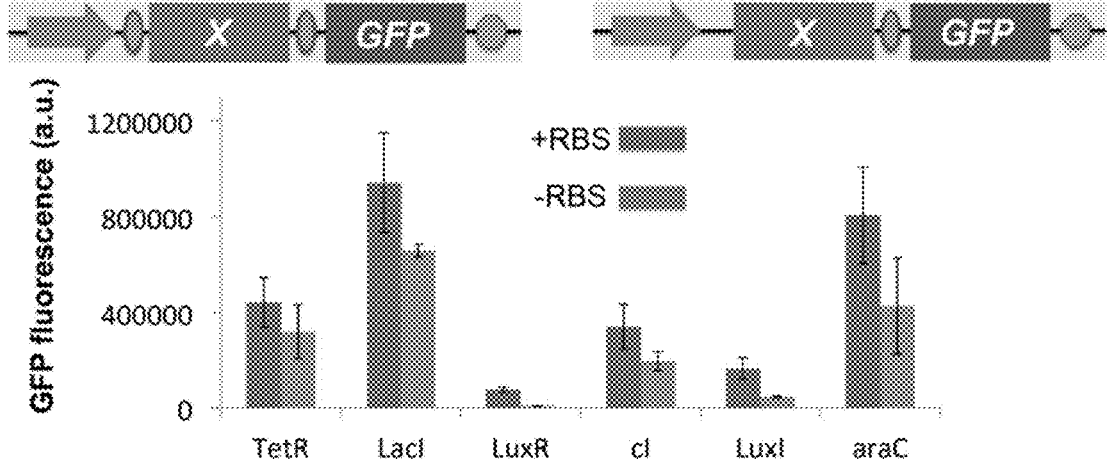
Fig. 7D

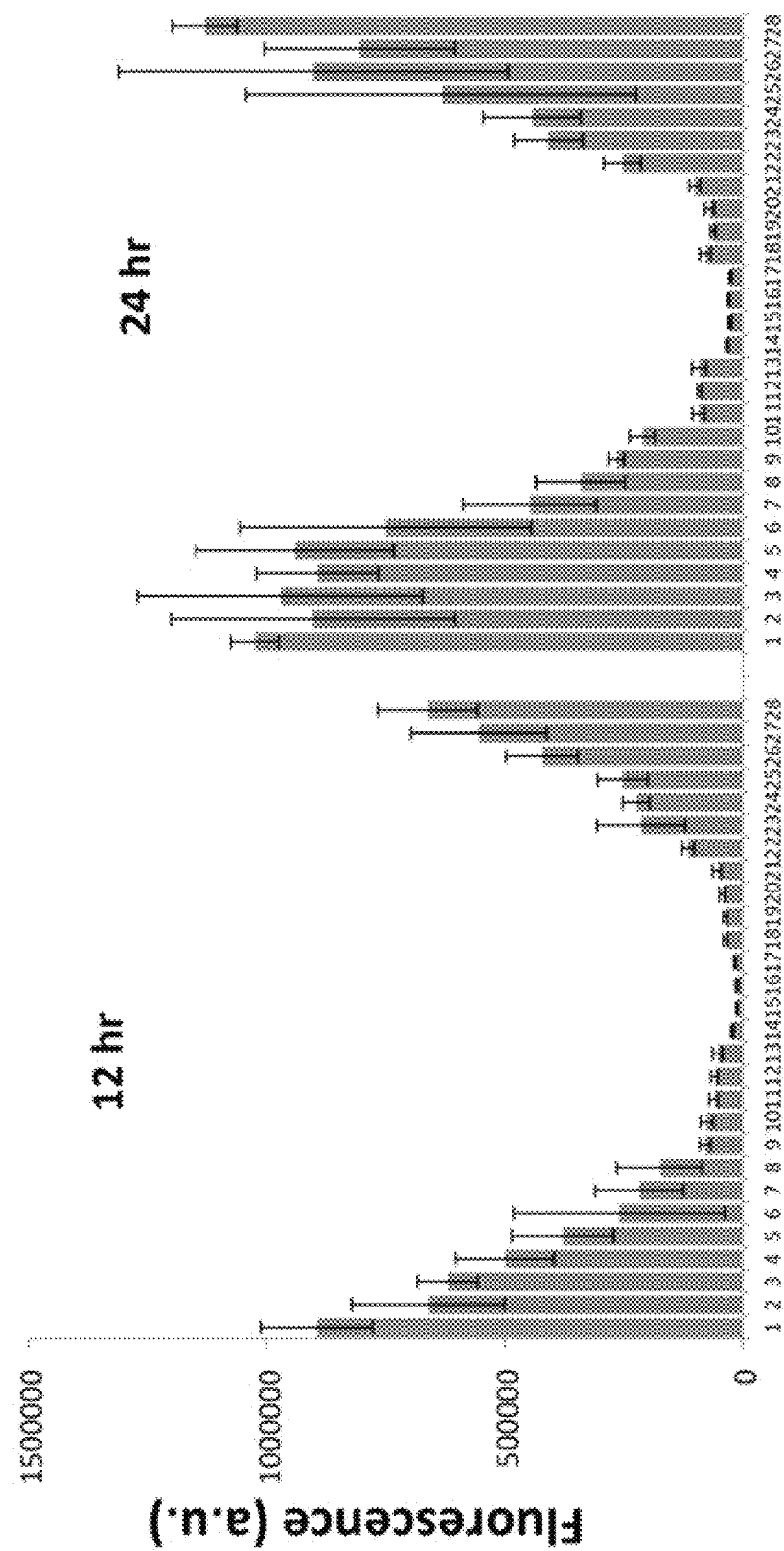

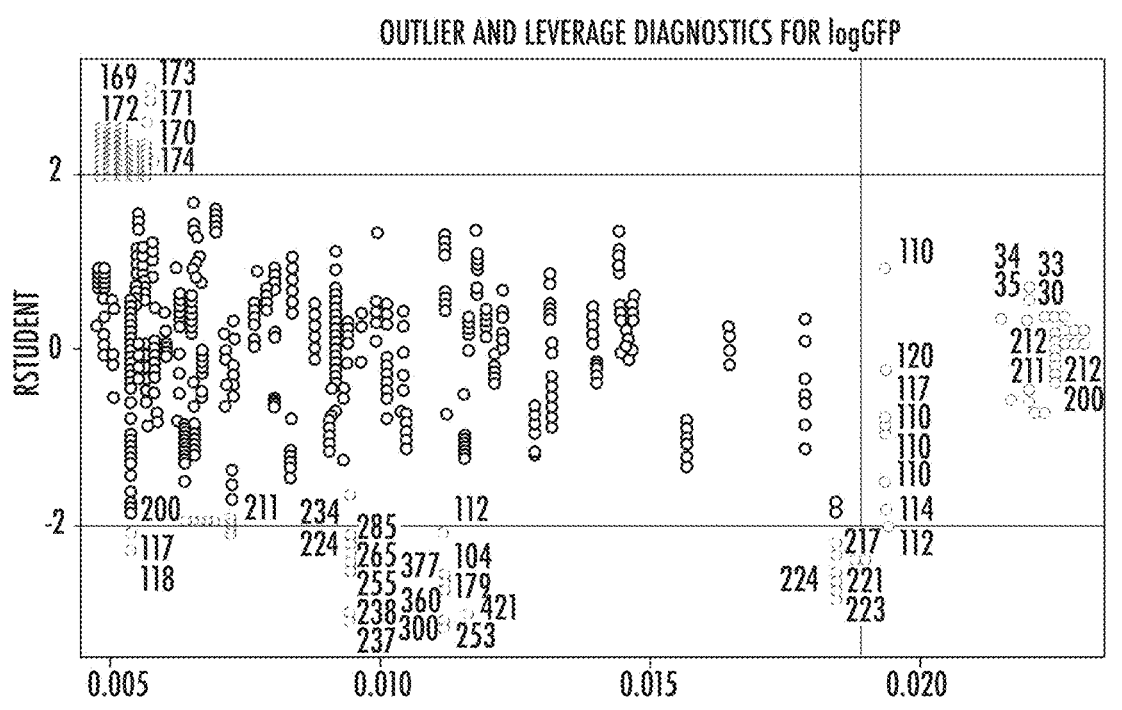
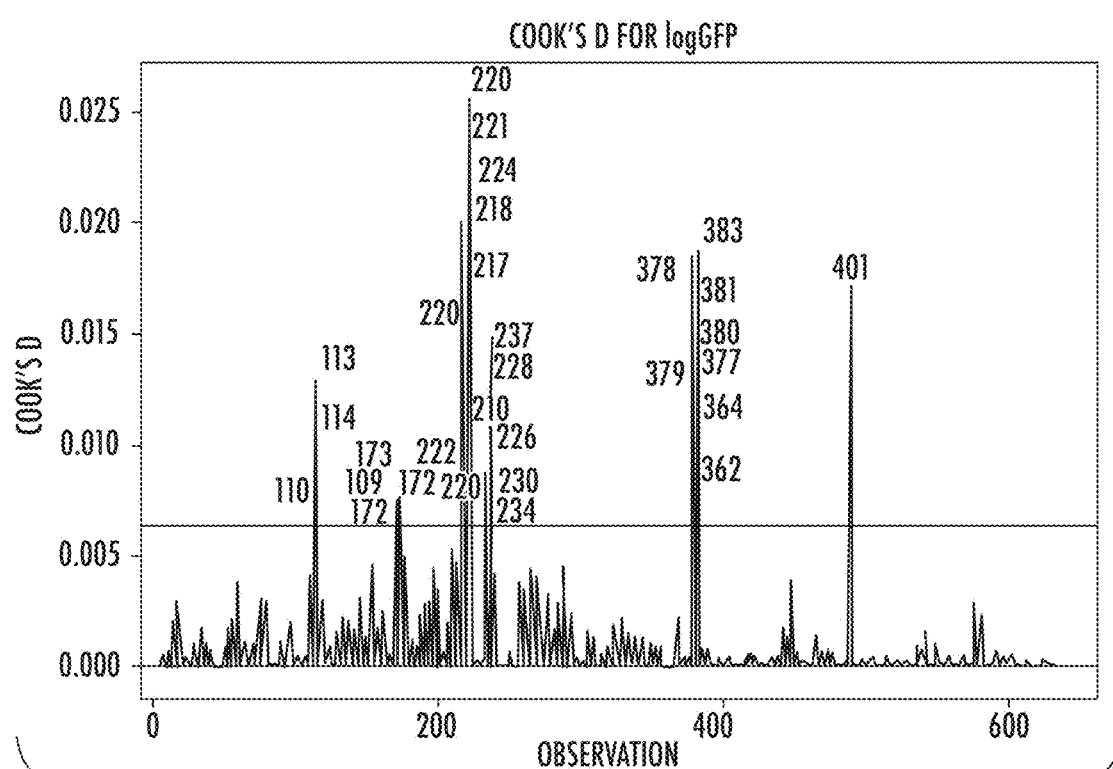
Fig. 9D

METHODS AND SYSTEMS FOR QUANTIFYING GENE EXPRESSION IN SYNTHETIC GENE CIRCUITS AND FOR TUNING SYNTHETIC GENE CIRCUITS

RELATED APPLICATIONS

This application claims the benefit of and priority to U.S. Provisional Application No. 62/617,584, filed Jan. 15, 2018, the contents of which are incorporated herein by reference in its entirety.

STATEMENT REGARDING FEDERALLY SPONSORED RESEARCH

This invention was made with government support under ROI GM1.06081 awarded by the National institutes of Health and DMS1100309 awarded by the National Science Foundation. The government has certain tights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 1,537 byte ASCI (text) file named "SegList" created on Feb. 11, 2019.

TECHNICAL FIELD

The present disclosure relates to a comprehensive model and gene expression metric that determines and tunes the gene expression of complex synthetic gene circuits.

BACKGROUND

Synthetic gene circuit engineering, as a foundational technology, has help start the burgeoning development of bacterial synthetic biology. Based on a large collection of well-characterized biological components including promoters, ribosome binding sites, transcriptional factors, terminators, RNA elements, and other small modules, complex gene circuits with designed functions can be wired using established biological principles. Toggle switches and repressilators are two of the earliest examples of engineered gene circuits (Elowitz and Leibler, 2000; Gardner et al., 2000). Presently, gene circuits are being designed for a wide range of applications, including spatial pattern formation (Cao et at, 2016; Liu et al., 2011), drug development (Smanski et al., 2016; Wright, 2014), pathogen detection (Pardee et al., 2014, 2016), in vivo delivery (Din et al., 2016), and other biotechnological applications including nitrogen fixation (Mus et al., 2016; Wu and Wang, 2015) and environmental bioremediation (Zhang and Nielsen, 2014).

Currently, circuit assembly has two main approaches: one is monocistronic construction, in which one promoter drives one gene expression and ensures each gene is being expressed independently; the other is polycistronic construction, in which one promoter transcribes multiple genes (an operon) into a single messenger RNA but is translated into individual products (FIG. 1A). An operon, a cluster of genes with functional associations under control of a single promoter, is a common type of genome organization in prokaryotic cells and also widely found in eukaryotes and viruses (Rocha, 2008).

The operon, as an organization strategy, refers mainly to the genes' order and position downstream of the promoter to ensure a coordinated gene expression and regulation, and enable bacteria cells to rapidly respond to environmental changes. In synthetic biology, this organization (synthetic operon) facilitates rapid constructions of genetic cascades and decreases the number of biological components (such as the promoters and terminators) required for complex genetic circuits, and therefore is widely used in circuit engineering (Ma et al., 2016; Lee et al., 2016; Farasat et al., 2014; Cameron and Collins, 2014; Prindle et al., 2014; Yang et al., 2014; Litcofsky et al., 2012; Wu et al., 2017).

However, it remains unknown whether gene expression is impacted by immediately adjacent genes in a polycistronic operon and, if impacted, how the gene expression is changed. Two previous reports have indicated that gene position and transcriptional distance can affect gene expression in a synthetic operon (Chizzolini et al., 2014; Lim et al., 2011). However, the effects of adjacent genes in synthetic operons on the circuit's gene expression, dynamics, and functionality has not been systematically studied. These effects are more prominent for synthetic operons containing a cluster of genes and complex multi-layered genetic circuits.

Because of this uncertainty, the effects of immediately adjacent genes has been generally been neglected during engineering of synthetic gene networks, leading to unexpected circuit performance or failure (Brophy and Voigt, 2016; Carr et al., 2017; Veung et al., 2017). As a consequence, conventional methods for circuit design and assembly rely heavily on trial and error, making the process slow and inefficient, particularly in light of the effort required to produce and test each iteration.

SUMMARY

According to one aspect, a method of tuning the performance of a synthetic gene circuit comprising an operon having a plurality of genes includes quantifying, for each gene of the plurality of genes, a relative gene expression metric. The relative gene expression metric of the gene is quantified by determining a number (i) of nucleotides in a 5' adjacent transcriptional region (ATR) of the gene, determining a number (j) of nucleotides in a 3' ATR of the gene, determining a minimum free energy ($\Delta G_{-70 \rightarrow +38}$) of a mRNA secondary structure around a ribosome binding site (RBS) of the gene, determining a total folding energy ($\Delta G_{5'ATR}$) for the 5' ATR of the gene, and determining a folding energy ($\Delta G_{3'ATR\_100}$) for the first 100 nucleotides of the 3' ATR of the gene. The relative gene expression metric of the gene is then calculated by summing sequence-dependent energy changes. The sum includes $\beta 0 + \beta 1 \cdot \Delta G_{5'ATR} + \beta 2 \cdot \Delta G_{3'ATR\_100} + \beta 3 \cdot i \cdot Gm + j \cdot Gm + \beta 5 \cdot \Delta G_{-70 \rightarrow +38}$, where $\beta 1$, $\beta 2$, $\beta 3$, $\beta 4$, and $\beta 5$ are scaling coefficients, and Gm represents is an average energy cost for synthesizing a nucleotide. The method further includes evaluating the performance of the synthetic gene circuit by simulating, through applying the relative gene expression metrics of the plurality of genes to a deterministic model, the performance of an intended function of the synthetic gene circuit, and finally assembling the synthetic gene circuit.

Particular embodiments may comprise one or more of the following features. The intended function may be an AND logic gate, and/or the deterministic model may apply the relative gene expression metrics to an ordinary differential equation model. The intended function may be a bistable toggle switch, and/or the deterministic model may include bifurcation analysis of the relative gene expression metrics. The number (i) of nucleotides may be between 299 and 2001 nucleotides. The 5' ATR and/or the 3' ATR may have GC contents ranging from 28% to 66%. The plurality of genes may be two or three genes.

According to another aspect of the disclosure, a method of tuning the performance of a synthetic gene circuit comprising an operon having a plurality of genes includes quantifying, for each gene of the plurality of genes, a relative gene expression metric. The relative gene expression metric of the gene is quantified by determining a number (i) of nucleotides in a 5' adjacent transcriptional region (ATR) of the gene, determining a number (j) of nucleotides in a 3' ATR of the gene, determining a minimum free energy ($\Delta G_{-70-+38}$) of a mRNA secondary structure around a ribosome binding site (RBS) of the gene, determining a total folding energy ($\Delta G_{5'ATR}$) for the 5' ATR of the gene, and determining a folding energy ($\Delta G_{3'ATR\_100}$) for the first 100 nucleotides of the 3' ATR of the gene. The relative gene expression metric of the gene is then calculated by summing sequence-dependent energy changes. The sum includes $\beta 0+\beta 1 \cdot \Delta G_{5'ATR}+\beta 2 \cdot \Delta G_{3'ATR\_100}+\mu 3 \cdot i \cdot Gm+\beta 4 \cdot j \cdot Gm+\beta 5 \cdot \Delta G_{-70-+38}$, where $\beta 1$, $\beta 2$, $\beta 3$, $\beta 4$, and $\beta 5$ are scaling coefficients, and Gm represents is an average energy cost for synthesizing a nucleotide. The method further includes evaluating the performance of the synthetic gene circuit by simulating, using the relative gene expression metrics of the plurality of genes, the performance of an intended function of the synthetic gene circuit, and assembling the synthetic gene circuit.

Particular embodiments may comprise one or more of the following features. The intended function may be a logic gate. Simulating the performance of the intended function may include applying the relative gene expression metrics of the plurality of genes to an ordinary differential equation model. The intended function may be a bistable toggle switch. Simulating the performance of the intended function may include performing a bifurcation analysis of the relative gene expression metrics of the plurality of genes.

According to yet another aspect of the disclosure, a method of tuning the performance of a synthetic gene circuit comprising an operon having a plurality of genes includes quantifying, for each gene of the plurality of genes, a relative gene expression metric. The relative gene expression metric of the gene is quantified by determining a number (i) of nucleotides in a 5' adjacent transcriptional region (ATR) of the gene, determining a number (j) of nucleotides in a 3' ATR of the gene, determining a minimum free energy ($\Delta G_{-70-+38}$) of a mRNA secondary structure around a ribosome binding site (RBS) of the gene, determining a total folding energy ($\Delta G_{5'ATR}$) for the 5' ATR of the gene, and determining a folding energy ($\Delta G_{3'ATR\_100}$) for the first 100 nucleotides of the 3' ATR of the gene. The relative gene expression metric of the gene is then calculated by summing sequence-dependent energy changes. The sum includes $\beta 0+\beta 1 \cdot \Delta G_{5'ATR}+\beta 2 \cdot \Delta G_{3'ATR\_100}+\beta 3 \cdot i \cdot Gm+\beta 4 \cdot j \cdot Gm+\beta 5 \cdot \Delta G_{-70-+38}$, where $\beta 1$, $\beta 2$, $\beta 3$, $\beta 4$, and $\beta 5$ are scaling coefficients, and Gm represents is an average energy cost for synthesizing a nucleotide. The method also includes evaluating the performance of the synthetic gene circuit by simulating, using the relative gene expression metrics of the plurality of genes, the performance of an intended function of the synthetic gene circuit.

Particular embodiments may comprise one or more of the following features. Simulating the performance of the intended function may include applying the relative gene expression metrics of the plurality of genes to a deterministic model. The deterministic model may be an ordinary differential equation model. The intended function may be one of a logic gate, a multistable toggle switch, and an oscillator. Lastly, the method may further include assembling the synthetic gene circuit.

Aspects and applications of the disclosure presented here are described below in the drawings and detailed description. Unless specifically noted, it is intended that the words and phrases in the specification and the claims be given their plain, ordinary-, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent-such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

The use of the words "function," "means" or "step" in the Detailed Description or Description of the Drawings or claims is not intended to somehow indicate a desire to invoke the special provisions of 35 U.S.C. § 112(f), to define the technology. To the contrary, if the provisions of 35 U.S.C. § 112(f) are sought to be invoked to define the technology, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

DESCRIPTION OF THE FIGURES

FIG. 1A is an illustration of the operon structure and genes expression. The three structural genes are transcribed as a polycistronic mRNA, but translated into individual proteins, P: promoter, O: operator. Oval: ribosome. The top portion of FIG. 1B is schematic representation of synthetic bi-cistronic gene circuits with gene X and GFP. Grey arrow: constitutive promoter; Oval: ribosome binding site; Hexagon: transcriptional terminator. The bottom portion of FIG. 1B depicts flow cytometry results that show GFP expression is influenced by its 5'ATRs. X represents a gene name (i.e. LuxI, AraC, TetR, RhIR, and dnMyD88). "Control" is without X gene in the circuit. Rectangles in different shades represent different genes. X represents different gene names used in the circuit. Data represent, the mean±s.e. of eight, replicates. FIG. 1C shows the relative GFP mRNA concentrations (normalized to 16S rRNA control) for the circuits in FIG. 1B determined by RT-qPCR. Primer pair P1:P2 was designed to amplify GFP gene from the sample cDNA, The top portion of FIG. 1D is a schematic representation of synthetic bi-cistronic gene circuits with gene X and GFP, but with switched positions in the circuit. Gene position in the operon impacts GFP expression. Data represent the mean±s.d. of eight replicates. *P<0.05, P<0.001 and *P<0.0001 by student's t-test.

FIG. 2A shows analysis of a circuit design where GFP is arranged distal to the promoter. The top portion shows a schematic representation of synthetic polycistronic gene circuits X-GFP. X and Y represent different gene names. The bottom portion show's the regression results of 35 genetic circuits with one or two genes placed in front of GFP, which are labeled with different symbols. The lines are the linear regression results from the data. GFP expression is significantly impacted by its 5'ATRs' GC content, size and local folding free energy. Error bars are s.d. of eight measurements performed in three different days. Coefficients with standard error and equations can be found in Table 6. FIG. 2B shows analysis of a circuit design where GFP is placed in the middle of the three-gene operons (X-GFP-Y). GFP expression is significantly correlated with its 5' and 3' ATRs' GC content and local folding free energy. 20 circuits with different X and Y gene combinations were constructed. FIG. 2C show's analysis of a circuit design where GFP is placed proximal to the promoter (GFP-X). GFP expression is significantly impacted by its 3'ATRs' GC content and size. 24 circuits with different 3'ATRs were constructed, and different symbols are used to indicate bi- or tri-cistronic constructs in the regression results. FIG. 2D depicts investigation of non-coding ATR's regulation on GFP expression. In the scenario shown in the top portion of FIG. 2D, the X gene would not be expressed owing to a lack of RBS. GFP expression is significantly correlated with 5'ATRs' GC content, size and local folding free energy. Twenty-nine circuits with different X genes were constructed. FIG. 2E depicts a comprehensive model for ATR regulation on protein expression. The top portion shows co-transcriptional translation and degradation. After RBS is transcribed, RNase and ribosome competitively bind to mRNA to initiate translation or degradation. Generally, gene expression is influenced by overall stability and local secondary structure. The bottom portion is an illustration of the five variables in the model: $\Delta G_{5'ATR}$, $\Delta G_{3'ATR\_100}$, $\Delta G_{-70 \rightarrow +38}$, and transcriptional size (i, j). The numbers −70 and +38 identify the position of start codon (AUG) of interested gene. FIG. 2F plots experimentally observed GFP expressions against the coding-ATR model predicted GFP values with the five statistically significant energetic terms and fitted coefficients. If the model predicted values and experimentally observed values agreed perfectly ($R^2=100\%$), all the data points would fall on the dotted diagonal line of the squares. N is the total measurements for the 79 circuits. In the left portion, the three differently shaded dots indicate the data source from the three scenarios in FIGS. 2A-2C. The right portion plots experimentally measured GFP fluorescence against the non-coding ATR model predicted GFP expression with the three statistically significant energetic terms ($\Delta G_{5'ATR}$, i, and $\Delta G_{-70 \rightarrow +38}$).

FIGS. 3A-3D depict, in accordance with certain embodiments, a model guided circuit design for synthetic logic gates. FIG. 3A shows two designs for pLux/tet-AND logic gate. A constitutive promoter (left most long arrow) drives LuxR and TetR expression. pLux/tet is highly activated in presence of both AHL and aTc. LT and TL represent the order of LuxR and TetR positions in the operon. LuxR can bind with AHL to activate pLux/tet promoter (right most long arrow), while aTc can block the TetR inhibition to pLux/tet promoter. Lines with arrowheads indicate activation, and lines with T-bars indicate inhibition. FIG. 3B depicts dose responsive curves for different concentrations of AHL and aTc. The lines are from ODE model simulations based on the calculated relative changes of LuxR and TetR concentrations in LT and TL from our linear comprehensive model. Data points with error bar are experimental results, showing good match with model predictions. Inserted diagram is the basal expression of GFP for design LT and TL. The curves are inductions with different aTc concentrations (20 ng/ml, 100 ng/ml, and 200 ng/ml). FIG. 3C show's two designs for pLux/lac-AND logic gate. A constitutive promoter drives LuxR and LacI expression. pLux/lac (right most long arrow) is highly activated in presence of both AHL and IPTG (hexagon). LuxR can bind with AHL to activate pLux/lac promoter, while IPTG can block the LacI inhibition to pLux/lac promoter. LI and IL represent the order of LuxR and LacI positions in the operon. FIG. 3D depicts dose responsive curves for different concentrations of AHL and IPTG. The lines are model simulations based on the calculated relative changes of LuxR and LacI concentrations in LI and IL from our linear comprehensive model. Experimental results (data point with error bar) show a good match with model predictions. The curves are inductions with different IPTG concentrations (1 µM, 10 µM and 100 µM). Inserted diagram is the basal expression of GFP for design LI and IL. Data represent the mean±s.e. of three replicates, p-value is calculated from student's t-test.

FIGS. 4A-4D depict, in accordance with certain embodiments, the results from tuning gene expression with synthetic 5' adjacent transcriptional regions. FIG. 4A shows the results of using synthetic 5'ATRs (SynF) to tune GFP expression for circuit CP-LuxR-GFP. ATRs having 200 bp in length were inserted between LuxR and GFP genes to tune GFP expression, and the control (Ctl) is a construct without, the ATR insert. Flow cytometry results indicate that GFP fluorescence increases with gradually increasing 5'ATRs GC content from 28% to 54%. FIG. 4B depicts the microscopic results of GFP fluorescence for the constructs in FIG. 4A. Scale bar: 5 µm. Magnification: 40×. FIG. 4C show's the results of using synthetic 5'ATRs (SynF) with different GC content to tune GFP expression for circuit CP-GFP. All of the SynF have the same size (200 bp) and are inserted upstream of GFP gene (Top). Flow cytometry results of GFP fluorescence for 5'ATRs with GC content from 28% to 67% (Bottom). FIG. 4D compares circuits with different 5'ATR sizes (through shortening and adding a common sequence S44, GC: 44%, Size: 200 bp) that were constructed to tune GFP expression. Flow cytometry results show that GFP fluorescence intensity gradually decreases with increasing 5' ATR sizes.

FIGS. 5A-5F show, in accordance with certain embodiments, the use of synthetic ATRs to modulate bistability of toggle switches. The left portion of FIG. 5A depicts an abstract diagram of toggle switch topology, where X and Y mutually inhibit, each other. The right portion of FIG. 5A depicts the molecular implementation of the toggle switch. Lad inhibits TetR by binding the pLae promoter while TetR binds pTet to block Lad expression, forming a mutually inhibitory network. Inducers IPTG and aTc (hexagon) can respectively relieve Lad and TetR inhibition. GFP serves as the readout of pTet promoter. Synthetic ATRs (SynF) were arranged right, upstream of TetR gene. FIG. 5B depicts the initial steady states for the three toggles. Toggle without ATR insertion (T_WT) show's bimodal distribution (GFP-OFF and GFP-ON), while T_S28 (ATR with 28% GC content, 200 bp) shows higher GFP expression and T_S67 (ATR with 67% GC content, 200 bp) shows lower GFP expression than the GFP-ON population of T_WT. FIG. 5C depicts the bifurcation analysis for GFP (LacI) expression with different TetR production rates under induction of varying concentrations of aTc. A low production rate for TetR, corresponding to T_S28, has the smallest bistable region, while a high rate (corresponding to T_WT) has the broadest bistable region. The range of stable steady-state solutions are below about 1.3 and above 10 along the y-axis (GFP*, computed GFP abundance from the model) and the range of unstable steady-state solutions span 1.3 and 10 along the y-axis. FIGS. 5D-5F depict the hysteresis results for toggles T_S28, T_S67 and T_WT under induction of varying concentrations of aTc. Black lines indicate the initial OFF cells with basal GFP expression while gray lines indicate the initial ON cells with high GFP expression. Data represent the mean±s.d. of three replicates. Grey area is the presumable bistable region for each circuit.

FIGS. 6A-6G depict in accordance with certain embodiments, the RT-qPCR result for the circuits in FIG. 1B, and gene position in the tri-cistronic circuit impacts GFP expression (related to FIG. 1A-1D). FIG. 6A show's the two pairs of primers (P1:P2, and P3:P4) designed to amplify GFP gene from the sample cDNA, The binding sites of the four primers are also indicated. FIG. 6B depicts the RT-qPCR result using primer pair P3:P4 to amplify GFP gene. The GFP mRNA concentrations were normalized to the 16S rRNA control. Error bar represents standard deviation of three biological replicates. FIG. 6C depicts the correlation between the GFP fluorescence intensities and the relative GFP mRNA concentrations. Little correlation was found using primer pair P1:P2 or P3:P4. These results indicate there is little correlation between GFP protein fluorescence intensity and mRNA level for the circuits in FIG. 1B. FIG. 6D the results where GFP is arranged at proximal (P1) or middle (P2) or distal (P3) positions to the constitute promoter in the tri-cistronic circuit with two more genes LuxR and RhlR. Circuit with GFP at P1 position show's the highest GFP expression. FIG. 6E shows the results where GFP is arranged at P1, P2, and P3 positions in the tri-cistronic circuit with genes LuxR and AraC. Circuit with GFP at P3 position shows the highest GFP expression. FIG. 6F shows the results where GFP is arranged at P1, P2, and P3 positions in the tri-cistronic circuit with two copies of LuxR genes. Circuit with GFP at P1 position shows the highest GFP expression. FIG. 6G shows the results where GFP is arranged at P1, P2, P3 positions to the constitute promoter in the tri-cistronic circuit with genes LuxR and Lad. Circuit with GFP at P3 position show's the highest GFP expression. Data represent the standard deviation of eight replicates. Arrow: constitutive promoter; Oval: ribosome binding site; Hexagon: transcriptional terminator. Differently shaded rectangles represent different genes.

FIGS. 7A-7D depict, in accordance with certain embodiments, the sliding window analysis for local GC content and model fitting; and gene expression comparison for circuits with and without ribosome binding sites (Related to FIG. 2A-2F). The top portion of FIG. 7A depicts the schematic representation of constructs with GFP distal to the constitutive promoter. The lines with arrows indicate 5'ATRs with different, lengths. The bottom portion of FIG. 7A depicts calculation of the GC content of 5'ATRs with different lengths from 400 nucleotides to the whole transcriptional region and their fit to the model. The coefficients of determination ($R^2$) are compared to 5'ATRs with different lengths. Linear model results show that GC content with the whole 5'ATR has the highest, fitting efficiency. X represents different genes used in the circuit. The top portion of FIG. 7B depicts the schematic representation of constructs with GFP proximal to the constitutive promoter. The lines with arrows indicate 3'ATRs with different lengths. The bottom portion of FIG. 7B depicts the calculation of the GC content of 3'ATRs with different lengths from 50 nucleotides to the whole transcriptional region are calculated and their fit to the model. The coefficients of determination ($R^2$) are compared to 3'ATRs with different lengths. Model fitting results show that GC content of the first 100 nucleotides 3'ATR has the highest fitting efficiency. The top portion of FIG. 7C depicts the schematic representations of synthetic gene circuits with RBS or without RBS. Three fluorescent proteins GFP, enhanced yellow fluorescent protein (EYFP), and enhanced cyan fluorescent protein (ECFP) were chosen. The results in the bottom portion of FIG. 7C indicate that there are minimal fluorescence expressions for all the three circuits without RBS, The smaller rectangle represents fluorescent genes (Fluo.). Cyan fluorescence was measured by plate reader (excitation: 405 nm; emission: 485 nm). Experimental data, are replicated three times with total twelve data points, and bars represent the standard deviation of the mean. FIG. 7D depicts the schematic representations of synthetic bi-cistronic gene circuits. GFP reporter was expressed downstream of a coding ATR (with RBS) or noncoding ATR (without RBS), respectively. Higher GFP expression was observed for circuits with the same genes (TetR, or Lad, or LuxR, or cI, or LuxI, or AraC) with RBS than those without RBS. Fluorescence was measured by flow cytometry. Furor bar represents standard deviation of eight biological replicates. Arrow: constitutive promoter; Oval: ribosome binding site, Hexagon: transcriptional terminator.

FIG. 8A depicts the dose responsive curves for different concentrations of AHL and aTc. The solid lines are from ODE model simulations based on the calculated relative changes of LuxR and TetR concentrations in LT and TL from our linear comprehensive model. Data points with error bar are experimental results, showing good match with model predictions. The curved lines are inductions with different aTc concentrations (0 ng/ml, 0.2 ng/ml, and 2 ng/ml). Data represent the mean±s.d. of three replicates. FIG. 8B depicts the dose responsive curves for different concentrations of AHL and IPTG. The solid lines are model simulations based on the calculated relative changes of LuxR and LacI concentrations in LI and IL from our linear comprehensive model. Experimental results (data point with error bar) show good match with model predictions. The curved lines are inductions with different IPTG concentrations (0, 0.1 µM, 200 µM and 400 µM). Data represent the mean±s.d. of three replicates. The left portion of FIG. 8C depicts the model predicted GFP expression under regulation of synthetic fragments with constant size but varying GC content from 28% to 66%. GFP predictions (mean and standard deviation) were calculated by XLSTAT based on the comprehensive non-coding ATR model (FIG. 2F). The right portion of FIG. 8C depicts the model predicted GFP expression under regulation of synthetic fragments with constant GC content but varying sizes from 50 bp to 4600 bp. FIG. 8D depicts refined non-coding ATR model with the data in FIGS. 4B and 4D. The total data points (N) is 576 (266 from FIG. 2B; 190 from FIG. 4B; and 120 from FIG. 4D). The refined model coefficients can be found in Table 4. FIG. 8E show that α1 and α2 are the production rates of LuxR and TetR protein, respectively. Three scenarios with different values of α1 and α2 are plotted. When α1>α2, more LuxR protein is produced, resulting in higher GFP expression. When α1<α2, more TetR protein is produced, leading to lower GFP expression. Through tuning the relative size of α1 and α2, we can predict GFP dynamics under induction of AHL and aTc. More detail about the model construction can be found in STAR Methods.

FIGS. 9A-9D depict, in accordance with certain embodiments, GFP expression at 12 and 24 hours; cell growth rates and fluorescence measurement by plate reader for different circuits with X-GFP organization; and fit diagnostics for the comprehensive coding-ATR model (Related to STAR Methods). FIG. 9A depicts the GFP fluorescence of 28 gene circuits in FIGS. 2A-2F plotted at 12 and 24 hr. Similar fluorescence expression pattern was observed at 12 and 24 hr, and fluorescence was stronger at 24 hr. For stable protein expression, only 24 hr data are shown in this work, unless specified. FIG. 9B depicts the ten different gene circuits with different fluorescence expression levels (high, medium and low) are selected to test their growth rates under the same condition. The top portion depicts cell growth curves. All the samples reached the stationary phase after ~12 hr. The bottom portion depicts the time course of the fluorescence for the ten selected circuits. Fluorescence becomes stable before 16 hr. Although the gene expression in the circuit influenced the time of cells going to the exponential phase, all the samples went to stationary phase with similar optical density (QD) value after ~12 hours. Cells with J45014 circuit reach steady-state OD about 4 hours earlier than cells with C0161, while both of them show similar GFP expression levels. On the other hand, cells with C0012 circuit and cells with C0161 arrive stationary phase almost simultaneously, however, their GFP expression is remarkably different. These results suggest that the time to reach steady-state OD for each strain has little explanatory effect on the fluorescence differences. OD and fluorescence were measured by plate reader with 96-well plates. Data indicates mean±SD of three independent replicates. FIG. 9C depicts the fit diagnostics of the comprehensive coding-ATR model in FIG. 2F. The Predicted Value-Residual plot indicates that there is no apparent trend for the residuals, and the data is roughly normally distributed (Quantile-Residual plot and histogram), and the variables in the model explain most variation in the response variable from the residual-fit result (Fit-Mean and Residual). Leverage-R Student plot and Cook's D value indicate there are some outliers and high-leverage observations, which may influence the model. Overall, the generated model has a good fitting of the experimental data. FIG. 9D depicts the outlier and leverage diagnostics for the response (GFP). High-leverage data points and outliers are labeled out. Of the outliers, most of them are corresponding to a specific circuit, such as outliers 217~224 corresponding to the tricistronic circuit (promoter-luxR-appY-GFP, has 8 data points). Observations with high leverage such as 505~512 are corresponding to the circuit promoter-GFP-Zif23_GCN4. Moreover, some outliers are also high-leverage observations, FIG. 10A depicts the linear plots for the scenario where GFP is arranged distal to the promoter (FIG. 2A). The top portion of FIG. 10A depicts the schematic representation of synthetic polycistronic gene circuits X-GFP. The bottom portion of FIG. 10A depicts the scatter plots of GFP and 5'ATR GC content, 5'ATR size, and Free energy. The dark line is the fitted regression result. Equation and $R^2$ are also displayed for each fit. FIG. 10B depicts the linear plots for the scenario where GFP is placed in the middle of the three-gene operons (FIG. 2B). The top portion of FIG. 10B depicts the schematic representation of synthetic polycistronic gene circuits X-GFP-Y. The bottom portion of FIG. 10B depicts the scatter plots of GFP and 5'ATR GC content, 3'ATR GC content, and Free energy. FIG. 10C depicts the linear plots for the scenario where GFP is placed proximal to the promoter (FIG. 2C). The top portion of FIG. 10C depicts the schematic representation of synthetic polycistronic gene circuits GFP-X. The bottom portion of FIG. 10C depicts the scatter plots of GFP and 3'ATR GC content, 3'ATR GC content (100 nt), and Free energy. N is the number of circuits. FIG. 10D depicts the Linear plots for non-coding ATRs results in FIG. 2D. The top portion of FIG. 10D depicts the schematic representation of synthetic polycistronic gene circuits with non-coding X genes (29 circuits in total). The bottom portion of FIG. 10D depicts the scatter plots of GFP and 5'ATR GC content, 5'ATR size, and Free energy. The dark line is the fitted regression result. Equation and $R^2$ are also displayed for each fit.

DETAILED DESCRIPTION

Figure 1A:
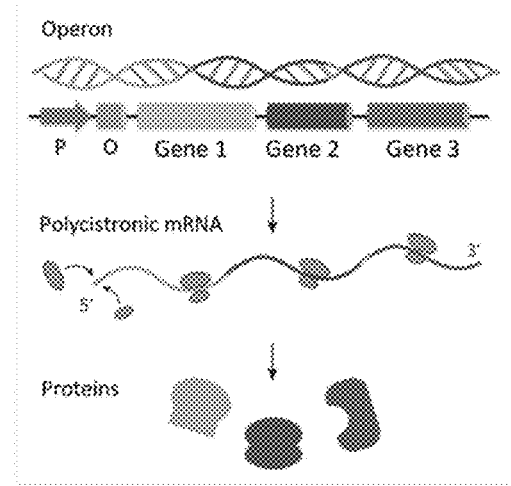
FIGS. 1A-1D show, in accordance with certain embodiments, that protein expression is significantly influenced by its adjacent genes and position in synthetic operons.
Figure 1C:
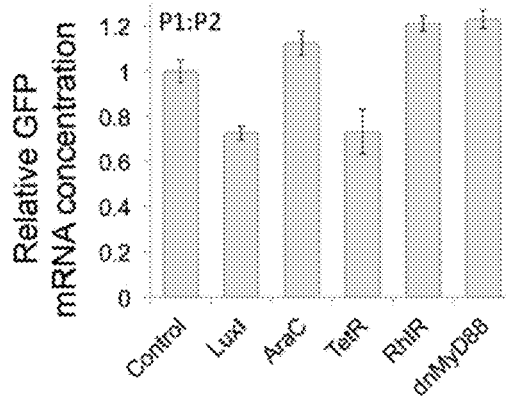

Detailed aspects and applications of the disclosure are described below in the drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that the present technology may be practiced without these specific details. It should be noted that there are many different and alternative configurations, devices and technologies to which the disclosed technologies may be applied. The full scope of the technology is not limited to the examples that are described below.

The singular forms "a," "an," and "the" include plural referents unless the context clearly dictates otherwise. Thus, for example, reference to "a step" includes reference to one or more of such steps.

A central goal of synthetic biology is to develop genetic circuits (also known as synthetic gene circuits) to program cell behaviors in a predictable way. With the increasing complexity of integrated multi-layer circuits, specific biocomponents' organization and circuitry structure design become extremely important for its functionality (Chen et al., 2015b; Nielsen et al., 2016; Wu et al., 2014). Contemplated herein are systems and methods directed to a much-needed quantitative metric that provides guidance to rational design and optimization of gene expression for large genetic circuits. Accordingly, this disclosure relates to solutions for facilitate the future engineering of more complex synthetic gene circuits.

Circuit engineering is the first step for synthetic biologists to achieve designed functionalities with synthetic gene circuits. A successful synthetic gene circuit depends on the full characterization of biological components and the emerged interactions between modules when assembled into a complete gene network (Bennett and Hasty, 2009, Brophy and Voigt, 2014; Nielsen et al., 2016; Wu et al. 2017). Development of a reliable tool to predict protein expression in the circuit has wide applications in biotechnology. For example, RBS Calculator is a well-developed design tool to predict and control translation initiation and protein expression in bacteria (Farasat et al., 2014; Sails et al., 2009).

Polycistronic architecture is common for synthetic gene circuits; however, it remains unknown how expression of one gene is affected by the presence of other genes/non-coding regions in the operon, termed adjacent transcriptional regions (ATR). Conventional methods for design and refinement of polycistronic gene circuits are slow and laborious. Each potential circuit architecture must be assembled, and then the resulting structure must be verified, and the functionality tested through gene expression. If the circuit does not perform well, or the intended functionality is not observed, modifications are made and the entire process begins again with a new architecture. Because there is so much uncertainty surrounding the effects of adjacent genes on gene expression, the process is mainly driven by trial and error, and often done multiple times for robustness. As gene circuits get more and more complicated, these conventional methods have greatly slowed down the process of designing and tuning new gene circuits.

Contemplated herein are systems and methods for quantifying the gene expression within a polycistronic operon using a relative gene expression metric calculated using a linear regression model, according to various embodiments. Advantageous over conventional methods, the methods taught herein allow for the evaluation of gene expression of genes within the operon, relative to each other, and thus a qualitative evaluation of the performance of the circuit for its intended function, with much less time and effort. The systems and methods taught herein allow for the design and tuning of synthetic gene circuits on time scales orders of magnitude shorter than conventional methods. Furthermore, these methods provide greater insight into why a circuit performs the way it does, not just a metric for how it performs. Thus, the systems and methods taught herein replaces the conventional trial and error methods for confirming the function of a synthetic gene circuit with a process that is more deliberate and guided.

To quantify ATRs effects on gene expression, a systematic analysis of the effect of adjacent genes and non-coding regions on green fluorescence protein (GFP) expression level through construction of ~120 synthetic gene circuits (operons) in *Escherichia coli* was performed. Synthetic operons were constructed with a reporter gene flanked by different ATRs and found that ATRs with high GC content, small size, and low folding energy lead to high gene expression. A model of gene expression was built based on these results. According to various embodiments, this model generates a relative gene expression metric (also referred to herein as a protein expression metric) that takes into account ATRs. This protein expression metric strongly correlates with ATR features including GC content, size, and the stability of mRNA folding near ribosomal binding site (RBS). This metric's utility in evaluating genes' relative expression levels is shown in the non-limiting Examples below, where the metric was incorporated in the design and construction of logic gates with lower basal expression and higher sensitivity and nonlinearity.

Specifically, through placing the GFP at different positions (proximal, middle, and distal) to the promoter, a new protein expression metric that takes into account the adjacent transcriptional regions' features including GC content, size and stability of mRNA folding near RBS was developed (FIGS. 2A-2F). The metric was established from about 120 gene circuits, which represents one of the largest databases of operon-based synthetic gene circuits in one study. This metric explains 63% and 67% of GFP variations in the coding ATR and non-coding ATR polycistronic gene circuits, respectively. Moreover, the results also demonstrated the metric's predictions of gene expression changes and induced nonlinear dynamic responses in different genetic contexts (FIGS. 3A-3D, 4A-4D, and 5A-5F), which suggest the model's utilities in guiding circuit design. Most ATRs' sizes in the circuits were 500-2000 bp, and the longest ATR is 2422 bp.

It is worth emphasizing that the results of this disclosure show the context-dependency of gene expression is not just limited to the RBS region but also including characteristics of the whole operon. This "global" effect in polycistronic operons is quantifiable, and explains nearly two-thirds of protein expression variations across all the synthetic gene circuits with different configurations. The quantitative relationship between adjacent transcriptional regions and gene expression regulation in polycistronic circuits helps to evaluate each gene's relative expression levels in a circuit and predict circuit outputs, which would save experimentalist's time and resources to screen and test modules' combinations, and thus greatly facilitate optimization of circuit design and accelerate the engineering of complex gene networks.

Consistent with previous results that gene position in operons can affect gene expression (Chizzolini et al., 2014; Lim et al., 2011), the results in the Examples further demonstrate that gene position (corresponding to ATR's change) significantly altered gene network dynamics including basal expression, system sensitivity, and nonlinearity, which has profound impacts for nonlinear dynamic systems. Such adjacent gene regulation effect has been generally neglected during construction of synthetic gene networks.

Although it is relatively well established that gene expression is influenced by the local context, holistic understanding of architectural rules governing polycistronic gene circuits remains largely unexplored. Compared to previous gene expression tuning strategies or insulation strategies, such as RBS calculator, bicistronic design with translation of a short leader peptide, or designed DNA sequence surrounding the start codon (mostly less than 100 bp) (Farasat et al, 2014; Ferreira et al, 2013; Li et al, 2017; Mutalik et al, 2013; Salis et al, 2009), the metric of the present disclosure places more emphasis on whether and how polycistronic operon organization (X-GFP, X-GFP-Y, and GFP-X) and different adjacent genes (size ranging from 313 to 2362 bp, and GC content ranging from 30.3% to 60.4%) impact protein expression in operon-based gene circuits. Furthermore, the present disclosure validated that the usage of designed synthetic DNA fragments with either different GC content (28%-67%) or sizes (50-4600 bp) as 5'ATRs to tune gene expression and modulate bistable regions of genetic toggle switches. The synthetic ATRs have a wide variable interval, therefore making it potentially applicable to a broad range of scientific and engineering tasks. Such a gene expression timing strategy also avoids the production of unwanted peptides, hence reduces potential metabolic burden. Additionally, in some embodiments, circuits having different ATRs impact the time of cells reaching stationary phase with similar optical density (FIG. 9B), which suggest that ATRs could be used as a means to 'program' the metabolic load and fitness of a cell simultaneously.

Thus, in certain implementations of the methods taught herein, the relative gene expression metric of the gene is quantified by determining a number (i) of nucleotides in a 5' adjacent transcriptional region (ATR) of the gene, determining a number (j) of nucleotides in a 3' ATR of the gene, determining a minimum free energy ($\Delta G_{-70-+38}$) of a mRNA secondary structure around a ribosome binding site (RBS) of the gene, determining a total folding energy ($\Delta G_{5'ATR}$) for the 5' ATR of the gene, and determining a folding energy ($\Delta G_{3'ATR\_100}$) for the first 100 nucleotides of the 3' ATR of the gene. The relative gene expression metric of the gene is then calculated by summing sequence-dependent energy changes. The sum includes $\beta 0+\beta 1 \cdot \Delta G_{5'ATR}+\beta 2 \cdot \Delta G_{3'ATR\_100}+\beta 3 \cdot i \cdot Gm+\beta 4 \cdot j \cdot Gm+\beta 5 \cdot \Delta G_{-70-+38}$, where $\beta 1$, $\beta 2$, $\beta 3$, $\beta 4$, and $\beta 5$ are scaling coefficients, and Gm represents is an average energy cost for synthesizing a nucleotide. The method further includes evaluating the performance of the synthetic gene circuit by simulating, through applying the relative gene expression metrics of the plurality of genes to a deterministic model, the performance of an intended function of the synthetic gene circuit, and finally assembling the synthetic gene circuit.

In accordance with other implementations of the disclosure, the method of tuning the performance of a synthetic gene circuit comprising an operon having a plurality of genes includes quantifying, for each gene of the plurality of genes, a relative gene expression metric. The relative gene expression metric of the gene is quantified by determining a number (i) of nucleotides in a 5' adjacent transcriptional region (ATR) of the gene, determining a number (j) of nucleotides in a 3' ATR of the gene, determining a minimum free energy ($\Delta G_{-70-+38}$) of a mRNA secondary structure around a ribosome binding site (RBS) of the gene, determining a total folding energy ($\Delta G_{5'ATR}$) for the 5' ATR of the gene, and determining a folding energy ($\Delta G_{3'ATR\_100}$) for the first 100 nucleotides of the 3' ATR of the gene. The relative gene expression metric of the gene is then calculated by summing sequence-dependent energy changes. The sum includes $\beta 0+\beta 1 \cdot \Delta G_{5'ATR}+\beta 2 \cdot \Delta G_{5'ATR\_100}+\beta 3 \cdot i \cdot Gm+\beta 4 \cdot j \cdot Gm+\beta 5 \cdot \Delta G_{-70-+38}$, where $\beta 1$, $\beta 2$, $\beta$, $\beta 4$, and $\beta 5$ are scaling coefficients, and Gm represents is an average energy cost for synthesizing a nucleotide. The method further includes evaluating the performance of the synthetic gene circuit by simulating, using the relative gene expression metrics of the plurality of genes, the performance of an intended function of the synthetic gene circuit, and assembling the synthetic gene circuit.

In accordance to yet another aspect of the disclosure, a method of tuning the performance of a synthetic gene circuit comprising an operon having a plurality of genes includes quantifying, for each gene of the plurality of genes, a relative gene expression metric. The relative gene expression metric of the gene is quantified by determining a number (i) of nucleotides in a 5' adjacent transcriptional region (ATR) of the gene, determining a number (j) of nucleotides in a 3' ATR of the gene, determining a minimum free energy ($\Delta G_{-70-+38}$) of a mRNA secondary structure around a ribosome binding site (RBS) of the gene, determining a total folding energy ($\Delta G_{5'ATR}$) for the 5' ATR of the gene, and determining a folding energy ($\Delta G_{3'ATR\_100}$) for the first 100 nucleotides of the 3' ATR of the gene. The relative gene expression metric of the gene is then calculated by summing sequence-dependent energy changes. The sum includes $\beta 0+\beta 1 \cdot \Delta G_{5'ATR}+\beta 2 \cdot \Delta G_{3'ATR\_100}+\beta 3 \cdot i \cdot Gm+\beta 4 \cdot j \cdot Gm+\beta 5 \cdot \Delta G_{-70-+38}$, where $\beta 1$, $\beta 2$, $\beta 3$, $\beta 4$, and $\beta 5$ are scaling coefficients, and Gm represents is an average energy cost for synthesizing a nucleotide. The method also includes evaluating the performance of the synthetic gene circuit by simulating, using the relative gene expression metrics of the plurality of genes, the performance of an intended function of the synthetic gene circuit.

Particular embodiments of the aforementioned implementations may comprise one or more of the following features. Simulating the performance of the intended function may include applying the relative gene expression metrics of the plurality of genes to a deterministic model. The deterministic model may be an ordinary differential equation model. The intended function may be one of a logic gate, a multi stable toggle switch, and an oscillator. Lastly, the method may further include assembling the synthetic gene circuit.

Some embodiments were applied to the tuning of a bistable gene network. Synthetic 5'ATRs were designed to tune protein expression levels over a 300-fold range. By combining ATR regulation and mathematical modeling, the synthetic ATRs can be used to quantitatively tune nonlinear dynamics of bistable gene networks, according to some embodiments. As shown in detail in the Examples below, the synthetic 5'ATRs are useful for building synthetic toggle swatches with varying basal expression and degrees of bistability.

In some embodiments, the methods disclosed herein may be implemented in a system comprising a computer. For example, in one embodiment, the determination of the five key terms of the model may be performed by the computer based upon user input and data retrieved from a storage or another computer system. In another embodiment, the computer may be given a superset of genes from which it constructs a plurality of subsets, varying composition and ordering within the operon, and quantify the relative gene expression for collection of subsets to find a gene circuit architecture that meets a predefined criteria. According to other embodiments, the methods discussed herein may be implemented in a gene circuit, design kit, made to facilitate the design and tuning of a particular type of gene circuit.

Illustrative, Non-Limiting Examples in Accordance with Certain Embodiments

The disclosure is further illustrated by the following examples that should not be construed as limiting. The contents of all references, patents, and published patent applications cited throughout this application, as well as the Figures, are incorporated herein by reference in their entirety for all purposes.

1. STAR Methods

Table 1 lists the key resources.

TABLE 1

| REAGENT or RESOURCE | SOURCE | IDENTIFIER |
|---|---|---|
| Bacterial and Virus Strains | | |
| E. coli DH10B | Invitrogen | Cat# 18297010 |
| E. coli MG1655 strain | James Collins laboratory (Litcofsky et al., 2012) | |
| E. coli MG1655 strain with lacI−/− | James Collins laboratory (Litcofsky et al., 2012) | |
| Chemicals, Peptides, and Recombinant Proteins | | |
| AHL (N-(β-Ketocaproyl)-L-homoserine lactone) | Sigma-Aldrich | Cat# 143537-62-6 |
| Isopropyl β-D-1-thiogalactopyranoside | Sigma-Aldrich | Cat# 367-93-1 |
| Anhydrotetracycline hydrochloride | Sigma-Aldrich | Cat# 13803-65-1 |
| Ampicillin sodium salt | Sigma-Aldrich | Cat# A9518 |
| Oligonucleotides | | |
| Primers for gene amplification | | |
| gBlocks for synthetic ATRs | | |
| Recombinant DNA | | |
| Plasmids with Biobricks parts | | |
| Plasmids with amplified transcriptional factors | | |
| Plasmids with synthetic ATRs | | |
| Software and Algorithms | | |
| MATLAB version R2014b | MathWorks | |
| SAS 9.4 | SAS Institute | |
| XLSTAT version 2017.4 | Addinsoft | |
| XPP AUTO 8.0 | University of Pittsburgh | |
| Deposited Data | | |
| Data generating the comprehensive biophysical models & code for the model simulation and statistical analysis | | |
| DNA sequence data for all the synthetic circuits | | |

1. Methods a. Plasmid Construction

Most genes were obtained from iGEM Registry These genes are often used in synthetic biology projects, including transcriptional factors, quorum-sensing components, and other functional genes. Plasmids were constructed using standard molecular biology techniques and all genetic circuits were assembled based on standardized BioBrick methods. As an example, construct Promoter-TetR-GFP is composed of five BioBrick standard biological parts: BBa_J23I04 (constitutive promoter, CP), BBa_B0034 (ribosome binding site, RBS), BBa_C0040 (tetR), BBa_E0040 (green fluorescent protein, GFP) and BBa_B0015 (transcriptional terminator). To produce RBS-TetK module, plasmid containing TetR was digested by XbaI and PstI as the insert fragment while RBS vector was cut by SpeI and PstI. Both fragment and vector were separated on 1% TAE agarose gel electrophoresis and purified using PureLink© gel extraction Kit (Invitrogen). Purified fragment and vector were then ligated by T4 DNA ligase (New England Biolabs, NEB). The ligation products were further transformed into E. coli DH10B and plated on LB agar plate with 100 µg/mi ampicillin for screening. Finally, plasmids extracted by Gen-Elute™ HP MiniPrep Kit (Sigma-Aldrich) were confirmed through gel electrophoresis (digested by EcoRI and PstI) and DNA Sequencing (Biodesign sequencing Lab, ASU). Similar steps were carried out for subsequent rounds of cloning to assemble the whole construct. All the circuits' DNA sequences are provided in the Table 10.

Figure 2A:
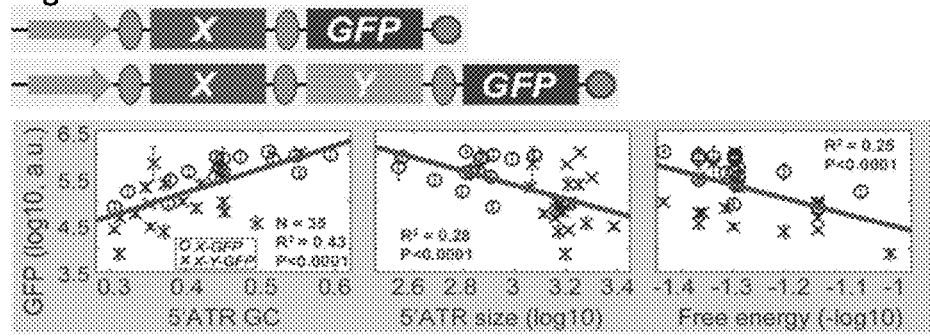
FIGS. 2A-2F depict, in accordance with certain embodiments, the quantitative characterization of adjacent gene regulation in synthetic operons.
Figure 2B:
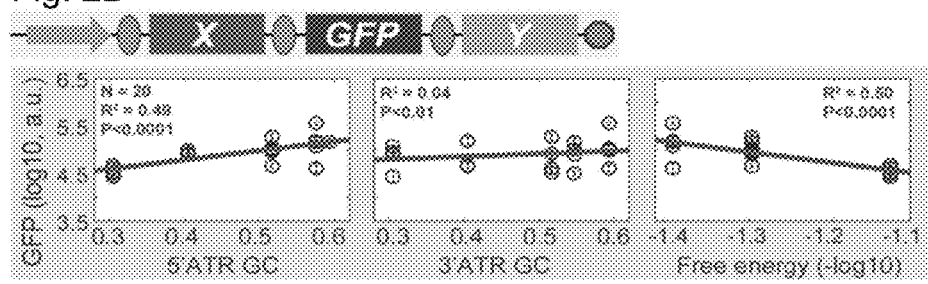
Figure 2C:
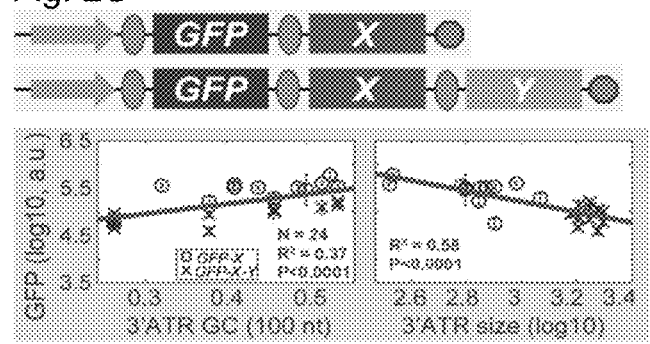
Figure 2D:
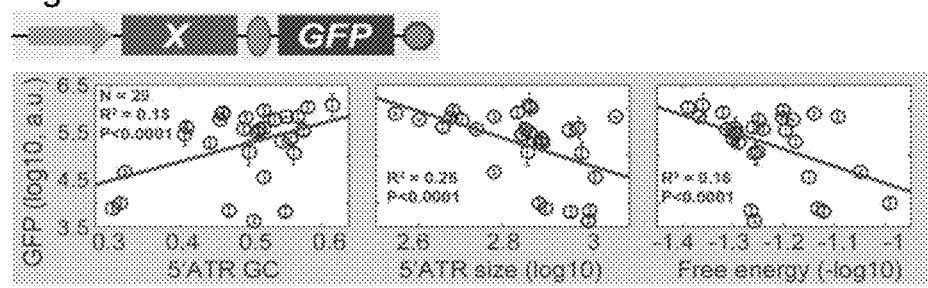
Figure 2E:
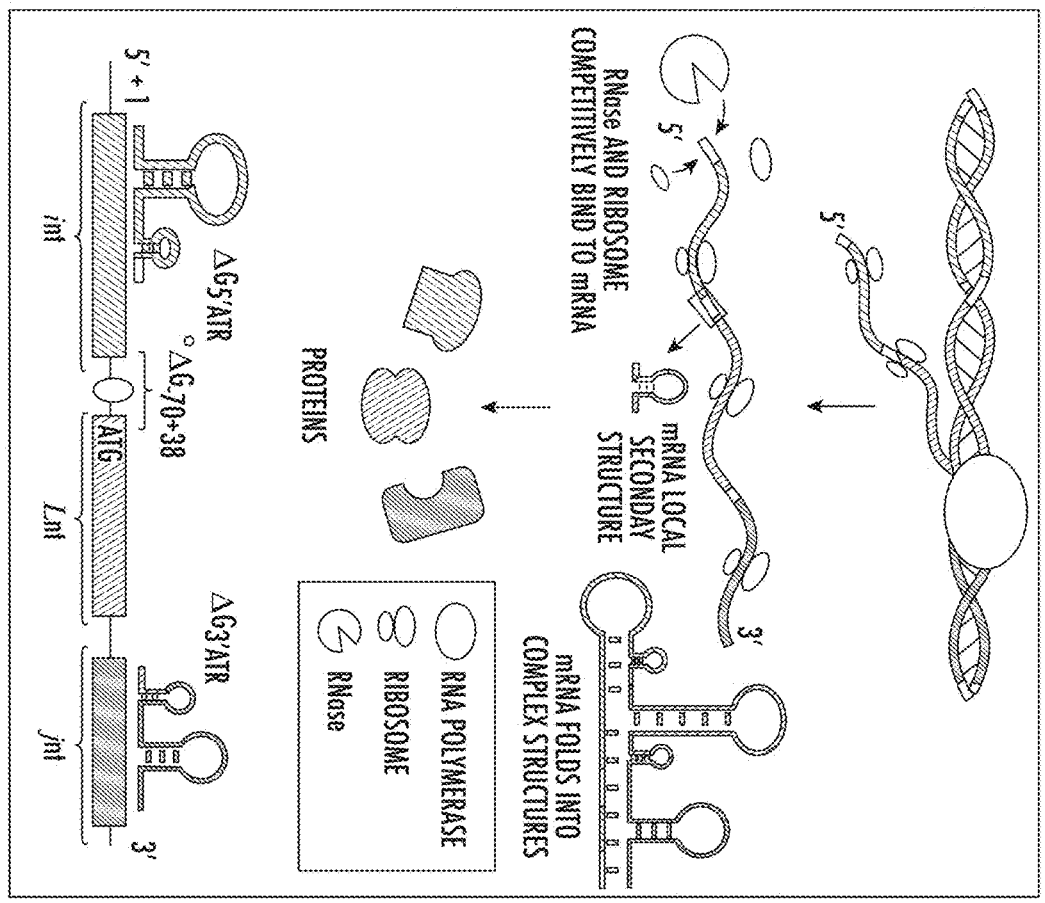

Also, 17 transcriptional factors with varying GC content and sizes used in FIG. 2D were amplified from the E. coli genome with designed primers. Synthetic sequences were randomly generated with the same length (200 bp) but various GC contents (28%-67%). Sequences with ribosome binding site-features (AGGAGG) were redesigned to exclude its translation potential. All synthetic sequences and primers were synthesized as custom DNA oligos or gBlocks gene fragments from Integrated DNA Technologies (IDT). In order to express consistently in the ceil, all constructs were finally subcloned into pSB1A3 vector prior to the test.

b. Minimum Free Energy Calculation

All minimum free energy (MFE) of mRNAs were computed on Nucleic Acid Package (NUPACK) web server (Zadeh et al., 2011). Specifically, we chose Serra and Turner parameter set as the RNA energy parameter and set 37° C. 1.0 M Na$^+$ and 0 M Mg$^{2+}$ to be the prediction algorithm (Serra and Turner, 1995). $\Delta G_{5'ATR}$ and $\Delta G_{3'ATR\_100}$ were calculated from sequence including ATR (with or without RBS), and the two scar sequences introduced during cloning process. $\Delta G_{-70-+38}$ is obtained from 70 nt upstream sequence and 38 nt downstream around ATG (+1) codon of GFP gene.

c. RT-qPCR

Figure 1B:
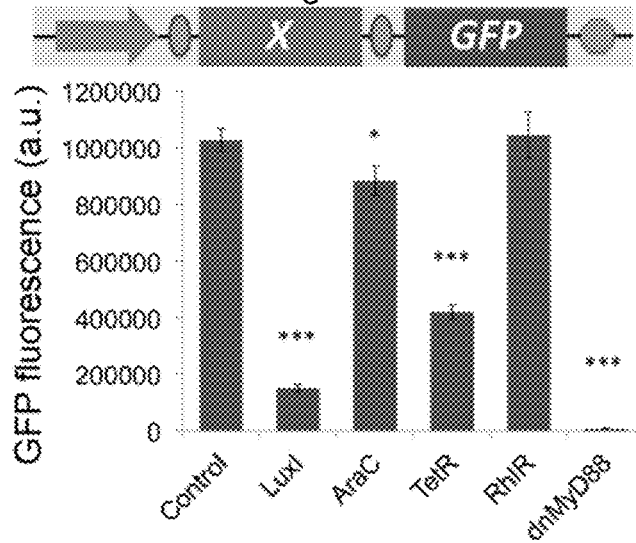

Total RNA was extracted from three individual cell cultures (1.5 mL exponentially growing cell cultures, fresh cultures) for each construct in FIG. 1B using Trizol® (Invitrogen). DNase I (NEB) was used to remove traces of genomic DNA and then the total RNA was further purified using PureLink® RNA Mini Kit (Life Technologies), and the eluted total RNA was quantified using BioTek's Synergy H1multi-mode Reader. cDNA was synthesized from RNA using an iScript cDNA synthesis kit and random primers (Bio-Rad). The reaction volume is 20 μL and ~1 μg RNA were used for reaction. Concentrations of cDNA were then quantified by qPCR using iTaq Universal SYBR Green Supermix (Bio-Rad) with the iQ5 Real-Time PCR detection system (Bio-Rad). Prokaryotic 16S rRNA was employed as endogenous control. Primers (IDT) used for amplifying 16S rRNA; 5'-GAATGCCACGGTGAATACGTT-3' (rrnB, forward, starting at the 1361st nucleotide, SEQ ID NO: 1), and 5'-CACAAAGTGGTAAGCGCCCT-3' (rrnB, reverse, starting at the $1475^{th}$ nucleotide, SEQ ID NO: 2) (Lira et al., 2011). Two pairs of primers were designed to amplify GFP are P1: 5'-CAGTGGAGAGGGTGAAGGTGA-3, (forward, starting at the 87th nucleotide, SEQ ID NO: 3); and P2: 5'-CCTGTACATAACCTTCGGGCAT-3' (reverse, starting at the 283th nucleotide, SEQ ID NO: 4); P3: 5'-AGACACGTGCTGAAGTCAAG-3' (forward, starting at the 320th nucleotide, SEQ ID NO: 5), and β4: 5'-TCTGCTAGTTGAACGCTTCCAT-3' (reverse, starting at the 539th nucleotide, SEQ ID NO: 6). qPCR result was analyzed using Bio-rad CFX Manager software version 3.1. Each sample was performed with two replicates for both 16S rRNA and GFP cDNAs, and gene expression was normalized to 16S rRNA. Delta Ct values were calculated ($C_t^{target}$ .... $C_t^{16S}$) compared with the biological control (Constitutive promoter-RBS-GFP) to calculate the relative GFP mRNA concentrations. Table 10 provides the minimum information for publication of quantitative real-time PCR (MIQE).

d. Flow Cytometry Measurement

All confirmed constructs were re-transformed into DH10B strain. Single colonies were picked and cultured in 4 mL LB medium (100 μg/ml ampicillin) for 24 hr at 37° C. for testing. Flow cytometry measurements were performed using AccuriC6 flow cytometer (Becton Dickinson) and all samples were analyzed at twelve-hour and twenty-four-hour time points, and the two time points showed similar GFP expression pattern (FIG. 9A). GFP excitation: 488 nm, and emission: 530±15 nm. All data were collected in a log mode. Data files were further analyzed by MATLAB (MathWorks). All the fluorescence data are collected by flow cytometry unless specified, and the fluorescence was not normalized against cell density because we measured the fluorescence of single cells, instead of the population, so the fluorescence value is not directly correlated with population density. 20,000 individual cells were analyzed for each sample at a slow flow rate.

e. Hysteresis Experiment

All synthetic toggle switch plasmids (T_S28, T_S67 and T_WT) were transformed into K-12 MG1655 strain with ladI-/-, and cells cultured overnight in LB medium. T_WT plasmid has been used in previous study (Wu et al., 2017). We prepared two pre-cultures with two initially different stable steady states, i.e., low GFP state (OFF) without inductions and high GFP state (ON) induced with enough aTc. The two cells were then inoculated into media containing an aTc concentration range so that cells with different initial conditions were grown in identical conditions. Specifically, for OFF-ON experiment, samples were diluted evenly into 5 ml polypropylene round-bottom tubes (Falcon) and induced with different amounts of aTc, Fluorescence was then measured at 6, 8, and 21 hr time points to monitor the fluorescence level. In our experiment, we found the intensity of fluorescence became stable after ~8 hr induction. For the ON-OFF experiment, cells were induced with 40 ng/ml aTc initially to prepare the initial ON cells, and fluorescence was measured at 8 hr to ensure they were fully induced. The initial ON cells were then collected by low-speed centrifugation, washed once to remove the inducer, resuspended with LB medium, and then diluted and transferred into fresh medium with various aTc concentrations at 1:100 ratio. Flow cytometry measurement was performed for each sample after 6, 10 and 18 hr culturing, respectively. Data shown in FIGS. 5A-5F are 18 hr results.

f. Sample Preparation and Microscopy

Single colonies were picked and grew at 37° C. in liquid LB medium. After 24 hours, 1 mL cells were collected and spun down at 2500 g for 5 min, washed with 1× phosphate buffer solution (PBS), and resuspended by 200 μL 1×PBS. 5 μL of concentrated cell solution was placed on glass microscope slides and images were captured with a NikonTi-Eclipse inverted microscope (magnification 40×). GFP was visualized with an excitation at 472 nm and emission at 520/35 nm using a Semrock band-pass filter. The exposure time for each sample was kept the same.

g. Growth (Curve Assay

Figure 9B:
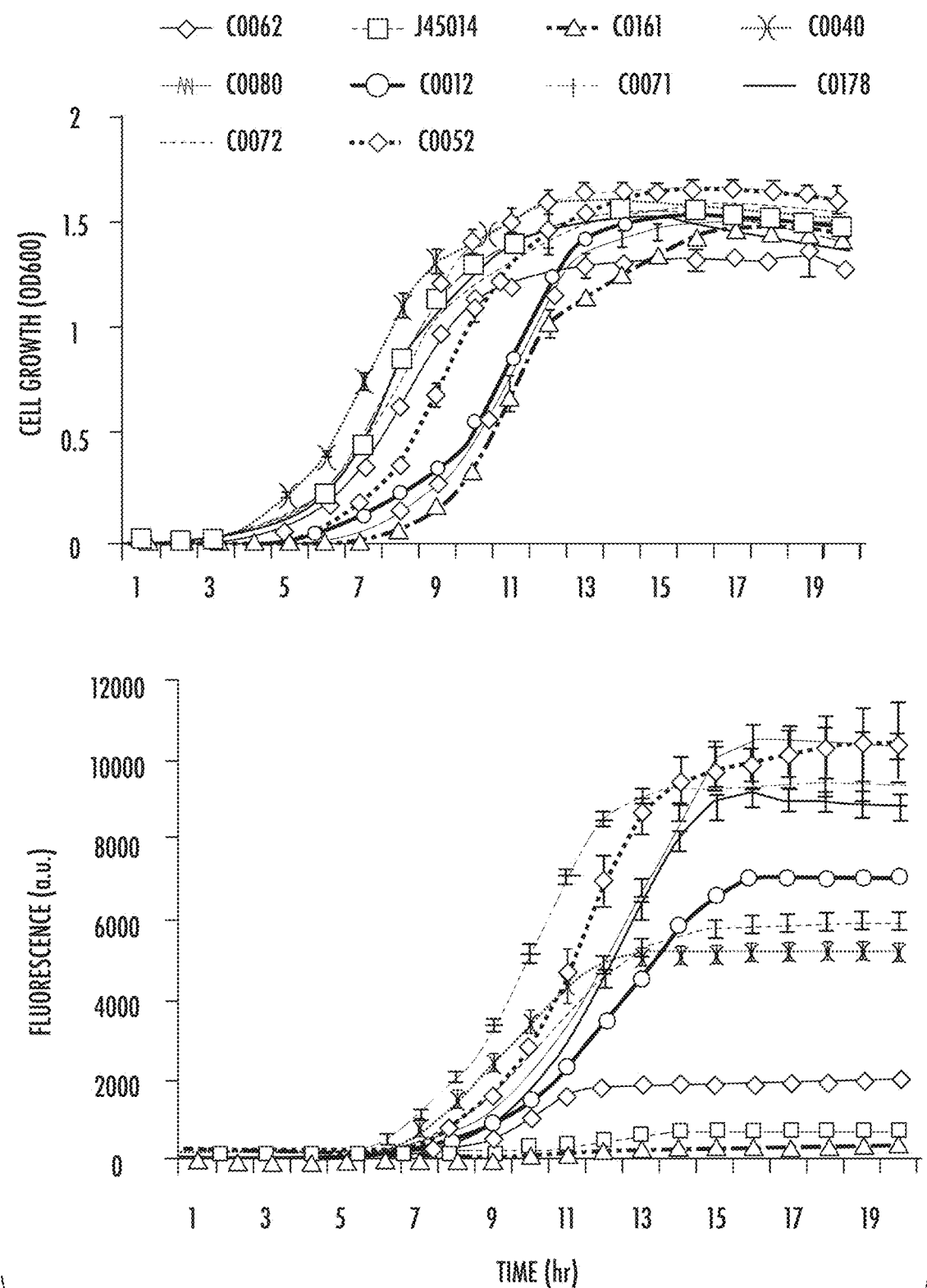

Ten different gene circuits with different fluorescence expression levels (high, medium and low) were selected to test their growth rates under the same condition. Single colonies harboring circuit plasmid were picked up and diluted into 4 mL LB medium, from which 300 μL were transferred into 96-well sterile plate. A negative control with only LB medium was also prepared. Optical density (OD600) and fluorescence (excitation: 485 nm; emission: 530 nm) were measured every 30 minutes by plate reader (BioTek) over 20 hours on a shaking platform and with the temperature controlled to 37° C., Three random colonies were picked up, and triplicate wells were measured for each sample. Our results indicated that gene expression in the circuit influenced the time of ceils going to the exponential phase, but all the samples went to stationary phase with similar OD value after ~12 hr (FIG. 9B). For stable protein expression, we chose the 24 hr data point in this study unless specified.

2. Results a. Protein Expression is Influenced by Adjacent Genes and Position

To examine whether protein expression is affected by its neighbors in a polycistronic setting, we first constructed a two-gene operon (gene X and GFP), which is driven by a constitutive promoter (FIG. 1B). Flow cytometry results showed that for different X, GFP expression varied significantly. Specifically, circuits with AraC and RhIR as X showed a comparable level of GFP fluorescence to the control (without X gene), while the others (LuxI, TetR, and dnMyD88) showed high expression variations, ranging from 6-fold to over 120-fold decrease compared to control (FIG. 1B). Membrane protein dnMyD88 shows the most significant-influence on its neighbor GFP expression. On the other hand. RT-qPCR measurements of transcripts of GFP showed much smaller variations of mRNA concentrations between different circuits, for P1:P2 (GFP N-terminal) or P3:P4 (GFP C-terminal) primer pairs, (FIGS. 1C and 6A-6C). So the variation of mRNA concentrations for each construct is insufficient to explain the fluorescence differences, which is in agreement with previous studies that protein and mRNA copy numbers in $E. coli$ cells are uncorrelated (Lim et al., 2011; Taniguchi et al., 2010).

Figure 1D:
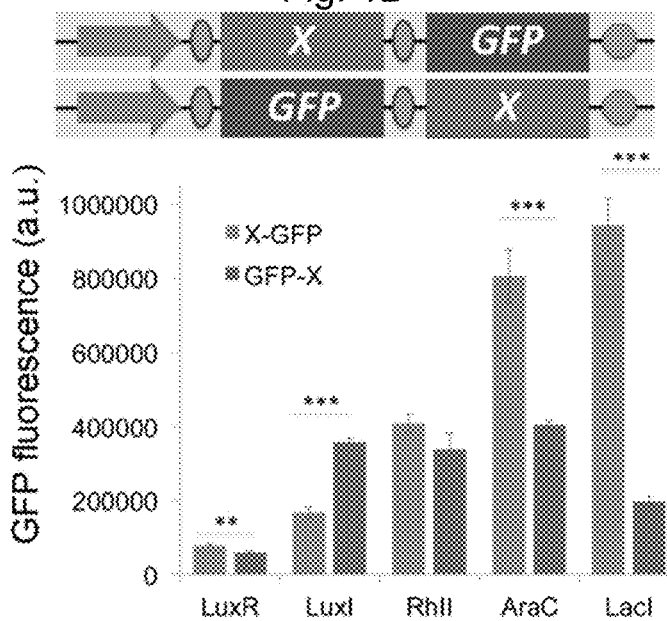

Next, we further investigated the influence of a gene's position on its expression. As shown in FIG. 1D, higher GFP expression is observed when GFP is arranged distal to the promoter for the bi-cistronic constructs that X gene is RhII, AraC, or LacI, while there are cases showing similar level GFP fluorescence (LuxR) or higher (LuxI) when GFP is arranged right, downstream of the promoter. Results from tri-cistronic constructs also indicated that GFP expression is varied for different positions in the circuit and adjacent, genes (FIGS. 6D-6G). Moreover, for different Xs with the same position, GFP showed substantial variations, consistent with results shown in FIG. 1B, Altogether, these results demonstrate that a gene's sequence and position in operons have an effect on adjacent genes' expression.

b. Quantitative Characterizations of ATR Effects on Synthetic Operons

To quantify ATRs' impact on protein expression, we designed and constructed ~80 circuits with different neighbor protein-coding genes and varying sizes (X and Y) to cover a wide range of GFP gene position and neighbor features (GC content, size, and mRNA secondary structure). These genes are commonly used in synthetic biology, including transcriptional factors, quorum-sensing components, and other functional genes. To ensure experimental consistency, all circuits are constructed using the same constitutive promoter, RBS, terminator, and expression vector.

First, GFP was arranged to the distal end of synthetic bicistronic and tricistronic operons and DNA sequence, starting from the transcription start site after the promoter to the beginning of the RBS of GFP, is denoted as 5'ATRs (FIG. 2A). Log-transformation was applied to the original data because of its large variability ranging from 21,000 to 1,900,000 (GFP fluorescence, arbitrary unit) and inconstant variance (STAR Methods). GFP expression increased with the total 5'ATRs GC content, while 5'ATR length had negative effects on GFP expression. Sliding window analysis of 5'ATR GC content suggested that the GC content of the whole 5'ATR has the highest fitting efficiency (FIG. 7A). We hypothesized that high GC content could increase total mRNA stability, while long transcription process could decrease the probability of complete GFP transcription/translation and increase the degradation probability. Additionally, previous studies reported that RNA secondary structure near the RBS influences a gene's expression, so local folding energy from −70-nt to +38-nt region around GFP's RBS (GFP's translation starting site is denoted as +1) were calculated. Consistent with previous reports (Kudla et al, 2009; Mao et al., 2014; Tuller et al., 2010), our analysis also showed that GFP expression is significantly correlated with folding energy around RBS of GFP (FIG. 2A and Table 4).

Next, GFP was placed in the middle of the operon, and the sequence between stop codon of GFP and the transcriptional terminator is denoted as 3'ATR. We found that 5' ATR GC content (positive impact) and local mRNA folding free energy (negative impact) had the most significant impacts on GFP expression and 3'ATR GC content has a small contribution to GFP variations in this case (FIG. 2B and Table 4). Finally, circuits with GFP engineered proximally to the promoter were also constructed and investigated to probe the relationship between GFP expression and its 3'ATR, Similarly, results show 3'ATR. GC content and size has a positive and negative relationship with GFP fluorescence, respectively (FIG. 2C and Table 4). Sliding window analysis further revealed that the GC content of first 100 nt of 3'ATR had the highest fitting efficiency, suggesting the rear 100 nt is important for GFP expression (FIG. 7B).

Non-coding DNA sequence makes up about 12% of bacterial genome and plays important, roles in the regulation of gene expression and metabolism (Ahnert et al., 2008; Oliva et al., 2015). To investigate whether non-coding sequences would similarly affect adjacent gene expression in synthetic operons, we engineered 32 synthetic circuits with 32 genes, which are placed immediately downstream of the promoter without RBS to greatly limit their translation (FIG. 7C). Our results showed strong relationship between GFP expression and non-coding 5'ATR GC content, size, and local mRNA folding energy (FIG. 2D and Table 5). Higher GFP expression was observed for circuits with the same genes with RBS than those without RBS (FIG. 7D), suggesting the RBS of 5'AIR may be important for mRNA stabilization and expression efficacy.

Altogether, these results offer direct evidence that adjacent coding and non-coding DNA fragments affect gene expression in synthetic operons, and ATR GC content has a positive correlation with GFP expression while ATR size and local free energy are both negatively correlated.

c. Comprehensive Model of ATR Regulation

Our results revealed that gene expression in operons is affected by its adjacent genes' sequence features and local mRNA secondary structures. The explicit mechanism of these effects remains elusive. We employed the same promoter, RBS, vector, and host cell for all the circuits to minimize transcription impacts on protein expression variation. And there is a lack of complicated post-translational modifications in *E. coli*, so we believe that the ATR alters the secondary or tertiary structures of mRNA locally and/or globally, which perturbs the GFP mRNA translation and degradation process (FIG. 2E). 5' and 3' ATRs' GC contents have positive relationship with GFP expression (FIGS. 2A-2F). After ribosome binding site is transcribed, ribosome and RNase competitively bind to mRNA (Chen et al., 2015a; Mackie, 2013). So we infer that a GC-rich 5' and 3'ATR, which is likely to have more stable secondary structure (Emory et al., 1992; Selinger et al, 2003), could help stabilize GFP transcript and decrease the risk of degradation by RNase and thus result in higher GFP expression. On the other hand, the 5' and 3' ATR sizes are negatively correlated with GFP expression (FIGS. 2A-2F). Longer ATR may lead to lower mRNA stability due to the increased probability of elongation pausing and degradation of RNase. Moreover, the local mRNA folding energy near GFP's RBS (nt −70 to +38) is believed to impact the translation initiation of GFP (Kudla et al., 2009; Mao et al., 2014; Fuller et al., 2010). Overall, our statistics analysis revealed that 5'ATR GC content is the most important variable in the regression models for X-GFP circuit (FIG. 2A, partial $R^2$=0.44, Table 6) and X-GFP-Y (FIG. 2B, partial $R^2$=0.5 0.1), whereas 3'ATR size has a bigger role in the model of GFP-X (FIG. 2C, partial $R^2$=0.58, and Table 6). This result, suggests that gene expression may be more easily modulated by the GC content of its 5'ATR and size of 3'ATR.

A comprehensive linear model was developed integrating the three scenarios in FIGS. 2A-2C, to explore the mechanistic basis of ATR regulation and make quantitative predictions. The biophysical model was based on previous pioneer work characterizing the relationship between free energy changes and protein translation initiation (Salis et al., 2009; Serra and Turner, 1995; Smit and Duin, 1990; Xia et al., 1998). The comprehensive model disclosed herein was then developed. The model builds on measurements of sequence-dependent energetic changes during polycistronic mRNA folding and translation. The energetic changes correspond to the translation efficiency and protein abundance (c):

$$c^{\infty}\exp(-\Sigma\beta x\Delta Gx), x=1,2,3,\ldots$$

where $\Delta G$ is the energy term and $\beta$ is the scaling coefficient (Salis et al., 2009). For a given gene in an operon, the size of 5' and 3' ATR is denoted as i nt and j nt, respectively in FIG. 2E. The minimum free energy of local GFP mRNA secondary structure around RBS is $\Delta\Delta G_{-70-+38}$. The entire folding energy for 5'ATR is $\Delta G5'ATR$. GC content of the first 100-nt 3'ATR has the highest fitting efficacy for GFP expression (FIGS. 2C and 8B), and it is known that GC content is correlated with thermodynamic parameter $\Delta G$ (Seffens and Digby, 1999; Trotta, 2014), so we only calculated free energy of the first 100 nt of 3'ATR ($\Delta G_{3'ATR\_100}$). Thus, the sum of energy changes can be quantified to assess the abundance of a given gene expression:

$$-\Sigma > x\Delta Gx = \beta 0 + \beta 1 \cdot \Delta G_{5'ATR} + \beta 2 \cdot \Delta G_{3'ATR\_100} + \beta 3 \cdot i \cdot Gm + \beta 4 \cdot j \cdot Gm + \beta 5 \cdot \Delta G_{-70-+38}$$

The folding energy of $\Delta G_{5'ATR}$, $\Delta G_{3'ATR\_100}$ and $\Delta G_{-70-+38}$ are totally sequence-dependent, and Gm is an average energy cost for synthesizing a nucleotide, which here for simplicity we assume it is a constant. Although all the five variables are contained in the model, some variables may be unnecessary for a specific gene organization in a circuit. For example, in the non-coding ATR cases with X-GFP organization (FIG. 2D), the j and $\Delta G_{3'ATR\_100}$ terms are constant values, owing to a lack of 3'ATRs. Values for Gm and the scaling coefficients for tri-cistronic and bi-cistronic coding gene circuits are provided in Table 5; those same values for bi-cistronic non-coding (i.e. FIG. 2D) are provided in Table 9.

Figure 2F:
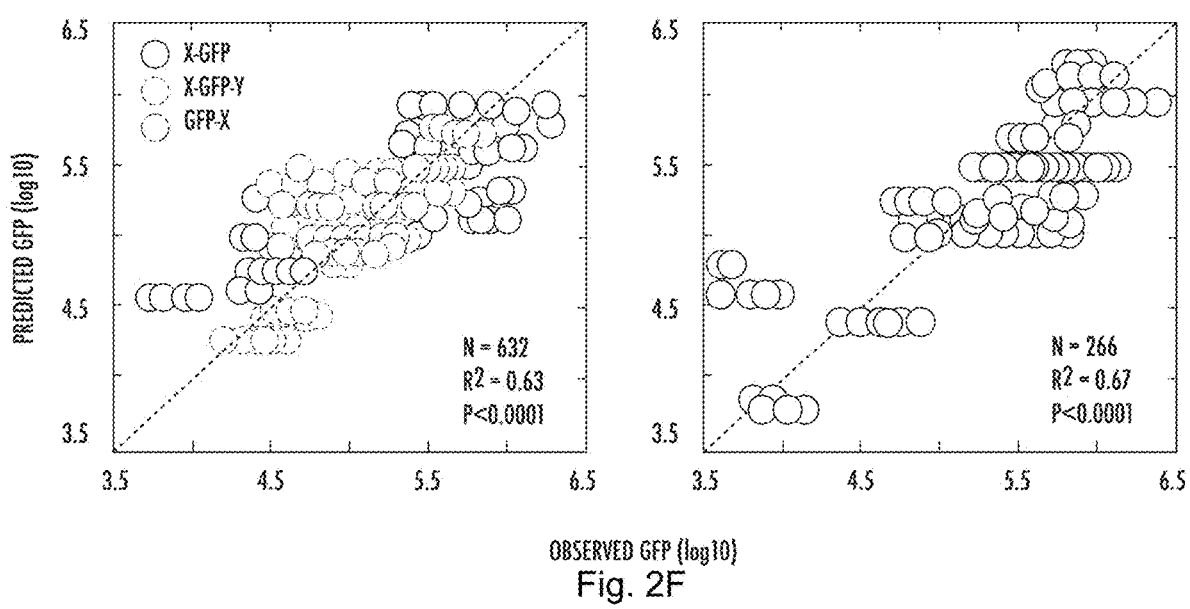

The comprehensive model combined the three different scenarios with GFP placed at different positions in a polycistronic gene circuit (FIG. 2A-2C). To verify whether the five variables are necessary for the best prediction of the model, we performed stepwise regression to test the significance of each variable through adding or removing one of the variables step-by-step (the significance levels for variable entry or stay is 0.05). From the sequence of generated models, the selected model is chosen based on the lowest Akaike information criterion. Our results indicated that all the five variables are necessary for the coding-ATR model integrating the three scenarios in FIGS. 2A-2C (Summary of Stepwise Selection in Table 7), and the comprehensive model explains 63% of GFP variations (FIG. 2F, left portion). The non-coding ATRs model with the three statistically significant variables $\Delta G_{5'ATR}$, i, and $\Delta G_{-70-+38}$ (Summary of Stepwise Selection in Table 7) explains 67% of GFP variations (FIG. 2F, right portion). With the comprehensive model, we can evaluate the influence of the adjacent transcriptional sequences on a certain gene's expression in the operon, which provides a guide for circuit design and optimization during circuit engineering.

d. Protein-Expression Metric Guided Logic Circuit Design

To illustrate how the metric could be used to guide circuit design, synthetic AND logic gate was designed and tested. The gate is composed of a hybrid promoter pLux/tet, which has one LuxR-AHL and one TetR binding site. GFP is the output. Maximized GFP expression is achieved in presence of two inputs AHL and aTc (FIG. 3A), where AHL binds with LuxR protein to activate pLux/tet transcription and aTc can block TetR repression to pLux/tet. LuxR and TetR are constitutively expressed from the same promoter, it should be noted that these methods may be applied to any other type of gene circuit, including but not limited to logic gates, oscillators, and multi-stable toggles.

Figure 8A:
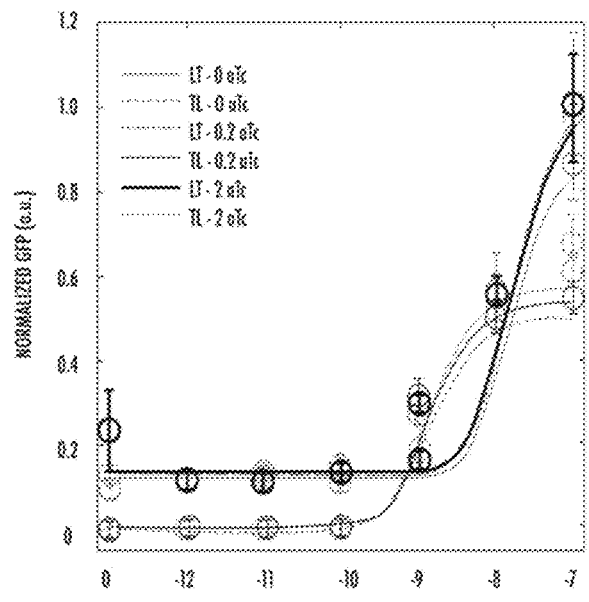
FIGS. 8A-8E show, in accordance with certain embodiments, a model simulation and experimental validation of GFP dynamics for synthetic logic gates; GFP expression prediction using synthetic fragments with different GC content, or sizes and model refinement; and model simulation for different production rates of LuxR and TetR in circuit LT and TL (Related to FIGS. 3A-3D and 4A-4D and STAR. Methods).

There are two possible ways to assemble this circuit, one is LuxR-TetK (LT) combination, and the other is TetR-LuxR. (TL). The GC content of LuxR (30.3% GC, 781 bp) is lower than TetR (40.4% GC, 685 bp). So in AND-gate LT, TetR expression is lowered by its 5'-low-GC-content neighbor while the impact of LuxR to TetR expression in logic TL is minor because the size of 3'ATR is a more significant factor compared to GC content. We then calculated the equation for each circuit design and feed it into our model, results indicate that LuxR expression in TL decreases by 4.4% compared to gate LT, however, TetR expression increases by 93.6% in circuit TL (Table 5). Therefore, we infer that the basal GFP expression in circuit LT would be greater than in TL, whereas TL would harbor more dynamic responses with induction of aTc because of higher TetR expression. An ordinary differential equation (ODE) model was then developed, based upon the Hill equation, to simulate GFP expression based on the normalized LuxR and TetR production rate changes in the LT and XL gates (STAR Methods). By tuning the relative production rates of LuxR and TetR according to the comprehensive regression model, we can predict GFP dynamics under induction of AHL and aTc (FIGS. 3B and 8A, solid lines). It can be seen that, after normalization, experimental dose-response results, shown as colored circles, are consistent with ODE model predictions for all aTc concentrations. Basal expression of pLux/tet in circuit LT is significantly higher than in circuit TL (FIGS. 3B and 8A, data points with error bar). Moreover, the maximum GFP fluorescence is also higher in circuit LT, owing to decreased LuxR expression in gate TL. Additionally, the sensitivity to AHL (concentration for half-maximal activation of GFP, K0.5) is improved 2.4~64.5 fold in circuit TL compared to LT for different concentrations of aTc. And the nonlinearity (hill coefficient) is generally increased 2~5 fold with high concentrations of aTc induction. These data are in accordance with the model calculations that TetR expression is relatively increased in circuit TL than in LT, which suppresses the basal expression of pLux/tet and improves the sensitivity and nonlinearity of the promoter to AHL and aTc.

Figure 3C:
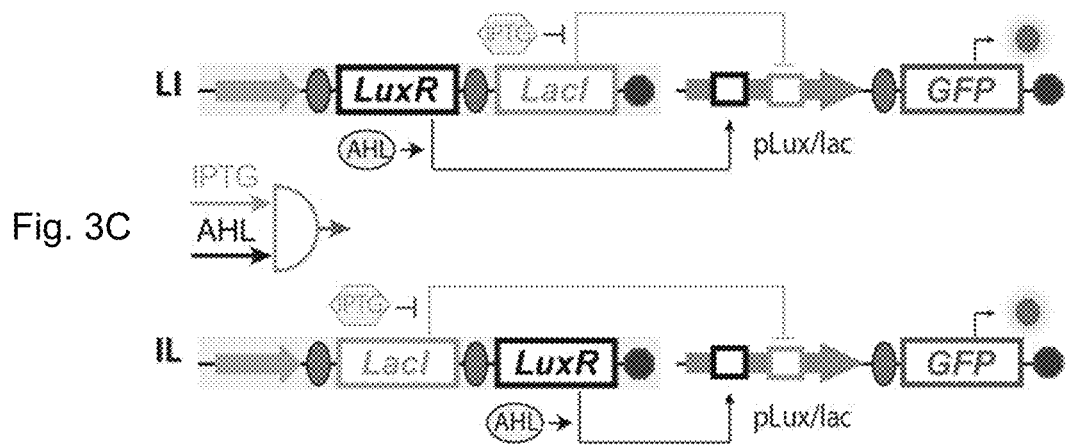
Figure 3D:
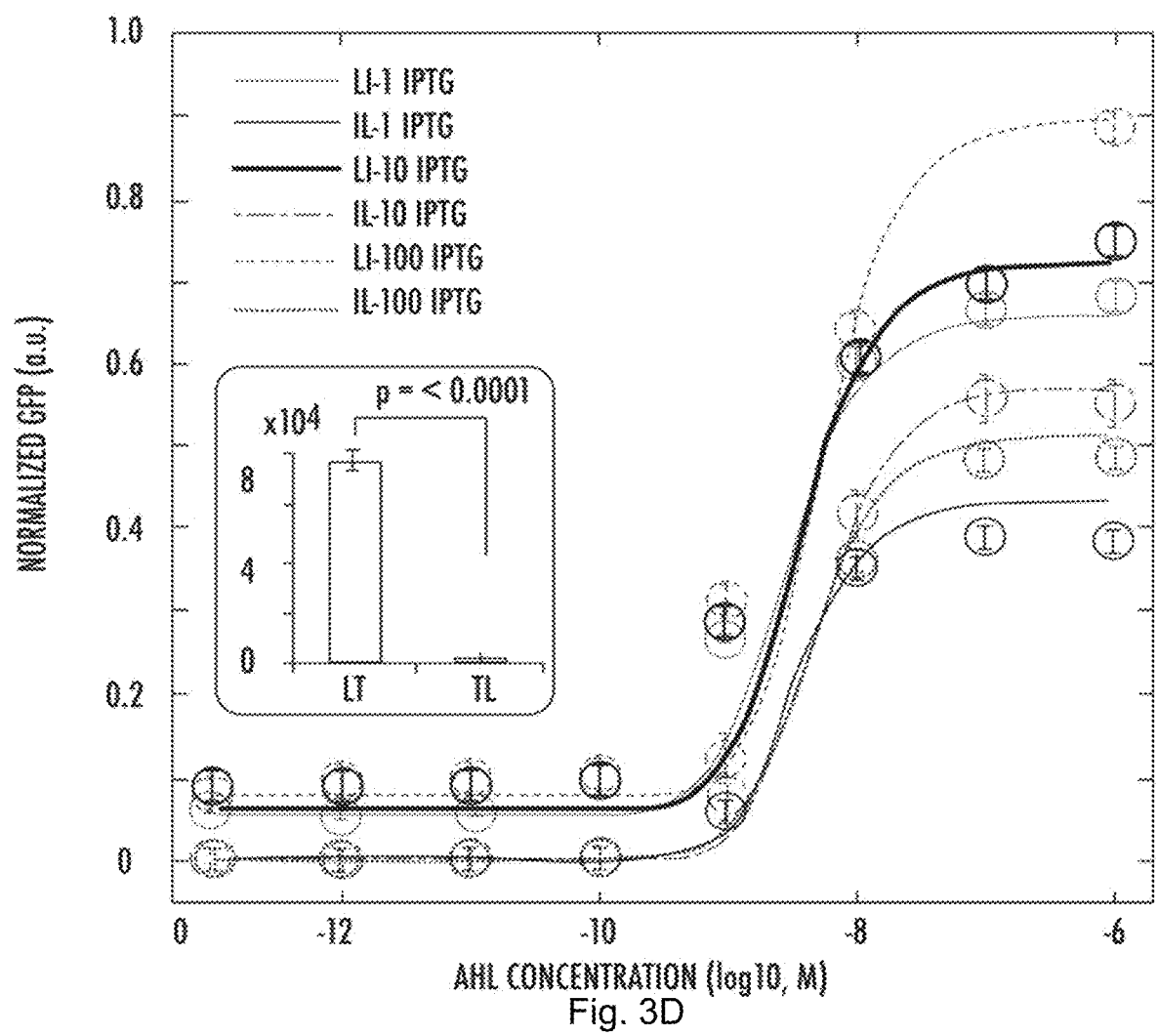
Figure 8B:
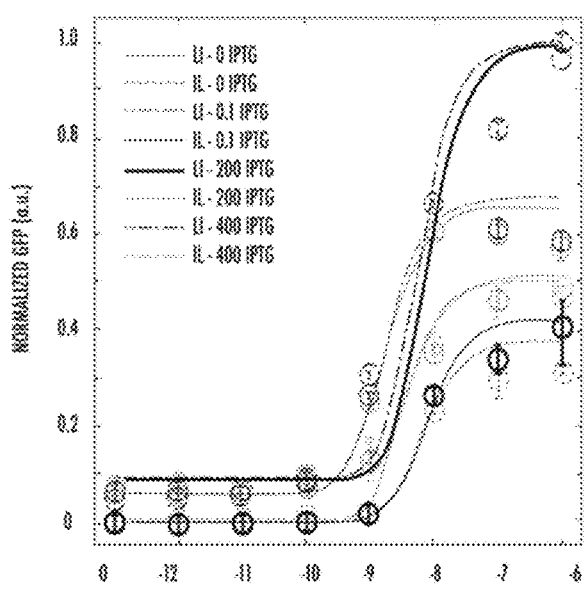

To further validate the metric's utility, another two AND-gate gene circuits (LI and IL) with switched genes' (LuxR and LacI) position were designed (FIG. 3C). Hybrid promoter pLux/lac was used to indicate the relative concentrations of LuxR and LacI produced from the operon. LacI (53.3%, 1153 bp) has a high GC content, which may increase LuxR expression. Our model calculations showed that LuxR expression increases by 74.3% and LacI increases by 38.1% in circuit IL than in LI (Table 5). Since promoter pLux/lac has two LacI-binding sites (one is in the region between −35 and −10, and the other is downstream of −10 element), so the overall LacI inhibition efficiency is increased ~76.2% considering the importance of spacing between −35 and −10 element to RNA polymerase binding. Therefore, the basal GFP expression of logic IL would be lowered compared to LI. The ODE model also indicates higher GFP expression in gate LI (FIGS. 3D and 8B, solid lines). Experimental results confirmed that the basal expression for circuit LI is ~54-fold higher than IL, and GFP expression under each inductions are higher in gate LI, which is consistent with the ODE model results. (FIGS. 3D and 8B).

Taken together, the two sets of AND logic gates showed an example of applying our comprehensive model based tool to evaluate each gene's relative expression level in synthetic AND gate gene circuits, and verified that ATRs' features and local mRNA stability changes in an operon-based gene network affect protein expression and the circuit performance, including basal level, sensitivity, and nonlinearity. Furthermore, the tool could serve as a much-needed quantitative guidance to rational design and optimization of gene expression for large genetic circuits.

It should be noted that in various embodiments, a deterministic model may be used to simulate the performance of an intended function (in these example above, an AND logic gate). In some embodiments, the deterministic model may be structured upon an ordinary differential equation. As a specific example, the model may make use of the Hill equations.

e. Timing Gene Expression with Synthetic 5' ATRs

Figure 8C:
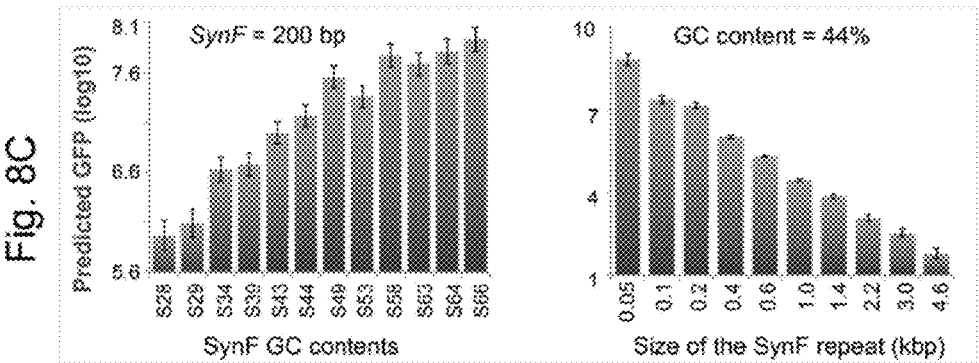

In general, the minimum free energy of RNA folding has a negative correlation with GC content (Seffens and Digby, 1999; Trotta, 2014). Next, we seek to use synthetic non-coding DNA fragments, with the same size but varying GC content or same GC content but varying sizes, to fine-tune gene expression in synthetic circuits. We first synthesized six short DNA fragments (with a constant size 200 bp) with varying GC content from 28% to 53%, which were inserted downstream of LuxR gene but upstream of GFP in the two-gene operon (Promoter-LuxR-Synthetic fragment-GFP). According to our model, synthetic fragments with varying GC content could tune GFP expression (FIG. 8C).

Figure 4B:
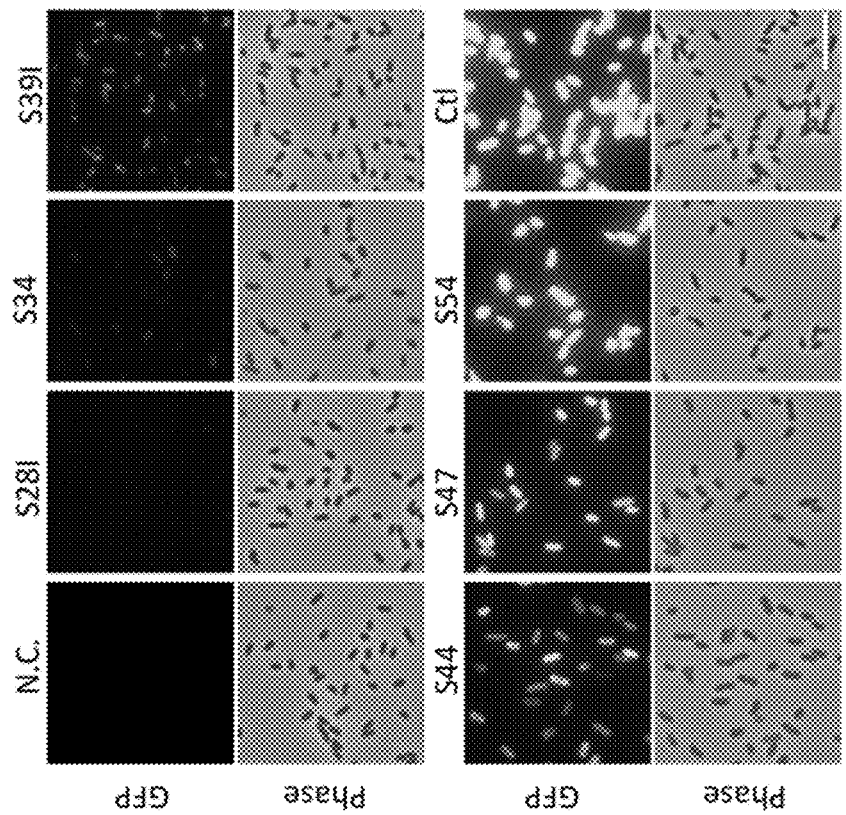
Figure 4A:
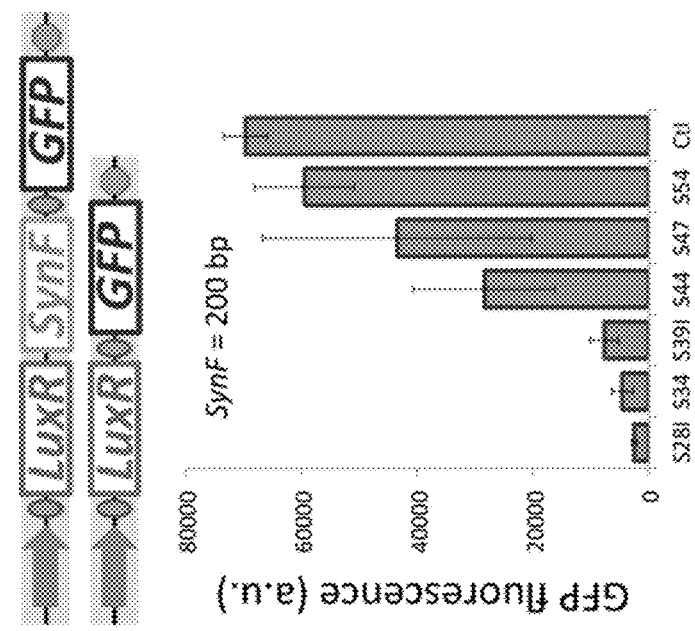

Experimental results show that GFP expression is continuously increased for synthetic fragments with increasing GC content from 28% to 53% (FIG. 4A). Low GC-content fragments down-regulated GFP expression for about 25-fold. Microscopy results further confirmed flow cytometry data and visualized gradual increase of fluorescence intensity with increasing GC-content ATRs (FIG. 4B). Using this strategy, we further synthesized 13 DNA fragments as 5'ATRs with varying GC content but having a constant size (200 bp), and placed downstream of the promoter (FIG. 4C). Results indicate that synthetic short DNA sequences have a substantial impact on GFP expression: low GC-content ATRs largely decrease its neighbor's expression (up to 366-fold), and exhibit a gradually increasing pattern from 28% to 48%, while high GC-content (48% to 67%) ATRs drive GFP expression to a comparable level to the control (without synthetic fragments). It is possible that GFP achieves its maximum expression when the upstream ATR mRNA piece has a relatively stable structure.

Figure 8D:
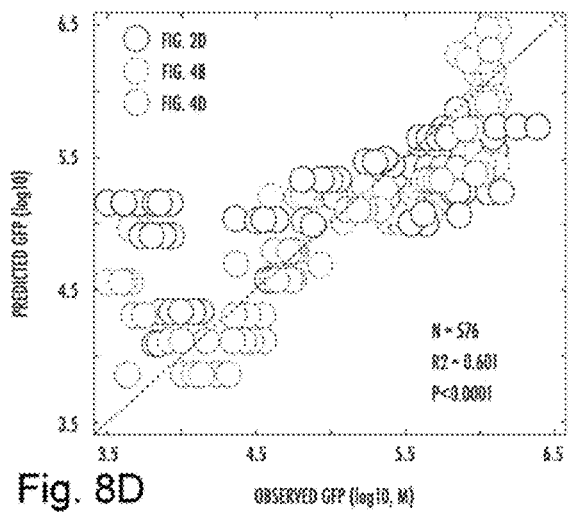

To further verify the role of ATR regulation, we varied the size of 5'ATR through shortening and adding a common sequence (Egbert and Klavins, 2012). Using S44 (GC: 44%; Size: 200 bp) in FIG. 4C as the seed sequence, we shortened it to 100 bp and 50 bp, and lengthened it from 400 bp (combined with two pieces of S44) to 4600 bp (combined with 23 pieces of S44), and all the ten fragments have the same GC content (44%, FIG. 4D), Model analysis and flow cytometry results show that GFP fluorescence intensity gradually decreases with increasing 5'ATR sizes (FIGS. 8C and 4D). We also used the data to further refine our comprehensive non-coding model and found three variables $\Delta G_{5'ATR}$, i, and $\Delta G_{-70\to+38}$ are still required for the best fitting efficacy and explains 60.1% of GFP variations (FIG. 8D and Table 9). The refined model further expands the variables' range (GC: 28% to 67%, and Size: 50 to 4600 bp) and could provide more accurate predictions. Taken together, we demonstrate that synthetic non-coding 5'ATRs with designed GC content and sizes can be used to accurately tune gene expression and achieve expression levels spanning more than 300-fold.

f. Using Synthetic ATRs to Tune Toggle Switches

Finally, we illustrated the application of synthetic ATRs to modulate the nonlinear bistable potential of synthetic toggle switches. As illustrated in FIG. 5A, LacI protein could inhibit TetR by binding the pLac promoter while TetR could bind pTet to block LacI expression, forming a mutually inhibitory network. Here, we positioned 200 bp synthetic ATRs with 28% and 67% GC content upstream of RBS-TetR module to tune TetR production (T_S28 and T_867), According to our analysis above, low GC-content 5'ATR can down-regulate TetR expression while high GC-content can keep TetR at a high level.

Flow cytometry was employed to analyze the initial states of the toggle switches with ATR insertions. As shown in FIG. 5B, T_WT initially shows bimodal distribution, GFP-ON and GFP-OFF populations, resulting from gene expression noise in a relatively balanced system. In contrast, both T_S28 and T_S67 exhibited unimodai distributions. Synthetic ATR S28 decreased TetR expression leading to higher LacI and GFP expression, whereas fragment with 67% GC content showed a lower GFP expression than T_S28 and slightly lower than the high-GFP population cells in T_WT (FIG. 5B). The results indicated that the synthetic ATRs could tune the initial steady states of toggle switches and modulate the population from bimodal to unimodal distributions.

To achieve a quantitative understanding of the ATR's regulation on bistability, we performed bifurcation analysis from the same mathematical model as the classical toggle switch (Gardner et al., 2000). We found that, the production rate of TetR has a considerable effect on bistability and bistable region. A small production rate, corresponding to low-GC ATR, has a small bistable region, whereas increase of production rate leads to larger bistable region (FIG. 5C). Experimentally, hysteresis of the three toggles were tested to verify the model analysis. Results indicated that all the three toggles exhibited hysteresis and T_WT harbors the broadest-bistable region (FIGS. 5D-5F). Moreover, consistent with model analysis, the bistable regions are gradually decreased from T_WT to T_S67 to T_S28. Collectively, these results validate a novel strategy of using synthetic ATRs to tune gene networks' initial steady states and bistability. Furthermore, this example demonstrates the feasibility of bridging ATR regulation with mathematical modeling to quantitatively understand and tune gene network dynamics.

3. Quantification and Statistical Analysis a. Statistical Analysis and Comprehensive Model Development To investigate the correlation between GFP expression and sequence characteristics in different circuits with different genes and organizations, we performed multiple linear regression analysis using the classical statistical software SAS9.4. Here, we mainly focused on five different independent variables including 5'- and 3'-ATR GC content (variable is computed as a percentage), 5'- and 3'-size (variable is computed as segment length), and $\Delta G_{-70\to+38}$, all of which can be computed from the DNA sequence in each circuit. The dependent variable is GFP fluorescence measured by flow cytometry, which was transformed to log scale during analysis. Eight data points collected in three days were used for regression analysis in FIGS. 1A-1D and 2A-2F, and twelve data points were collected in three different days for the 17 transcriptional factors insertion as non-coding ATRs, and all of the collected data points are imported to SAS for analysis.

All the information of the five variables is calculated from the specific DNA sequence. The 5'ATR includes the sequence from the scar right, after the promoter to the scar right before the RBS of GFP. And the 3'ATR includes the sequence from the scar right after the GFP to the scar right before the terminator. The scar sequence is generated from the molecular cloning using bio brick modules, and the size is 6 or 8 nucleotides. GC content and size of ATRs are calculated using the web server Endmemo. $\Delta G_{-70\_+38}$ were computed using NUPACK webtool. Since the AG are negative values, log transformations were performed to the absolute value of $\Delta G$, and then set to negative value. To build a comprehensive model for all the scenarios in FIGS. 2A-2C (GFP-X, X-GFP-Y, and X-GFP), we introduced dummy values for some variables in some regression analyses for analytical convenience. For example, construct GFP-X (FIG. 2C) has no varied 5'ATR (only a RBS and scar sequence), and its GC content value is set to 0.04 instead of 0. Similarly, $\Delta G_{5'ATR}$ is set to –0.05 for constructs without 5'ATR, and $\Delta G_{3'ATR\_100}$ is set to –0.00001 for constructs without 3'ATR. These dummy values don't significantly influence model fitting efficiency.

We first use scatter plot to display the relationship between GFP and each of the variables we are interested, without any data transformation. As shown in FIGS. 10A-10D, the data has a large variability ranging from 21,000 to U.S. Pat. No. 1,900,000 (arbitrary unit), and the fit without transformation is weakly linear and heteroscedastic. It would be problematic to use linear data for regression because of the inconstant variance from the data. However, the log is a variance stabilizing transformation, and it clearly reduced changes in variability of the data along the x-axis (FIGS. 2A-2D). Furthermore, transformed data conforms to an early normal distribution (FIG. 9C), more easily enabling us to perform multiple regression analysis to find a quantitative estimation of the relationship between GFP and the other three or five variables together.

To explore possible mechanistic basis of ATR regulation, we developed a comprehensive linear model based on the sequence-dependent energetic changes during the polycistronic mRNA folding and translation and the costs of protein biosynthesis. The biophysical model was based on previous pioneer work characterizing the relationship between free energy changes and protein translation initiation (Espah Borujeni and Salis, 2016; Sails et al., 2009; Smit and Duin, 1990). We calculated the free energies for 5'ATR and the first 100 nucleotides of 3'ATR ($\Delta G_{5'ATR}$ and $\Delta G_{3'ATR\_100}$) using NUPACK. Since all the energy terms are negative values, absolute values were first acquired for each of them and then set to negative values for data analysis. The constant Gm is set to 1, and for cases of non-coding ATRs, the coefficients for j and $\Delta G_{3'ATR\_100}$ are set to 0, owing to a lack of 3'ATRs.

To find the linear comprehensive coding-ATR model having the best prediction of dependent variable from the independent variables, we performed stepwise regression with the five variables: $\Delta G_{5'ATR}$, $\Delta G_{3'ATR\_100}$, 5'ATR size, 3'ATR size and $\Delta G_{-70\_+38}$. Stepwise regression is an automated tool for model selection through adding the most significant variable or removing the least significant variable as needed for each step (the significance levels for variable entry or stay is 0.05). From the sequence of generated models, the selected model is chosen based on the lowest Akaike information criterion. Results showed that all the five variables are statistically significant for the best, prediction of GFP expression in the comprehensive coding-ATR model, and explains 63% of GFP variations (Table 7). It is necessary to note that the negative correlation between protein abundance (c) and the sum of energetic terms ($\Sigma\beta_x\Delta G_x$) in the equation is already reflected in the coefficients of each term.

Figure 9C:
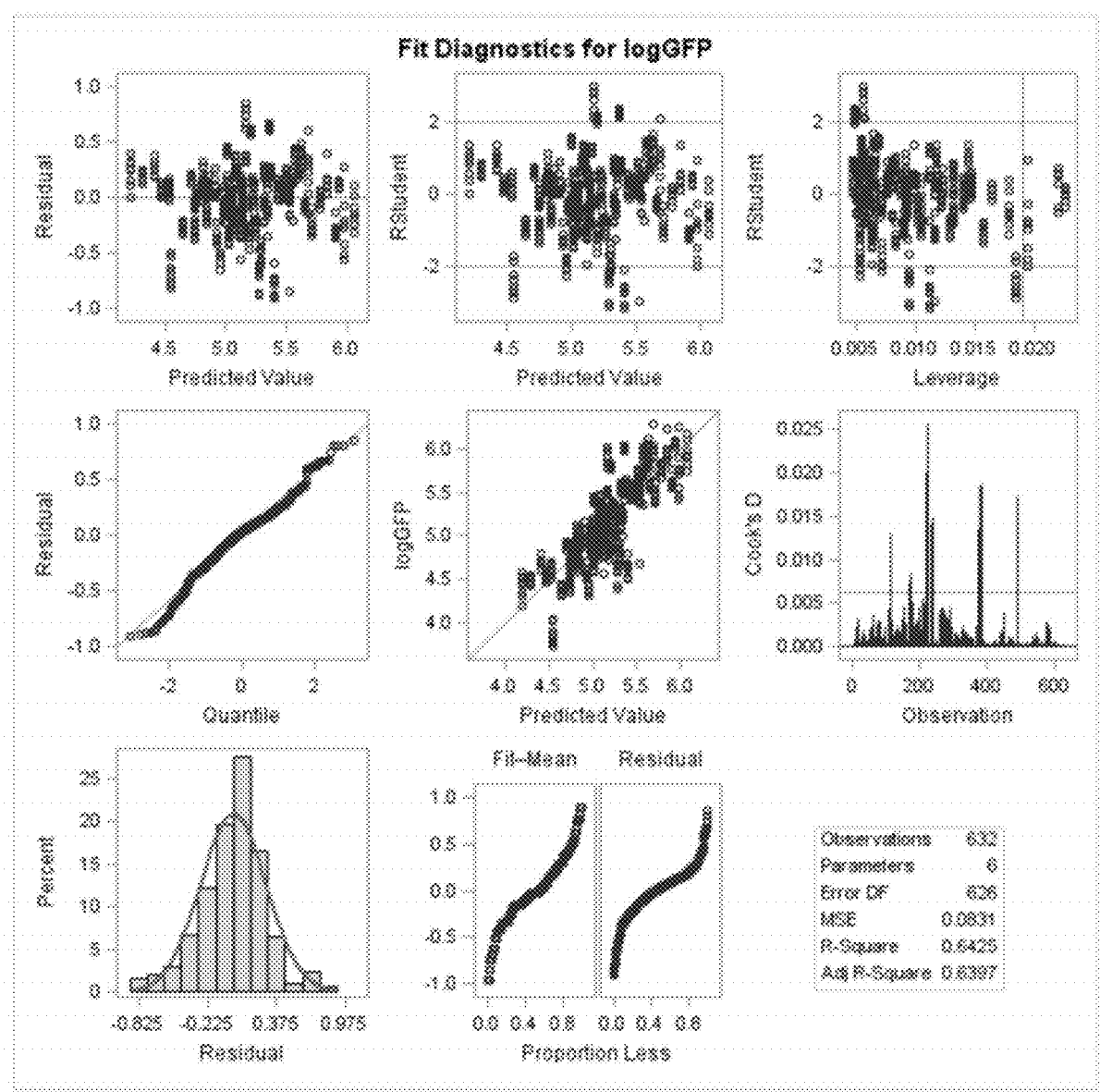
Figure 10A:
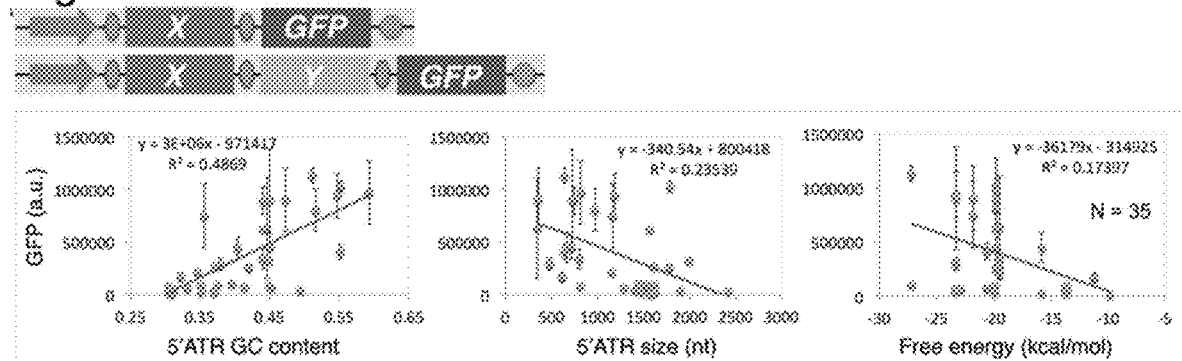
FIGS. 10A-10D depict, in accordance with certain embodiments, linear plots with GFP and variables in FIG. 2A-2D, without log transformations (Related to STAR Methods and FIGS. 2A-2F).
Figure 10B:
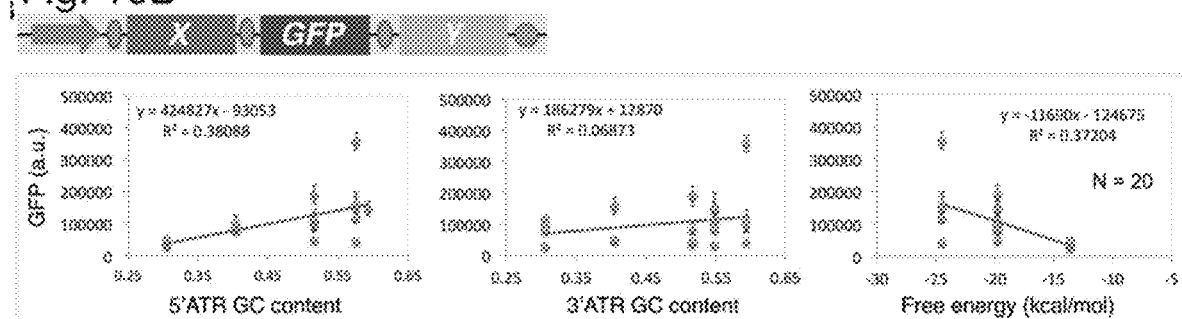
Figure 10C:
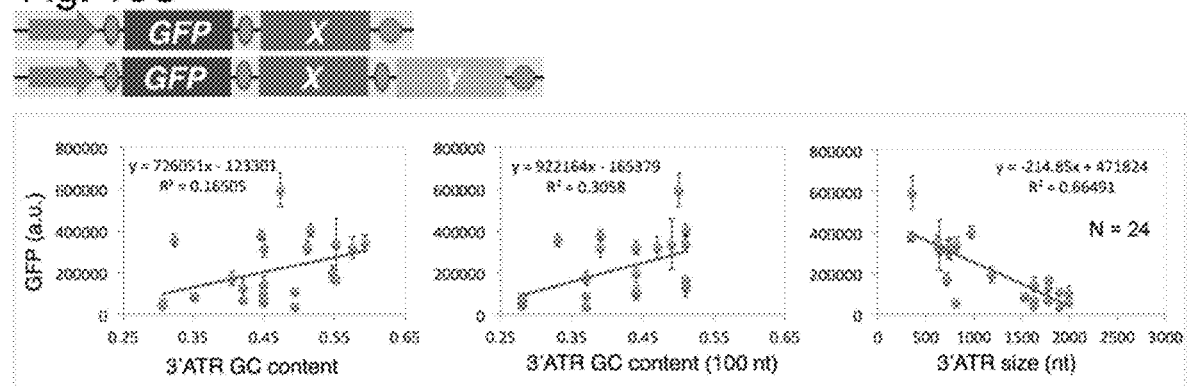
Figure 10D:
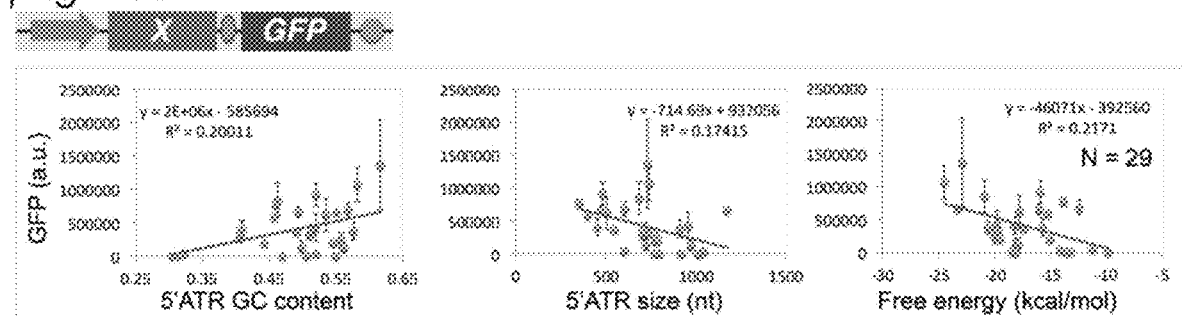

The fitting diagnostics indicated that there is no apparent trend for the residuals, and the data is roughly normally distributed, and the variables in the model explain most variation in the response variable from the residual-fit result (FIG. 9C). The predicted value by observed GFP plot. (Predicted Value-log GFP) reveals a reasonably successful model for explaining the variation in GFP for most of the circuits (FIG. 2F, left portion and FIG. 9C). The predicted responses (log GFP value) are calculated according to the generated linear regression model, with the corresponding inputs from each circuit. And a plot of predicted GFP against experimentally observed GFP values are then generated to evaluate and visualize the model-fitting efficacy (FIG. 2F). If the model predicted values and observed values agreed perfectly ($R^2$=100%), all the data points would fall on the dotted diagonal line of the squares. However, several outliers in the combined model are also observed and some observations with high leverages might also be overly influencing the fit result (FIG. 9D). Of the outliers, most of them are corresponding to specific circuits, such as outliers 217-224 corresponding to the tricistronic circuit (promoter-luxR-appY-GFP, has 8 data points). Observations with high leverages such as 505-512 are corresponding to the circuit promoter-GFP-Zif23_GCN4. Moreover, some outliers are also high-leverage observations. Given the data sample size (N=632), the original data collection, and the overall data-fitting efficacy, we here didn't exclude the outliers or data with very high leverages (although that would improve the model-fitting efficacy).

Similar analysis was also applied to the data with non-coding ATR, and results showed that 5'ATR size and folding energy $\Delta G_{5'ATR}$, local mRNA folding energy $\Delta G_{-70\_+38}$ are crucial for the best prediction of GFP expression in the comprehensive non-coding ATR model (Table 7). Furthermore, the three variables together explain two-thirds of GFP variations in those synthetic circuits (FIG. 2F, right panel). The model and coefficients were also validated by another statistical software XLSTAT (version 2017.4). Based on the comprehensive non-coding model (FIG. 2F), we then employed XLSTAT to predict GFP expression (mean and standard deviation) in circuits regulated with synthetic ATRs having either different GC contents or different in FIGS. 4C and 4D. Model predicted GFP (FIG. 8C) has a similar expression trend with experimental results (FIGS. 4C and 4D).

We also performed k-fold cross validation to further assess our model performance (k=10). The entire dataset was randomly partitioned into a training dataset, a validation dataset and a testing dataset. The model was built based on the training dataset (50% of the original data) and then validated on the other 25% dataset, and finally was used to assess the performance on the testing dataset (25% of the original data, Table 8). The selection method is stepwise, selection criterion is Schwarz Bayesian Criterion (SBC) and stop criterion is Akaike's Information Criterion (AIC). We performed 10 times of the 10-fold validation, and found that the coefficients for each variable and intercept as well as $R^2$ are very close to the above comprehensive model (Table 8). Moreover, the standard deviation for the square root of mean squared error (RMSE) from the 10 repeats of 10-fold validation is very small (0.0064 for coding ATR, and 0.0128 for non-coding ATR), suggesting the model we built has a decent prediction accuracy and consistency.

In summary, we have demonstrated that the coding and non-coding adjacent transcription regions have remarkable effects on regulating GFP expressions in synthetic operon-based gene circuits (FIGS. 2A-2F). Furthermore, we can use a general biophysical model with sequence-dependent energetic changes to quantify the ATR regulation on gene expression. In this study, we mainly investigated five factors involved in ATR regulation: 5' and 3' ATRs free energies $\Delta G_{5'ATR}$ and $\Delta G_{3'ATR\_100}$, transcriptional sizes and the mRNA folding energy near the GFP starting codon. It is possible that there are some other unknown or uncharacterized factors influencing GFP expression, such as the codon degeneracy for the coding ATRs. Furthermore, there may have some special local secondary or higher structures in some ATRs, which may impact the degradation or translation of GFP.

b. Deterministic Model Construction and Prediction for the Logic Gate

In the four logic gates, GFP expression depends on the relative concentrations of activator (LuxR) and repressor (TetR or LaI) produced from a constitutive promoter. AHL binds with LuxR protein to activate pLux/tet transcription and aTc can block TetR represGsion to pLux/tet. Since the two sets of logic gates (LT/TL and LI/IL) are constructed similarly and described by the same deterministic equations, we here only explain the technical details for the gate LT. The model was built based on our previous work (Wu et al., 2014). From the biochemical reactions depicted in FIG. 3A, we derived the following ordinary differential equations for intercellular concentrations of LuxR (U), TetR (R) and GFP (G):

$$\frac{a}{a} = (k_0 + \alpha_1) - d_1 \cdot U \quad \text{(Eq. 1)}$$

$$\frac{a}{a} = (k_0 + \alpha_2) - d_2 \cdot R \quad \text{(Eq. 2)}$$

$$\frac{a}{a} = \left(c_1 + \frac{K_1 C}{C + K_n}\right) \cdot \frac{1}{K_r^{nt} + (R \cdot F)^{nt}} - d_3 \cdot G \quad \text{(Eq. 3)}$$

and $$f = \frac{AHL^{nt}}{AHL^{nt} + K_r^{nt}} \quad \text{(Eq. 4)}$$

$$C = \frac{(f \cdot U)^2}{K_d} \quad \text{(Eq. 5)}$$

$$F = \frac{1}{K_r^{nr} + ATC^{nr}} \quad \text{(Eq. 6)}$$

The first two equations describe the concentrations of LuxR and TetR, both of which are driven by a constitutive promoter at a constant level ($k_0$). $\alpha_1$ and $\alpha_2$ are constants used to describe the relative changes of LuxR and TetR production, owing to the position changes in the And-gate circuit, $d_1$ and $d_2$ are the degradation rates for the LuxR and TetR protein, respectively. The third equation describes the concentration of GFP, which is determined by the relative concentrations of LuxR and TetR. LuxR binds to AHL molecules and forms the active LuxR monomers in the form of (LuxR-AHL), when the AHL concentration reaches a certain threshold (quorum-sensing mechanism). So the fraction of LuxR monomers (f) bound by AHL can be described by Eq. 4, where ni is the binding cooperativity (Hill coefficient) between LuxR and AHL, and Ki represents the dissociation constant between LuxR and AHL. LuxR needs to form a dimer to bind the promoter and activate transcription, so the concentration of the functional LuxR dimer (C) that binds to the hybrid promoter pLux/tet and activates its transcription can be described by Eq. 5, where $K_d$ is the is the dissociation constant for dimerization. Thus, GFP expression driven by LuxR and inducer AHL is represented by the first part of Eq. 3. $c_1$ is the basal mRNA expression without LuxR protein; $K_1$ is the production rate; and $K_n$ is the dissociation constant between C and pLux/tet promoter. TetR protein can bind and inhibit GFP transcription, and the inhibition can be repressed by inducer aTc. So high GFP expression is achieved in presence of high doses of aTc, and vice versa (Eq. 6). The second part of Eq. 3 describes TetR inhibition to GFP expression, under induction of aTc. And the third part of Eq. 3 is the degradation of GFP.

The three ordinary differential equations were used to model the two sets of AND-gate circuits: LT and TL, LI and IL. For each of the two sets, most parameters should be the same except $\alpha_1$, $\alpha_2$, $c_1$, and $K_i$. Based on the parameter used in our previous studies (Wu et al., 2014), we used the following parameters in our simulations: $k_0$=1.0, $d_1$=0.2, $d_2$=0.2, $d_3$=0.2, $c_1$=0.002 (for TL) or 0.08 (for LT), $K_1$=1.7, $K_n$=4.4, $K_d$=13, $K_i$=400, $K_r$=3.2, ni=1.2, nt=2, ni=1.2, nr=2. For circuits LI and IL, $c_1$=0.002 (for IL) or 0.05 (for LI), $K_i$=1000, and the other parameters are the same.

Figure 8E:
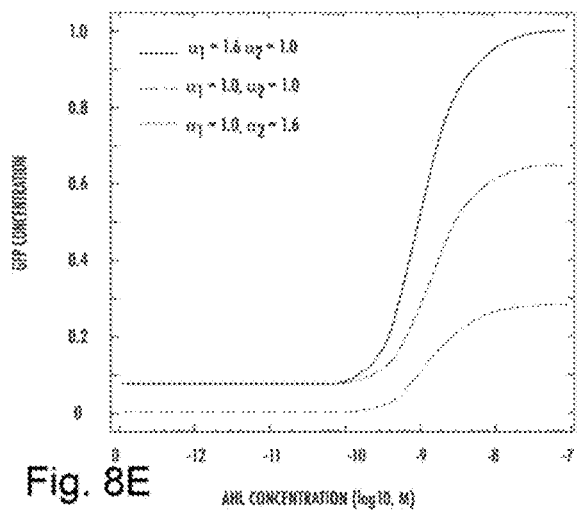

From our comprehensive linear model, we calculated that LT has more LuxR than TetR production (Table 5), so the basal expression c1 is set to a bigger value in LT model. Ki has little effect on the shape of the GFP dynamic curves, but determines the AHL concentration producing half conversion of LuxR monomers into LuxR-HSL complexes (half GFP activation). So the Ki value in the model is acquired from the experimental data. Through changing the relative expression of LuxR and TetR. (i.e. $\alpha_1$ and $\alpha_2$), we can modulate GFP production dynamics (FIG. 8E). To predict the GFP responses in circuit TL with AHL and aTc inductions, we use the parameter $\alpha_1$ and $\alpha_2$ in LT as a control to tune the parameter $\alpha_1$ and $\alpha_2$ in TL. According to the linear model calculations, the production rate for LuxR in LT and TL almost doesn't change, but production rate of TetR in TL increases by ~93% (Table 5). For example, we set the production rates for LuxR and TetR in circuit LT to 1.0 ($k_0+\alpha_1$) and 0.6 ($k_0+\alpha_2$), respectively. So in the circuit TL, the two rates should be 1.0 ($k_0+\alpha_1$) and 1.15 ($k_0+\alpha_2$) based on calculations. For different doses of aTc induction, we allowed ~10% parameter variations for $\alpha_1$ and $\alpha_2$. We found that the model simulations have a good match with our experimental data. The parameters for $\alpha_1$ and $\alpha_2$ in TL and LT under different doses of aTc are listed in Table 2.

TABLE 2

| Circuit | 0 ng/ml | 0.2 ng/ml | 2 ng/ml | 20 ng/ml | 100 ng/ml | 200 ng/ml |
|---|---|---|---|---|---|---|
| LT | $\alpha_1 = 0$ | $\alpha_1 = 0$ | $\alpha_1 = 0$ | $\alpha_1 = 0$ | $\alpha_1 = 0$ | $\alpha_1 = 0$ |
|  | $\alpha_2 = -0.3$ | $\alpha_2 = -0.4$ | $\alpha_2 = -0.38$ | $\alpha_2 = -0.3$ | $\alpha_2 = -0.35$ | $\alpha_2 = -0.25$ |
| TL | $\alpha_1 = 0.1$ | $\alpha_1 = 0.1$ | $\alpha_1 = 0.1$ | $\alpha_1 = 0.1$ | $\alpha_1 = 0.1$ | $\alpha_1 = 0.1$ |
|  | $\alpha_2 = 0.1$ | $\alpha_2 = 0.05$ | $\alpha_2 = 0$ | $\alpha_2 = 0.1$ | $\alpha_2 = 0.1$ | $\alpha_2 = 0.25$ |

Compared to circuit LI, the production rate for LuxR in IL increases by ~74%, and ~38% for LacI (the overall inhibition efficiency may increase by ~76%, Table 5). For example, we set the production rates for LuxR and LacI in circuit LI to 1.0 ($k_0+\alpha_1$) and 0.8 ($k_0+\alpha_2$), respectively. So in the circuit IL, the two rates should be 1.74 ($k_0+\alpha_1$) and ~1.41 ($k_0+\alpha_2$) based on calculations. For different doses of IPTG induction, we allowed ~10% parameter variations for $\alpha_1$ and $\alpha_2$. And the parameters for $\alpha_1$ and $\alpha_2$ in LI and IL under different doses of IPTG are listed in Table 3.

TABLE 3

| Circuit | 0 μM | 0.1 μM | 1 μM | 10 μM | 100 μM | 200 μM | 400 μM |
|---|---|---|---|---|---|---|---|
| LI | $\alpha_1 = 0$ | $\alpha_1 = 0$ | $\alpha_1 = 0$ | $\alpha_1 = 0$ | $\alpha_1 = 0$ | $\alpha_1 = 0$ | $\alpha_1 = 0$ |
|  | $\alpha_2 = -0.1$ | $\alpha_2 = -0.12$ | $\alpha_2 = -0.1$ | $\alpha_2 = -0.15$ | $\alpha_2 = -0.25$ | $\alpha_2 = -0.28$ | $\alpha_2 = -0.2$ |
| IL | $\alpha_1 = 0.57$ | $\alpha_1 = 0.6$ | $\alpha_1 = 0.69$ | $\alpha_1 = 0.82$ | $\alpha_1 = 0.7$ | $\alpha_1 = 0.87$ | $\alpha_1 = 0.57$ |
|  | $\alpha_2 = 0.57$ | $\alpha_2 = 0.5$ | $\alpha_2 = 0.5$ | $\alpha_2 = 0.35$ | $\alpha_2 = 0.4$ | $\alpha_2 = 0.5$ | $\alpha_2 = 0.56$ | c. Bifurcation Analysis for the Synthetic Toggle Switches

For the toggle switch model in FIGS. 5A-5F, we used the same mathematical model and most parameters in the Gardner et al paper (Gardner et al., 2000). Here we think the synthetic ATRs mainly influenced the TetR production rate, with low[7] rate corresponding to T_S28 ($\alpha_1=400$, $\beta=2.7$), medium rate corresponding to T_S67 ($\alpha_1=600$, $\beta=3.0$), and high rate corresponding to T_WT ($\alpha_1=1000$, $\beta=3.245$). All the other parameters are set the same as in Gardner et al paper. Bifurcation analyses are performed using XPP-AUTO software.

4. Additional Tables

Table 4 depicts the linear regression models and coefficients of FIGS. 2A-4D, and Table 5 shows corresponding the model evaluation for each gene's expression in the AND logic gates.

TABLE 4

| Model | FIG. | Variables | Equation* | Mean ($\mu$) | Variance ($\sigma^2$) |
|---|---|---|---|---|---|
| X-GFP (Coding) | FIG. 2A | 5'ATR GC | logGFP = (7.148 ± 0.127) + (4.830 ± 0.325) * log(5'ATR GC) | 5.293 | 0.334 |
|  |  | 5'ATR Size | logGFP = (9.665 ± 0.422) + (−1.439 ± 0.138) * log(5'ATR Size) |  |  |
|  |  | Free energy $dG_{(-70\to+38)}$ | logGFP = (1.703 ± 0.374) + (−2.812 ± 0.292) * (−log(−$dG_{(-70\to+38)}$)) |  |  |
| X-GFP-Y (Coding) | FIG. 2B | 5'ATR GC | logGFP = (5.587 ± 0.055) + (1.939 ± 0.150) * log(5'ATR GC) | 4.908 | 0.088 |
|  |  | 3'ATR GC | logGFP = (5.086 ± 0.076) + (0.538 ± 0.219) * log(3'ATR GC) |  |  |
|  |  | Free energy $dG_{(-70\to+38)}$ | logGFP = (1.988 ± 0.231) + (−2.283 ± 0.180) * (−log(−$dG_{(-70\to+38)}$)) |  |  |
| GFP-X (Coding) | FIG. 2C | 3'ATR GC_100 | logGFP = (6.066 ± 0.082) + (2.168 ± 0.197) * log(3'ATR GC_100) | 5.186 | 0.121 |
|  |  | 3'ATR Size | logGFP = (8.624 ± 0.215) + (−1.132 ± 0.071) * log(3'ATR Size) |  |  |
| X-GFP (Non-Coding) | FIG. 2D | 5'ATR GC | logGFP = (6.500 ± 0.184) + (4.052 ± 0.578) * log(5'ATR GC) | 5.242 | 0.562 |
|  |  | 5'ATR Size | logGFP = (13.723 ± 0.845) + (−2.980 ± 0.297) * log(5'ATR Size) |  |  |
|  |  | Free energy $dG_{(-70\to+38)}$ | logGFP = (1.157 ± 0.573) + (−3.328 ± 0.466) * (−log(−$dG_{(-70\to+38)}$)) |  |  |
| Comprehensive model for Coding ATR | FIG. 2F (Left) | $\Delta G_{5'ATR}$; 5'ATR Size; Free energy $dG_{(-70\to+38)}$; $\Delta G_{3'ATR\_100}$; 3'ATR Size; | logGFP = (11.464 ± 0.432) + (−1.802 ± 0.080) * (−log(−$\Delta G_{5'ATR}$)) + (−3.104 ± 0.149) * log(5'ATR Size) + (−1.121 ± 0.133) * (−log(−$dG_{(-70\to+38)}$)) + (−0.280 ± 0.027) * (−log(−$\Delta G_{3'ATR}\_100$)) + (−1.159 ± 0.080) * log(3'ATR Size) | 5.163 | 0.231 |
| Comprehensive model for Non-coding ATR | FIG. 2F (Right) | $\Delta G_{5'ATR}$; 5'ATR Size; Free energy $dG_{(-70\to+38)}$ | logGFP = (14.451 ± 0.765) + (−3.231 ± 0.338) * (−log(−$\Delta G_{5'ATR}$)) + (−7.278 ± 0.430) * log(5'ATR Size) + (−3.391 ± 0.321) * (−log(−$dG_{(-70\to+38)}$)) | 5.242 | 0.562 |
| Refined model for Non-coding ATR | FIG. S3D | $\Delta G_{5'ATR}$; 5'ATR Size; Free energy $dG_{(-70\to+38)}$ | logGFP = (9.802 ± 0.482) + (−3.524 ± 0.187) * (−log(−$\Delta G_{5'ATR}$)) + (−4.943 ± 0.212) * log(5'ATR Size) + (−1.214 ± 0.304) * (−log(−$dG_{(-70\to+38)}$)) | 5.314 | 0.595 |

TABLE 5

| | Coefficients of the comprehensive model | | | | | |
|---|---|---|---|---|---|---|
| | 5'ATR Size | 3'ATR Size | Free energy | $\Delta G_{5'ATR}$ | $\Delta G_{3'ATR}$ (100 nt) | Intercept |
| AND-Gates | −3.10443 | −1.15864 | −1.1206 | −1.80151 | −0.28049 | 11.4635 |
| CP-LuxR-LacI(LacI) | 815 | 8 | −16.9 | −121.6 | −0.00001 | |
| CP-LuxR-LacI(LuxR) | 8 | 1187 | −70 | −0.05 | −16.6 | |

TABLE 5-continued

|  |  |  |  |  |  | Predicted Expression | Relative expression | Overall efficiency |
|---|---|---|---|---|---|---|---|---|
| CP-LuxR-LacI(LacI) | 2.911157609 | 0.903089987 | −1.227886705 | −2.084933575 | 5 | 5.109207328 |  |  |
| CP-LuxR-LacI(LuxR) | 0.903089987 | 3.074450719 | −1.84509804 | 1.301029996 | −1.220108088 | 5.163765204 |  |  |
| CP-LacI-LuxR(LacI) | 8 | 815 | −70 | −0.05 | −7.1 |  | 1.38132904 | 2.762658081 |
| CP-LacI-LuxR(LuxR) | 1187 | 8 | −15 | −365.5 | −0.00001 |  | 1.743840175 | 1.743840175 |
| CP-LacI-LuxR(LacI) | 0.903089987 | 2.911157609 | −1.84509804 | 1.301029996 | −0.851258349 | 5.24950447 |  |  |
| CP-LacI-LuxR(LuxR) | 3.074450719 | 0.903089987 | −1.176091259 | −2.562887381 | 5 | 5.405271883 |  |  |
| CP-LuxR-TetR(TetR) | 815 | 8 | −12.5 | −121.6 | −0.00001 |  |  |  |
| CP-LuxR-TetR(LuxR) | 8 | 719 | −70 | −0.05 | −11.6 | (10^(TL − LT)) |  |  |
| CP-LuxR-TetR(TetR) | 2.911157609 | 0.903089987 | −1.096910013 | −2.084933575 | 5 | 4.962434847 |  |  |
| CP-LuxR-TetR(LuxR) | 0.903089987 | 2.85672889 | −1.84509804 | 1.301029996 | −1.064457989 | 5.372368128 |  |  |
| CP-TetR-LuxR(TetR) | 8 | 815 | −70 | −0.05 | −7.1 |  | 1.936732422 | 1.936732422 |
| CP-TetR-LuxR(LuxR) | 719 | 8 | −13.7 | −152.5 | −0.00001 |  | 0.956758533 | 0.956758533 |
| CP-TetR-LuxR(TetR) | 0.903089987 | 2.911157609 | −1.84509804 | 1.301029996 | −0.851258349 | 5.24950447 |  |  |
| CP-TetR-LuxR(LuxR) | 2.85672889 | 0.903089987 | −1.136720567 | −2.183269844 | 5 | 5.353170472 |  |  |

Tables 6-8 respectively show the stepwise regression and partial $R^2$ for the each statistically significant variable in FIGS. 2A-2C, the comprehensive models with energetic changes, and the cross validations for the coding and non-coding ATR datasets in FIGS. 2A-2D.

For Table 6, stepwise regression was employed to determine which variable is required for the best fitting efficacy in the models of X-GFP, X-GFP-Y, and GFP-X. 5'ATR GC content is the most important variable in the regression models for X-GFP (partial $R^2=0.44$) and X-GFP-Y (partial $R^2=0.51$) circuits, but 3'ATR size has a bigger role in the model of GFP-X (partial $R^2=0.58$).

For Table 7, stepwise regression was used to determine the model selection for the coding (top section) and non-coding (bottom section) 5'ATR regulation, respectively. Result indicated that $\Delta G_{5'ATR}$, $\Delta G_{3'ATR\_100}$, 5'ATR size, 3'ATR size and $\Delta G_{-70-+38}$ are necessary for the best fitting of the coding ATR experimental data and the five variables explain 63% variation of GFP expression, while 5'ATR size, $\Delta G_{5'ATR}$, and $\Delta G_{-70-+38}$ are required for the best fitting of the non-coding ATR experimental data and explain 67.4% variation. Parameter estimate and standard error for each variable and intercept also listed in the table. All variables left in the model are significant at the level of 0.05. N_ATR_GC: 5'ATR GC content; N_ATR_Size: 5'ATR size; dG: mRNA folding energy (−70 nt~+38 nt); C_ATR_GC: 3'ATR GC content; C_ATR_Size: 3'ATR size; C_ATR_100_GC: GC content of the first 100 nt of 3'ATR; N_ATR_dG: $\Delta G_{5'ATR}$ (5'ATR folding energy); C_ATR_100_dG: $\Delta G_{3'ATR\_100}$.

TABLE 6

Summary of Stepwise Selection

| Step | Variable Entered | Variable Removed | Number Vars In | Partial R-Square | Model R-Square | C(p) | F Value | Pr > F |
|---|---|---|---|---|---|---|---|---|
|  |  |  | X-GFP: |  |  |  |  |  |
| 1 | N_ATR_GC2 |  | 1 | 0.4432 | 0.4432 | 134.929 | 221.25 | <.0001 |
| 2 | N_ATR_Size2 |  | 2 | 0.1537 | 0.5969 | 23.5085 | 105.60 | <.0001 |
| 3 | dG2 |  | 3 | 0.0291 | 0.6260 | 4.0000 | 21.51 | <.0001 |
|  |  |  | X-GFP-Y: |  |  |  |  |  |
| 1 | N_ATR_GC2 |  | 1 | 0.5127 | 0.5127 | 18.3742 | 166.27 | <.0001 |
| 2 | C_ATR_GC2 |  | 2 | 0.0289 | 0.5417 | 10.0171 | 9.91 | 0.0020 |
| 3 | dG2 |  | 3 | 0.0186 | 0.5603 | 5.3454 | 6.61 | 0.0110 |
|  |  |  | GFP-X: |  |  |  |  |  |
| 1 | C_ATR_Size2 |  | 1 | 0.5752 | 0.5752 | 186.943 | 257.27 | <.0001 |
| 2 | C_ATR_100_GC2 |  | 2 | 0.2107 | 0.7859 | 3.0000 | 185.94 | <.0001 |

TABLE 7

| | | | | Coding 5' ATR Regulation | | | | |
|---|---|---|---|---|---|---|---|---|
| | | | | Summary of Stepwise Selection | | | | |
| Step | Variable Entered | Variable Removed | Number Vars In | Partial R-Square | Model R-Square | C(p) | F Value | Pr > F |
| 1 | C_ATR_Size2 | | 1 | 0.0725 | 0.0725 | 946.159 | 49.25 | <.0001 |
| 2 | dG2 | | 2 | 0.1576 | 0.2301 | 680.700 | 128.75 | <.0001 |
| 3 | C_ATR_100_dG2 | | 3 | 0.0903 | 0.3203 | 529.525 | 83.39 | <.0001 |
| 4 | N_ATR_dG2 | | 4 | 0.0566 | 0.3769 | 435.542 | 56.91 | <.0001 |
| 5 | N_ATR_Size2 | | 5 | 0.2543 | 0.6312 | 5.0000 | 431.54 | <.0001 |

| | | Analysis of Variance | | | |
|---|---|---|---|---|---|
| Source | DF | Sum of Squares | Mean Square | F Value | Pr > F |
| Model | 5 | 91.84285 | 18.6857 | 214.24 | <.0001 |
| Error | 626 | 53.67142 | 0.0857 | | |
| Corrected Total | 631 | 145.51427 | | | |

| | | | | |
|---|---|---|---|---|
| Root MSE | | 0.29281 | R-Square | 0.6312 |
| Dependent Mean | | 5.16312 | Adj R-Sq | 0.6282 |
| Coeff Var | | 5.67116 | | |

| | | Parameter Estimates | | | | |
|---|---|---|---|---|---|---|
| Variable | DF | Parameter Estimate | Standard Error | t Value | Pr > |t| | Type II SS |
| Intercept | 1 | 11.46350 | 0.43155 | 26.56 | <.0001 | 60.49930 |
| N_ATR_Size2 | 1 | −3.10443 | 0.14944 | −20.77 | <.0001 | 36.99917 |
| C_ATR_Size2 | 1 | −1.15864 | 0.07953 | −14.57 | <.0001 | 18.19507 |
| N_ATR_dG2 | 1 | −1.80151 | 0.07964 | −22.62 | <.0001 | 43.86968 |
| C_ATR_100_dG2 | 1 | −0.28049 | 0.02672 | −10.50 | <.0001 | 9.44495 |
| dG2 | 1 | −1.12060 | 0.13274 | −8.44 | <.0001 | 6.10990 |

Non-Coding 5' ATR Regulation

| | | | | Summary of Stepwise-Selection | | | | |
|---|---|---|---|---|---|---|---|---|
| Step | Variable Entered | Variable Removed | Number Vars In | Partial R-Square | Model R-Square | C(p) | F Value | Pr > F |
| 1 | C_ATR_Size | | 1 | 0.2766 | 0.2766 | 318.842 | 100.94 | <.0001 |
| 2 | dG2 | | 2 | 0.2832 | 0.5598 | 93.4417 | 169.21 | <.0001 |
| 3 | N_ATR_dG2 | | 3 | 0.1139 | 0.6737 | 4.0000 | 91.44 | <.0001 |

| | | Analysis of Variance | | | |
|---|---|---|---|---|---|
| Source | DF | Sum of Squares | Mean Square | F Value | Pr > F |
| Model | 3 | 100.36041 | 33.45347 | 180.31 | <.0001 |
| Error | 262 | 48.61007 | 0.18553 | | |
| Corrected Total | 265 | 148.97048 | | | |

| | | | | |
|---|---|---|---|---|
| Root MSE | | 0.43074 | R-Square | 0.6737 |
| Dependent Mean | | 5.24196 | Adj R-Sq | 0.6700 |
| Coeff Var | | 8.21710 | | |

| | | Parameter Estimates | | | | |
|---|---|---|---|---|---|---|
| Variable | DF | Parameter Estimate | Standard Error | t Value | Pr > |t| | Type II SS |
| Intercept | 1 | 14.45056 | 0.76488 | 18.89 | <.0001 | 66.22312 |
| N_ATR_Size2 | 1 | −7.27722 | 0.42999 | −16.92 | <.0001 | 53.14271 |
| N_ATR_dG2 | 1 | −3.23089 | 0.33787 | −9.56 | <.0001 | 16.96561 |
| dG2 | 1 | −3.39095 | 0.32107 | −10.56 | <.0001 | 20.69459 |

For Table 8, 10-fold cross-validation was performed and the original dataset was randomly separated into three sets: 50% training, 25% validation, and 25% test. Selection method and criterion are listed in the table. Coefficients and $R^2$ are very close to the values in the comprehensive model (FIG. 2F). Validations are repeated for 10 times and only one run for coding (top section) and non-coding (bottom section) is shown. The standard deviation of the root MSE for coding ATR and non-coding ATR dataset is 0.0064 and 0.0128, respectively.

TABLE 8

| Coding | |
|---|---|
| Data Set | WORK COMPREHENSIVE_3 |
| Dependent Variable | logGFP |
| Selection Method | Stepwise |
| Select Criterion | eSBC |
| Stop Criterion | AIC |
| Choose Criterion | Cross Validation |
| Cross Validation Method | Split |
| Cross Validation Fold | 10 |
| Effect Hierachy Enforced | Single |
| Random Number Seed | 875900001 |
| Number of Observations Read | 632 |
| Number of Observations Used | 632 |
| Number of Observations Used for Training | 316 |
| Number of Observations Used for Validation | 160 |
| Number of Observations Used for Testing | 156 |

| | |
|---|---|
| Root MSE | 0.29935 |
| Dependent Mean | 5.18174 |
| R-Square | 0.6412 |
| Adj R-Sq | 0.6354 |
| AIC | −428.33257 |
| AICC | −437.96894 |
| PRESS | 28.78203 |
| SBC | −733.79812 |
| ASE (Train) | 0.08791 |
| ASE (Validate) | 0.08256 |
| ASE (Test) | 0.08302 |
| CV PRESS | 28.54901 |

Parameter Estimates

| Parameter | DF | Standard Estimate | Error | tValue | Cross Validation Estimates 1 | 2 | 3 |
|---|---|---|---|---|---|---|---|
| Intercept | 1 | 11.345060 | 0.598725 | 18.95 | 10.95 | 11.362 | 11.43 |
| N_ATR_Size2 | 1 | −3.086352 | 0.207626 | −14.86 | −2.95 | −3.038 | −3.08 |
| N_ATR_dG2 | 1 | −1.796675 | 0.111329 | −16.14 | −1.75 | −1.769 | −1.79 |
| C_ATR_100_dG2 | 1 | −0.268296 | 0.038422 | −6.98 | −0.28 | −0.278 | −0.28 |
| C_ATR_Size2 | 1 | −1.126832 | 0.114509 | −9.84 | −1.16 | −1.154 | −1.16 |
| dG2 | 1 | −1.109117 | 0.182197 | −6.09 | −1.28 | −1.092 | −1.10 |

Parameter Estimates

| Parameter | Cross Validation Estimates 4 | 5 | 6 | 7 | 8 | 9 | 10 |
|---|---|---|---|---|---|---|---|
| Intercept | 11.465 | 11.667 | 11.501 | 11.247 | 11.422 | 11.197 | 11.18 |
| N_ATR_Size2 | −3.118 | −3.175 | −3.137 | −3.121 | −3.117 | −3.088 | −3.02 |
| N_ATR_dG2 | −1.805 | −1.827 | −1.814 | −1.819 | −1.813 | −1.805 | −1.77 |
| C_ATR_100_dG2 | −0.263 | −0.265 | −0.265 | −0.252 | −0.272 | −0.256 | −0.27 |
| C_ATR_Size2 | −1.117 | −1.122 | −1.120 | −1.079 | −1.135 | −1.092 | −1.14 |
| dG2 | −1.054 | −0.996 | −1.049 | −1.126 | −1.110 | −1.145 | −1.16 |

| Non-Coding | |
|---|---|
| Data Set | WORK NONCODING_4 |
| Dependent Variable | logGFP |
| Selection Method | Stepwise |
| Select Criterion | SBC |
| Stop Criterion | AIC |
| Choose Criterion | Cross Validation |
| Cross Validation Method | Split |
| Cross Validation Fold | 10 |
| Effect Hierachy Enforced | Single |
| Random Number Seed | 439223001 |
| Number of Observations Read | 287 |
| Number of Observations Used | 266 |
| Number of Observations Used for Training | 129 |
| Number of Observations Used for Validation | 74 |
| Number of Observations Used for Testing | 63 |

| | |
|---|---|
| Root MSE | 0.42722 |
| Dependent Mean | 5.18174 |
| R-Square | 0.7003 |
| Adj R-Sq | 0.6931 |
| AIC | −84.48284 |

TABLE 8-continued

| Coding | |
|---|---|
| AICC | −83.99504 |
| PRESS | 24.19562 |
| SBC | −204.04359 |
| ASE (Train) | 0.17685 |
| ASE (Validate) | 0.17920 |
| ASE (Test) | 0.20480 |
| CV PRESS | 23.68599 |

Parameter Estimates

| | | | Standard | | Cross Validation Estimates | | |
|---|---|---|---|---|---|---|---|
| Parameter | DF | Estimate | Error | tValue | 1 | 2 | 3 |
| Intercept | 1 | 14.327902 | 1.123303 | 12.76 | 14.72 | 14.31 | 14.00 |
| N_ATR_Size2 | 1 | −7.036468 | 0.599681 | −11.73 | −7.34 | −7.07 | −6.83 |
| N_ATR_dG2 | 1 | −2.8864406 | 0.467040 | −6.18 | −3.18 | −2.98 | −2.72 |
| dG2 | 1 | −3.556185 | 0.455899 | −7.80 | −3.43 | −3.49 | −3.64 |

Parameter Estimates

| | Cross Validation Estimates | | | | | | |
|---|---|---|---|---|---|---|---|
| Parameter | 4 | 5 | 6 | 7 | 8 | 9 | 10 |
| Intercept | 14.09 | 13.99 | 14.20 | 14.29 | 14.57 | 14.71 | 14.50 |
| N_ATR_Size2 | −6.92 | −6.94 | −6.95 | −6.99 | −7.10 | −7.15 | −7.12 |
| N_ATR_dG2 | −2.83 | −2.79 | −2.77 | −2.83 | −2.89 | −2.93 | −2.95 |
| dG2 | −3.58 | −3.77 | −3.67 | −3.58 | −3.49 | −3.43 | −3.49 |

Table 9 shows the refined non-coding ATR model with the dataset from FIGS. 2D, 4B, and 4D. The total data points (N) is 576 (266 from FIG. 2B; 190 from FIG. 4B; and 120 from FIG. 4D), and all of the data points and read and used in the analysis. Stepwise regression results indicated that the three variable $\Delta G_{5'ATR}$, i, and $\Delta G_{-70-+38}$ are still required for the best fitting efficacy (top section). Analysis of variance and coefficients for the selected model, and the three variables explain 60.1% of GFP variations. N_ATR_dG: $\Delta G_{5'ATR}$; N_ATR_Size: 5'ATR size (i); dG: mRNA folding energy ($\Delta G_{-70-+38}$) (bottom section).

TABLE 9

Stepwise Regression

Summary of Stepwise Selection

| Step | Variable Entered | Variable Removed | Number Vars In | Partial R-Square | Model R-Square | C(p) | F Value | Pr > F |
|---|---|---|---|---|---|---|---|---|
| 1 | N_ATR_Size2 | | 1 | 0.2694 | 0.2694 | 474.609 | 211.65 | <.0001 |
| 2 | N_ATR_dG2 | | 2 | 0.3201 | 0.5895 | 17.9961 | 446.92 | <.0001 |
| 3 | dG2 | | 3 | 0.0112 | 0.6007 | 4.0000 | 16.00 | <.0001 |

Variance and Coefficient Analysis

Analysis of Variance

| Source | DF | Sum of Squares | Mean Square | F Value | Pr > F |
|---|---|---|---|---|---|
| Model | 3 | 205.62527 | 68.54176 | 286.84 | <.0001 |
| Error | 572 | 136.68203 | 0.23895 | | |
| Corrected Total | 575 | 342.30730 | | | |

| | | | | |
|---|---|---|---|---|
| Root MSE | | 0.48883 | R-Square | 0.6007 |
| Dependent Mean | | 5.31439 | Adj. R-Sq | 0.5986 |
| Coeff Var | | 9.19823 | | |

Parameter Estimates

| Variable | DF | Parameter Estimate | Standard Error | t Value | Pr > |t| | Type II SS |
|---|---|---|---|---|---|---|
| Intercept | 1 | 9.80184 | 0.48189 | 20.34 | <.0001 | 98.86291 |
| N_ATR_Size2 | 1 | −4.94280 | 0.21211 | −23.30 | <.0001 | 129.76009 |
| N_ATR_dG2 | 1 | −3.52435 | 0.18695 | −18.85 | <.0001 | 84.91821 |
| dG2 | 1 | −1.21413 | 0.30357 | −4.00 | <.0001 | 3.82233 |

REFERENCES CITED

1. Ahnert, S. E., Fink. T. M. A., and Zinovyev. A. (2008). How much non-coding DNA do eukaryotes require? J. Theor. Biol. 252, 587-592.
2. Bennett, M. R., and Hasty, J. (2009). Overpowering the component problem. Nat. Biotechnol. 27, 450-451.
3. Brophy, J. A., and Voigt, C. A. (2016). Antisense transcription as a tool to tune gene expression. Mol. Syst. Biol. 12, n/a-n/a.
4. Brophy, J. A. N., and Voigt, C. A. (2014). Principles of genetic circuit design. Nat. Methods 11, 508-520.
5. Cameron, D. E., and Collins, J. J. (2014). Tunable protein degradation in bacteria. Nat. Biotechnol. 32, 1276-1281.
6. Cao, Y., Ryser, M. D., Payne, S., Li, B., Rao, C. V., and You, L. (2016). Collective Space-Sensing Coordinates Pattern Scaling in Engineered Bacteria. Cell 165, 620-630.
7. Carr, S. B., Beal, J., and Densmore, D. M, (2017). Reducing DNA context dependence in bacterial promoters. PloS One 12, e0176013.
8. Chen, H., Shiroguehi, K., Ge, H., and Xie, X. S. (2015a). Genome-wide study of mRNA degradation and transcript elongation in *Escherichia coli*. Mol. Syst. Biol. 11, 781.
9. Chen, Y., Kim, J. K., Himing, A. J., Josic, K., and Bennett, M. R. (2015b). Emergent genetic oscillations in a synthetic microbial consortium. Science 349, 986-989.
10. Chizzolini, F., Forlin, M., Cecchi, D., and Mansy, S. S. (2014). Gene Position More Strongly Influences Cell-Free Protein Expression from Operons than T7 Transcriptional Promoter Strength. ACS Synth. Biol. 3, 363-371.
11. Din, M. O., Danino, T., Prindle, A., Skalak, M., Selimkhanov, J., Allen, K., Julio, E., Atolia, E., Tsimring, L. S., Bhatia, S. N., et al. (2016). Synchronized cycles of bacterial lysis for in vivo delivery. Nature 536, 81-85.
12. Egbert, R. G., and Klavins, E. (2012). Fine-tuning gene networks using simple sequence repeats. Proc. Natl. Acad. Sci. 109, 16817-16822.
13. Elowitz, M. B., and Leibler, S. (2000). A synthetic oscillatory network of transcriptional regulators. Nature 403, 335-338.
14. Emory, S. A., Bouvet, P., and Belasco, J. G. (1992). A 5'-terminal stem-loop structure can stabilize mRNA in *Escherichia coli*. Genes Dev. 6, 135-148.
15. Espah Borujeni, A., and Satis, H. M. (2016). Translation Initiation is Controlled by RNA Folding Kinetics via a Ribosome Drafting Mechanism. J. Am. Chem. Soc. 138, 7016-7023.
16. Farasat, I., Kushwaha, M., Collens, J., Easterbrook, M., Guido, M., and Sails, H. M. (2014). Efficient search, mapping, and optimization of multi protein genetic systems in diverse bacteria. Mol. Syst. Biol. 10, 731,
17. Ferreira, J. P., Overton, K. W., and Wang, C. L. (2013). Tuning gene expression with synthetic upstream open reading frames, Proc. Natl. Acad. Sci. U.S.A. 110, 11284-11289.
18. Gardner, T. S., Cantor, C. R., and Collins, J. J. (2000). Construction of a genetic toggle switch in *Escherichia coli*. Nature 403, 339-342.
19. Kudin. G., Murray, A. W., Tollervey, D., and Plotkin, J. B. (2009). Coding-Sequence Determinants of Gene Expression in *Escherichia coli*. Science 324, 255-258.
20. Lee, J. W., Gyorgy, A., Cameron, D. E., Pyenson, N., Choi, K. R., Way, J. C., Silver, P. A., Vecchio, D. D., and Collins, J. J. (2016). Creating Single-Copy Genetic Circuits. Mol. Cell 63, 329-336,
21. Li, L, Liang, Q., Song, W., and Marchisio, M. A. (2017). Nucleotides upstream of the Kozak sequence strongly influence gene expression in the yeast *S. cerevisiae*. J. Biol. Eng. 11, 25.
22. Lim, H. N., Lee, Y., and Hussein, R. (2011). Fundamental relationship between operon organization and gene expression. Proc. Natl. Acad. Sci. 108, 10626-10631.
23. Litcofsky, K. D., Afeyan, R. B., Krom, R. J., Khalil, A. S., and Collins, J. J. (2012). Iterative plug-and-play methodology for constructing and modifying synthetic gene networks. Nat. Methods 9, 1077-1080.
24. Liu, C., Fu, X., Liu, L., Ren, X., Chau, C. K. L., Li, S., Xiang, L., Zeng, H., Chen, G., Tang, L.-H., et al. (2011). Sequential establishment of stripe patterns in an expanding cell population. Science 334, 238-241.
25. Ma, K. C., Perli, S. D., and Lu, T. K. (2016). Foundations and Emerging Paradigms for Computing in Living Ceils. J. Mol. Biol. 428, 893-915.
26. Mackie, G. A. (2013). RNase E: at the interface of bacterial RNA processing and decay. Nat. Rev. Microbiol. 11, 45-57.
27. Mao, Y., Liu, H., Liu, Y., and Tao, S. (2014). Deciphering the rules by which dynamics of mRNA secondary structure affect translation efficiency in *Saccharomyces cerevisiae*. Nucleic Acids Res. 42, 4813-4822.
28. Mus, F., Crook, M. B., Garcia, K., Costas, A. G., Geddes, B. A., Kouri, E.-D., Paramasivan, P., Ryu. M.-H., Oldroyd, G. E. D., Poole, P. S., et al. (2016). Symbiotic Nitrogen Fixation and Challenges to Extending it to Non-Legumes. Appl. Environ. Microbiol. AEM.01055-16.
29. Mutalik, V. K., Guimaraes, J. C., Cambray, G., Lam, C., Christoffersen, M. J., Mai, Q.-A., Tran, A. B., Pauli, M., Keasling, J. D., Arkin, A. P., et al. (2013). Precise and reliable gene expression via standard transcription and translation initiation elements. Nat. Methods 10, 354-360.
30. Nielsen, A. A. K., Der, B. S., Shin, J., Vaidyanathan, P., Paralanov, V., Strychalski, E. A., Ross, D., Densmore, D., and Voigt, C. A. (2016). Genetic circuit design automation. Science 352, aac7341.
31. Oliva, G., Sahr, T., and Buchrieser, C. (2015). Small RNAs, 5 UTR elements and RNA-binding proteins in intracellular bacteria: impact on metabolism and virulence. FEMS Microbiol. Rev. 39, 331-349.
32. Pardee, K., Green, A. A., Ferrante, T., Cameron, D. E., DaleyKeyser, A., Yin, P., and Collins, J. J. (2014). Paper-Based Synthetic Gene Networks. Cell 159, 940-954.
33. Pardee, K., Green, A. A., Takahashi, M. K., Braff, D., Lambert, G., Lee, J. W., Ferrante, T., Ma, D., Donghia, N., Fan, M, et al. (2016). Rapid, Low-Cost Detection of Zika Virus Using Programmable Biomolecular Components. Cell 165, 1255-1266.
34. Prindle, A., Selimkhanov, J., Li, H., Razinkov, I., Tsimring, L. S., and Hasty, J. (2014). Rapid and tunable post-translational coupling of genetic circuits. Nature 508, 387-391.
35. Rocha, E. P. C. (2008), The Organization of the Bacterial Genome. Annu. Rev. Genet. 42, 211-233.
36. Sails, H. M., Mirsky, E. A., and Voigt, C. A. (2009). Automated Design of Synthetic Ribosome Binding Sites to Precisely Control Protein Expression. Nat. Biotechnoi. 27, 946-950.
37. Seffens, W., and Digby, D. (1999). mRNAs have greater negative folding free energies than shuffled or codon choice randomized sequences. Nucleic Acids Res. 27, 1578-1584.

38. Selinger, D. W., Saxena, R. M., Cheung, K. J., Church, G. M., and Rosenow, C. (2003). Global RNA half-life analysis in *Escherichia coli* reveals positional patterns of transcript degradation. Genome Res. 13, 216-223.
39. Serra, M. J., and Turner, D. H. (1995). Predicting thermodynamic properties of RNA. Methods Enzymol. 259, 242-261.
40. Smanski, M. J., Zhou, H., Claesen, J., Shen, B., Fischbach, M. A., and Voigt, C. A. (2016) Synthetic biology to access and expand nature's chemical diversity. Nat. Rev. Microbiol. 14, 135-149.
41. Smit, M. H. de, and Duin, J. van (1990). Secondary structure of the ribosome binding site determines translational efficiency: a quantitative analysis. Proc. Natl. Acad, Sci. 87, 7668-7672.
42. Taniguchi, Y., Choi, P. J., Li, G.-W., Chen, H., Babu, M., Hearn, J., Emili, A., and Xie, X. S. (2010). Quantifying *E. coli* proteome and transcriptome with single-molecule sensitivity in single cells. Science 329, 533-538.
43. Trotta, E. (2014). On the Normalization of the Minimum Free Energy of RNAs by Sequence Length. PLoS ONE 9.
44. Fuller, T., Waldman, Y. Y., Kupiec, M., and Ruppin, E. (2010). Translation efficiency is determined by both codon bias and folding energy. Proc. Natl. Acad. Sci. 107, 3645-3650.
45. Wright, G. (2014). Perspective: Synthetic biology revives antibiotics. Nature 509, S13.
46. Wu, F., and Wang, X. (2015). Applications of synthetic gene networks. Sci. Prog. 98, 244-252,
47. Wu, F., Menn, D. J., and Wang, X. (2014). Quorum-sensing crosstalk-driven synthetic circuits: from unimodality to trimodality. Chem. Biol. 21, 1629-1638.
48. Wu, F., Su, R.-Q., Lai, Y.-C., and Wang, X. (2017). Engineering of a synthetic quadrastable gene network to approach Waddington landscape and cell fate determination. eLife 6, e23702
49. Xia, T., SantaLucia, J., Burkard, M. E., Kierzek, R., Schroeder, S. J., Jiao, X., Cox, C., and Turner, D. H. (1998). Thermodynamic parameters for an expanded nearest-neighbor model for formation of RNA duplexes with Watson-Crick base pairs. Biochemistry (Mosc.) 37, 14719-14735.
50. Yang, L., Nielsen, A. A. K., Fernandez-Rodriguez, J., McClune, C. J., Laub, M. T., Lu, T. K., and Voigt, C. A. (2014). Permanent genetic memory with >1-byte capacity. Nat. Methods 11, 1261-1266.
51. Yeung, E., Dy, A. J., Martin, K. B., Ng, A. H., Del Vecchio, D., Beck, J. L., Collins, J. J., and Murray, R. M. (2017). Biophysical Constraints Arising from Compositional Context in Synthetic Gene Networks. Cell Syst. 5, 11-24.e12.
52. Zadeh, J. N., Steenberg, C. D., Bois, J. S., Wolfe, B. R., Pierce, M. B., Khan, A. R., Dirks, R. M., and Pierce, N. A. (2011). NUPACK: Analysis and design of nucleic acid systems. J. Comput. Chem. 32, 170-173.
53. Zhang, W., and Nielsen, D. R. (2014). Synthetic biology applications in industrial microbiology. Front. Microbiol. 5.

The invention claimed is:

1. A method of tuning the performance of a synthetic gene circuit comprising an operon having a plurality of genes, the method comprising:
quantifying, for each gene of the plurality of genes, a relative gene expression metric, the relative gene expression metric of the gene quantified by:
determining a number (i) of nucleotides in a 5' adjacent transcriptional region (ATR) of the gene;
determining a number (j) of nucleotides in a 3' ATR of the gene;
determining a minimum free energy ($\Delta G_{-70\rightarrow+38}$) of a mRNA secondary structure around a ribosome binding site (RBS) of the gene;
determining a total folding energy ($\Delta G_{5'ATR}$) for the 5' ATR of the gene;
determining a folding energy ($\Delta G_{3'ATR\_100}$) for the first 100 nucleotides of the 3' ATR of the gene; and
calculating the relative gene expression metric by summing sequence-dependent energy changes, the sum comprising $$\beta 0 + \beta 1 \cdot \Delta G_{5'ATR} + \beta 2 \cdot \Delta G_{3'ATR\_100} + \beta 3 \cdot i \cdot Gm + \beta 4 \cdot j \cdot Gm + \beta 5 \cdot \Delta G_{-70\rightarrow+38}$$

where $\beta 1$, $\beta 2$, $\beta 3$, $\beta 4$, and $\beta 5$ are scaling coefficients, and Gm represents an average energy cost for synthesizing a nucleotide;
simulating the performance of an intended function of the synthetic gene circuit through applying the relative gene expression metrics of the plurality of genes to a deterministic model to evaluate the performance of the synthetic gene circuit, the deterministic model being one of an ordinary differential equation model and a bifurcation analysis; and
assembling the synthetic gene circuit.

2. The method of claim 1, wherein the intended function is an AND logic gate, and the deterministic model applies the relative gene expression metrics to an ordinary differential equation model.

3. The method of claim 1, wherein the intended function is a bistable toggle switch, and the deterministic model comprises bifurcation analysis of the relative gene expression metrics.

4. The method of claim 1, wherein i is between 299 and 2001 nucleotides.

5. The method of claim 1, wherein the 5' ATR and 3' ATR each have GC contents ranging from 28% to 66%.

6. The method of claim 1, wherein the plurality of genes is two or three genes.

7. A method of tuning the performance of a synthetic gene circuit comprising an operon having a plurality of genes, the method comprising:
quantifying, for each gene of the plurality of genes, a relative gene expression metric, the relative gene expression metric of the gene quantified by:
determining a number (i) of nucleotides in a 5' adjacent transcriptional region (ATR) of the gene;
determining a number (j) of nucleotides in a 3' ATR of the gene;
determining a minimum free energy ($\Delta G_{-70\rightarrow+38}$) of a mRNA secondary structure around a ribosome binding site (RBS) of the gene;
determining a total folding energy ($\Delta G_{5'ATR}$) for the 5' ATR of the gene;
determining a folding energy ($\Delta G_{3'ATR\_100}$) for the first 100 nucleotides of the 3' ATR of the gene; and
calculating the relative gene expression metric by summing sequence-dependent energy changes, the sum comprising $$\beta 0 + \beta 1 \cdot \Delta G_{5'ATR} + \beta 2 \cdot \Delta G_{3'ATR\_100} + \beta 3 \cdot i \cdot Gm + \beta 4 \cdot j \cdot Gm + \beta 5 \cdot \Delta G_{-70\rightarrow+38}$$

where $\beta 1$, $\beta 2$, $\beta 3$, $\beta 4$, and $\beta 5$ are scaling coefficients, and Gm represents an average energy cost for synthesizing a nucleotide;
simulating the performance of an intended function of the synthetic gene circuit using the relative gene expression metrics of the plurality of genes to evaluate the performance of the synthetic gene circuit; and assembling the synthetic gene circuit.

8. The method of claim 7, wherein the intended function is a logic gate, simulating the performance of the intended function comprises applying the relative gene expression metrics of the plurality of genes to an ordinary differential equation model.

9. The method of claim 7, wherein the intended function is a bistable toggle switch, and simulating the performance of the intended function comprises performing a bifurcation analysis of the relative gene expression metrics of the plurality of genes.

10. The method of claim 7, wherein i is between 299 and 2001 nucleotides.

11. The method of claim 7, wherein the plurality of genes is two or three genes.

12. The method of claim 7, wherein the 5' ATR and 3' ATR both have GC contents ranging from 28% to 66%.

13. A method of tuning the performance of a synthetic gene circuit comprising an operon having a plurality of genes, the method comprising:
    quantifying, for each gene of the plurality of genes, a relative gene expression metric, the relative gene expression metric of the gene quantified by:
        determining a number (i) of nucleotides in a 5' adjacent transcriptional region (ATR) of the gene;
        determining a number (j) of nucleotides in a 3' ATR of the gene;
        determining a minimum free energy ($\Delta G_{-70 \to +38}$) of a mRNA secondary structure around a ribosome binding site (RBS) of the gene;
        determining a total folding energy ($\Delta G_{5'ATR}$) for the 5' ATR of the gene;
        determining a folding energy ($\Delta G_{3'ATR\_100}$) for the first 100 nucleotides of the 3' ATR of the gene; and
        calculating the relative gene expression metric by summing sequence-dependent energy changes, the sum comprising $$\beta 0 + \beta 1 \cdot \Delta G_{5'ATR} + \beta 2 \cdot \Delta G_{3'ATR\_100} + \beta 3 \cdot i \cdot Gm + \beta 4 \cdot j \cdot Gm + \beta 5 \cdot \Delta G_{-70 \to +38}$$

where β1, β2, β3, β4, and β5 are scaling coefficients and Gm represents an average energy cost for synthesizing a nucleotide;
    simulating the performance of an intended function of the synthetic gene circuit using the relative gene expression metrics of the plurality of genes to evaluate the performance of the synthetic gene circuit.

14. The method of claim 13, wherein simulating the performance of the intended function comprises applying the relative gene expression metrics of the plurality of genes to a deterministic model.

15. The method of claim 14, wherein the deterministic model is an ordinary differential equation model.

16. The method of claim 13, wherein the intended function is one of a logic gate, a multistable toggle switch, and an oscillator.

17. The method of claim 13, wherein the plurality of genes is two or three genes.

18. The method of claim 13, wherein i is between 299 and 2001 nucleotides.

19. The method of claim 13, wherein the 5' ATR and 3' ATR both have GC contents ranging from 28% to 66%.

20. The method of claim 13, further comprising assembling the synthetic gene circuit.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: primer sequences

<400> SEQUENCE: 1
gaatgccacg gtgaatacgt t                                             21

<210> SEQ ID NO 2
<211> LENGTH: 20
<212> TYPE: DNA
<213> ORGANISM: Artificial Sequence
<220> FEATURE:
<223> OTHER INFORMATION: primer sequences

<400> SEQUENCE: 2
cacaaagtgg taagcgccct                                               20

<210> SEQ ID NO 3
<211> LENGTH: 21
<212> TYPE: DNA
<213> ORGANISM: Artificial Sequence
<220> FEATURE:
<223> OTHER INFORMATION: primer sequences

<400> SEQUENCE: 3
cagtggagag ggtgaaggtg a                                             21

<210> SEQ ID NO 4
<211> LENGTH: 22
<212> TYPE: DNA
<213> ORGANISM: Artificial Sequence
```

```
<220> FEATURE:
<223> OTHER INFORMATION: primer sequences

<400> SEQUENCE: 4
cctgtacata accttcgggc at                                            22

<210> SEQ ID NO 5
<211> LENGTH: 20
<212> TYPE: DNA
<213> ORGANISM: Artificial Sequence
<220> FEATURE:
<223> OTHER INFORMATION: primer sequences

<400> SEQUENCE: 5
agacacgtgc tgaagtcaag                                               20

<210> SEQ ID NO 6
<211> LENGTH: 22
<212> TYPE: DNA
<213> ORGANISM: Artificial Sequence
<220> FEATURE:
<223> OTHER INFORMATION: primer sequences

<400> SEQUENCE: 6
tctgctagtt gaacgcttcc at                                            22
```